US005776761A

United States Patent [19]

Rogers et al.

[11] Patent Number: 5,776,761
[45] Date of Patent: Jul. 7, 1998

[54] NUCLEIC ACIDS ENCODING ALLERGENIC PROTEINS FROM RAGWEED

[75] Inventors: Bruce Rogers, Cambridge, Mass.; David G. Klapper, Chapel Hill, N.C.; Thorunn Rafnar, Baltimore, Md.; Mei-chang Kuo, Winchester, Mass.

[73] Assignees: ImmuLogic Pharmaceutical Corporation, Waltham, Mass.; University of North Carolina at Chapel Hill, Chapel Hill, N.C.

[21] Appl. No.: 175,069

[22] Filed: Dec. 29, 1993

Related U.S. Application Data

[60] Division of Ser. No. 529,951, May 29, 1990, abandoned, which is a continuation-in-part of Ser. No. 325,365, Mar. 17, 1989, abandoned.

[51] Int. Cl.$^6$ .............................. C12N 1/21; C12N 15/29; C12N 15/63
[52] U.S. Cl. .................. 435/252.3; 536/236; 435/320.1; 424/275.1; 935/12; 935/65
[58] Field of Search ................ 536/23.6; 435/320.1, 435/252.3, 240.2, 240.4, 254.11; 935/65, 12; 424/275.1

[56] References Cited

PUBLICATIONS

Margalit, H. et al., 1987. J. Immunol. vol. 138 pp. 2213–2229.
Atassi, M.Z. et al. 1987 In *Antigen*specific T cell Receptors and Factors, vol. I ed. JJ. Marchalonis, CRC Press, Boca Raton Florida, pp. 7–63.
Kuo, M.C. et al. 1993. Molecular Immunology vol. 30 pp. 1077–1087.
Hatton, T.W. et al. 1988. J. Allergy Clin. Immunol. vol 81 p. 183.
Wallace R. et al. 1987. Meth. Enzymol. vol 152 pp. 432–442.
Adolphson, C. et al. 1978. J. Allergy Clin. Immunol. vol. 62 pp. 197–210.
Matsudaira , P. 1990. Meth. Enzymol. vol. 182 pp. 602–613.
Stinson, J.R. et al. 1987. Plant Physiol. vol. 83 pp. 442–447.
Young, R.A. et al. 1985. Proc. Natl. Acad. Sci. USA vol. 82 pp. 2583–2587.
Baer, H. et al. 1980. J. Allergy Clin. Immunol. vol. 66 pp. 281–285.
Fang, K.S.Y. et al. 1988. Proc. Natl. Acad. Sci. USA vol. 85 pp. 895–899.
Wing, R.A. et al. 1989. Plant Molecular Biology vol. 14 pp. 17–28.

Boswell, D.R. et al. 1988. In Computational Molecular Biology, ed. A.M. Lesk, Oxford Univ. Press, pp. 161–178.
Goodfriend et al., *Molecular Immunology*, 22(8): 899–906 (1985).
Ishizaka et al., *Journal of Immunology*, 114(1): 110–115 (1975).
King et al., *Biochemistry*, 3(3): 458–468 (Mar., 1964).
King et al., *Advanced Immunology*, 23: 77–105 (1976).
King et al., *Arch. Biochem. Biophy.*, 212(1): 127–135 (1981).
King et al., *Immunochemistry*, 11: 83–92 (1974).
King et al., *Biochemistry*, 1(4): 709–720 (1962).
King et al., *Biochemistry*, 11(3): 367–371 (1972).
Lamb et al., *J. Exper Med.*, 157: 1434–1447 (May, 1983).
Lerner et al., *Nature*, 299:592–596 (Oct. 14, 1982).
Litwin et al., *Int. Archs of Appl Immunol.*, 87: 361–366 (1988).
Litwin et al., *Clinical and Experimental Allergy*, 21:457–465 (1991).
Lowenstein et al., *J. of Immunology*, 127(2): 637–642 (1981).
Marsh et al., *Immunogenetics*, 26: 230–236 (1987).
Marsh et al., *Bull. World Health Org.* 64(5): 767–770 (1986).
Michael et al., *Clinical Exper. Allergy*, 20: 669–674 (1990).
Muckerheide et al., *Cellular Immunology*, 50: 340–347 (1980).
Olson et al., *J. of Immunology*, 136(6): 2109–2115 (Mar. 15, 1986).
Paull et al., *Journal of Allergy and Clinical Immunol.*, 64(6) (Dec. 1979).
Scherer, Cold Spring Harbor Press, Cold Spring Harbor (1989).
Smith, et al., *Molecular Immunology*, 1988, 25(4):355–365.
Takatsu, et al., *Journal of Immunology*, 115(6): 1469–1476 (1975).
Young, et al., *Proc. Natl. Acad. Sci. USA* , 80: 1194–1198 (Mar., 1983).
Livingstone, et al., *Ann Rev. Immunology*, 5: 477–501 (1987).

*Primary Examiner*—Mary E. Mosher
*Attorney, Agent, or Firm*—Lahive & Cockfield, LL

[57] ABSTRACT

Antigen E or Amb a I of ragweed pollen has been shown to be a family or families of proteins. cDNAs encoding Amb a I, the major human allergen of ragweed and Amb a II, peptides derived from Amb a I or Amb a II, antibodies against the peptides; and methods of treating individuals for sensitivity to ragweed are disclosed.

20 Claims, 36 Drawing Sheets

DE UNC CLONE 1

FIG. 2

```
          10        20        30        40        50        60
          |         |         |         |         |         |
GAATTCGGCTGGAGAACGAATAAAGACGTGCTTGAAAATGGTGCTATTTTTGTTGCATCC

E  F  G  W  R  T  N  K  D  V  L  E  N  G  A  I  F  V  A  S 70        80        90       100       110       120
          |         |         |         |         |         |
GGGGTCGATCCAGTGCTAACCCCTGAGCAAAGCGCAGGGATGATTCCAGCCGAACCAGGA

G  V  D  P  V  L  T  P  E  Q  S  A  G  M  I  P  A  E  P  G 130       140       150       160       170       180
          |         |         |         |         |         |
GAGTCCGCTCTAAGCCTCACTAGTAGTGCTGGTGTACTCTCATGCCAACCCGGAGCACCT

E  S  A  L  S  L  T  S  S  A  G  V  L  S  C  Q  P  G  A  P 190       200       210       220       230       240
          |         |         |         |         |         |
TGCTAAGCACCCGACCAATTACTAAGCACTTATAATGATCATTAATACTTTTTTTTATTT

C  -  A  P  D  Q  L  L  S  T  Y  N  D  H  -  Y  F  F  L  F 250       260       270       280       290       300
          |         |         |         |         |         |
TATTTTTGATATTTTATATGTACTAAGGTAATGGAAATGAACCTTTACCTTCTAGTACTC

Y  F  -  Y  F  I  C  T  K  V  M  E  M  N  L  Y  L  L  V  L 310       320
          |         |
TAAAAAAAAAAAAAAACCGAATTC    (SEQ. ID NO:56)
   -  K  K  K  K  P  N      (SEQ. ID NO:57)
```

FIG. 3A

```
*******************************************
* TRANSLATION OF A NUCLEIC ACID SEQUENCE *
*******************************************
Done on DNA sequence AMB_A_IB_K.

DE    SEQUENCE OF AMB A IB CLONE.

Total number of bases is: 1328.
Analysis done on the complete sequence.
Done on (absolute) phase(s): 1.
Using the Universal genetic code.
```

```
              10        20        30        40        50        60
               |         |         |         |         |         |
          TACATCTTGTATTTTACCTTAGCCCTTGTCACTTTGCTGCAACCTGTTCGTTCTGCAGAA
            Y  I  L  Y  F  T  L  A  L  V  T  L  L  Q  P  V  R  S  A  E 70        80        90       100       110       120
               |         |         |         |         |         |
          GATGTTGAAGAATTCTTACCTTCAGCTAACGAAACAAGGAGGAGCCTGAAAGCATGTGAA
            D  V  E  E  F  L  P  S  A  N  E  T  R  R  S  L  K  A  C  E 130       140       150       160       170       180
               |         |         |         |         |         |
          GCACACAACATTATAGACAAGTGCTGGAGGTGCAAAGCCGATTGGGCGAATAACCGACAA
            A  H  N  I  I  D  K  C  W  R  C  K  A  D  W  A  N  N  R  Q 190       200       210       220       230       240
               |         |         |         |         |         |
          GCGTTAGCCGATTGTGCCCAAGGTTTTGCAAAGGGAACCTACGGTGGAAAACATGGTGAT
            A  L  A  D  C  A  Q  G  F  A  K  G  T  Y  G  G  K  H  G  D 250       260       270       280       290       300
               |         |         |         |         |         |
          GTCTACACGGTCACCAGTGATAAAGATGATGATGTTGCAAATCCAAAAGAAGGCACACTC
            V  Y  T  V  T  S  D  K  D  D  D  V  A  N  P  K  E  G  T  L 310       320       330       340       350       360
               |         |         |         |         |         |
          CGGTTTGCTGCTGCCCAAAACAGGCCCTTGTGGATCATTTTTAAAAGAAATATGGTGATT
            R  F  A  A  A  Q  N  R  P  L  W  I  I  F  K  R  N  M  V  I 370       380       390       400       410       420
               |         |         |         |         |         |
          CATTTGAATCAAGAGCTTGTCGTAAACAGCGACAAGACCATCGATGGCCGAGGGGTGAAA
            H  L  N  Q  E  L  V  V  N  S  D  K  T  I  D  G  R  G  V  K
```

FIG.3B

```
        430       440       450       460       470       480
         |         |         |         |         |         |
GTTAACATCGTTAACGCCGGTCTCACCCTCATGAATGTCAAGAATATAATCATTCATAAC
  V  N  I  V  N  A  G  L  T  L  M  N  V  K  N  I  I  H  N 490       500       510       520       530       540
         |         |         |         |         |         |
ATAAATATCCATGATATTAAAGTTTGTCCAGGAGGCATGATTAAGTCCAACGATGGTCCA
  I  N  I  H  D  I  K  V  C  P  G  G  M  I  K  S  N  D  P 550       560       570       580       590       600
         |         |         |         |         |         |
CCAATTTTAAGACAACAAAGTGATGGTGATGCTATAAATGTTGCTGGTAGTTCACAAATA
  P  I  L  R  Q  Q  S  D  G  D  A  I  N  V  A  G  S  S  Q  I 610       620       630       640       650       660
         |         |         |         |         |         |
TGGATCGACCATTGCTCGCTCAGTAAGGCTTCCGATGGGCTGCTCGATATCACCCTCGGC
  W  I  D  H  C  S  L  S  K  A  S  D  G  L  L  D  I  T  L  G 670       680       690       700       710       720
         |         |         |         |         |         |
AGCTCACACGTGACCGTTTCCAACTGCAAATTCACCCAACACCAATTTGTATTATTGCTC
  S  S  H  V  T  V  S  N  C  K  F  T  Q  H  Q  F  V  L  L  L 730       740       750       760       770       780
         |         |         |         |         |         |
GGGGCTGATGACACCCATTATCAAGATAAAGGCATGCTAGCAACGGTAGCATTCAACATG
  G  A  D  D  T  H  Y  Q  D  K  G  M  L  A  T  V  A  F  N  M 790       800       810       820       830       840
         |         |         |         |         |         |
TTCACCGATCACGTTGACCAAAGAATGCCTAGATGTAGATTTGGGTTTTTCCAAGTCGTT
  F  T  D  H  V  D  Q  R  M  P  R  C  R  F  G  F  F  Q  V  V 850       860       870       880       890       900
         |         |         |         |         |         |
AACAACAACTACGACAGATGGGGAACGTACGCCATCGGTGGTAGCTCGGCCCCAACTATA
  N  N  N  Y  D  R  W  G  T  Y  A  I  G  G  S  S  A  P  T  I 910       920       930       940       950       960
         |         |         |         |         |         |
CTCAGCCAAGGGAACAGATTCTTCGCCCCCGATGATATCATCAAGGAAAATGTCTTAGCG
  L  S  Q  G  N  R  F  F  A  P  D  D  I  I  K  E  N  V  L  A
```

FIG.3C

```
         970       980       990      1000      1010      1020
          |         |         |         |         |         |
    AGGACTGGTACTGGCAACGCAGAGTCGATGTCGTGGAACTGGAGAACAGATAAAGACTTG
     R  T  G  T  G  N  A  E  S  M  S  W  N  W  R  T  D  K  D  L 1030      1040      1050      1060      1070      1080
          |         |         |         |         |         |
    CTTGAAAATGGTGCTATTTTTCTCCCATCCGGGTCTGATCCAGTGCTAACCCCTGAGCAA
     L  E  N  G  A  I  F  L  P  S  G  S  D  P  V  L  T  P  E  Q 1090      1100      1110      1120      1130      1140
          |         |         |         |         |         |
    AAAGCAGGGATGATTCCAGCTGAACCAGGAGAAGCCGTTCTAAGACTCACTAGTAGTGCT
     K  A  G  M  I  P  A  E  P  G  E  A  V  L  R  L  T  S  S  A 1150      1160      1170      1180      1190      1200
          |         |         |         |         |         |
    GGTGTACTCTCATGCCATCAAGGAGCACCTTGCTAAGCACCTGGCCAATTCCTAAGCTTT
     G  V  L  S  C  H  Q  G  A  P  C  -  A  P  G  Q  F  L  S  F 1210      1220      1230      1240      1250      1260
          |         |         |         |         |         |
    TATAATAATCATAAATACTTATTTTATTTTATTTTTGATATTTTATATGAACCATTACGT
     Y  N  N  H  K  Y  L  F  Y  F  I  F  D  I  L  Y  E  P  L  R 1270      1280      1290      1300      1310      1320
          |         |         |         |         |         |
    TCAAGTACTCTATTAACATGTTTTAAATTCATAAGAGTTTATTGATAAAAAAAAAAAAAA
     S  S  T  L  L  T  C  F  K  F  I  R  V  Y  -  -  K  K  K  K
```

CCGAATTC (SEQ. ID NO:58)
 P  N (SEQ. ID NO:59)

FIG.4A

```
*******************************************
* TRANSLATION OF A NUCLEIC ACID SEQUENCE *
*******************************************

Done on DNA sequence KKLAPPER1.

DE    UNC CLONE 1

Total number of bases is: 323.
Analysis done on the complete sequence.
Done on (absolute) phase(s): 1.
Using the Universal genetic code.
```

```
           10        20        30        40        50        60
            |         |         |         |         |         |
         GAATTCGGCTGGAGAACGAATAAAGACGTGCTTGAAAATGGTGCTATTTTTGTTGCATCC

E  F  G  W  R  T  N  K  D  V  L  E  N  G  A  I  F  V  A  S 70        80        90       100       110       120
            |         |         |         |         |         |
         GGGGTCGATCCAGTGCTAACCCCTGAGCAAAGCGCAGGGATGATTCCAGCCGAACCAGGA

G  V  D  P  V  L  T  P  E  Q  S  A  G  H  I  P  A  E  P  G 130       140       150       160       170       180
            |         |         |         |         |         |
         GAGTCCGCTCTAAGCCTCACTAGTAGTGCTGGTGTACTCTCATGCCAACCCGGAGCACCT

E  S  A  L  S  L  T  S  S  A  G  V  L  S  C  Q  P  G  A  P 190       200       210       220       230       240
            |         |         |         |         |         |
         TGCTAAGCACCCGACCAATTACTAAGCACTTATAATGATCATTAATACTTTTTTTTATTT

TATTTTGATATTTTATATGTACTAAGGTAATGAAATGGAAATGAACCTTTACCTTCTAGTACTC

Y F - Y F I C T K V M E M N L Y L L V L (SEQ. ID NO:61)

310        320

TAAAAAAAAAAAAACCGAATTC (SEQ. ID NO:60)

FIG.5

IPC CLONE #1

From:

```
              10         20         30         40         50         60
              |          |          |          |          |          |
    1 GAATTCCGAT TCTTGGAGGA ATTACCGAAG TTAAAGACAA TGATAACAGC GTCGATTTCG
      CTTAAGGCTA AGAACCTCCT TAATGGCTTC AATTTCTGTT ACTATTGTCG CAGCTAAAGC

61 ACGAGCTTGC TAAATTCGCC ATCGCTGAAC ACAACAAGAA GGAGAATGCT GCTCTGGAGT
      TGCTCGAACG ATTTAAGCGG TAGCGACTTG TGTTGTTCTT CCTCTTACGA CGAGACCTCA

121 TTGGAAAAGT AATAGAAAAA AAGCAGCAGG CGGTACAGGG CACCATGTAT TATATAAAAG
      AACCTTTTCA TTATCTTTTT TTCGTCGTCC GCCATGTCCC GTGGTACATA ATATATTTTC

181 TGGAAGCAAA TGATGGTGGT GAGAAGAAAA CTTATGAAGC CAAGGTGTGG GTTAAGCTAT
      ACCTTCGTTT ACTACCACCA CTCTTCTTTT GAATACTTCG GTTCCACACC CAATTCGATA

241 GGGAAAATTT CAAGGAATTG CAGGAACTCA AACTTGTTTG ATGGACGGGT GTGTGCTATG
      CCCTTTTAAA GTTCCTTAAC GTCCTTGAGT TTGAACAAAC TACCTGCCCA CACACGATAC

301 ACAAAATAGC TCGAGCAGGT GAAGCATGAA TGTATAAATA TTCTTTTTAA GTTTAATAAT
      TGTTTTATCG AGCTCGTCCA CTTCGTACTT ACATATTTAT AAGAAAAATT CAAATTATTA

361 AAACATTTCT TGTAATATGG TACAGGTTTA TGTACTTTGG TATGTATAAC AGAAAACATA
      TTTGTAAAGA ACATTATACC ATGTCCAAAT ACATGAAACC ATACATATTG TCTTTTGTAT

421 TCATAAATTC AAACTTAGAA TTTTGGGAAT TC    (SEQ. ID NO:62)
      AGTATTTAAG TTTGAATCTT AAAACCCTTA AG    (SEQ. ID NO:63)
```

Total number of bases is: 452.
DNA sequence composition:      162 A;      59 C;     107 G;     124 T;

Sequence name: NIPC_CLONE1.

FIG.6

IPC CLONE #5

From:

```
                  10         20         30         40         50         60
                   |          |          |          |          |          |
     1  GAATTCCCGA TTCTTGGAGG AATTACCGAA GTTAAAGACA ATGATAACAG CGTCGATTTC
        CTTAAGGGCT AAGAACCTCC TTAATGGCTT CAATTTCTGT TACTATTGTC GCAGCTAAAG

61  GACGAGCTTG CTAAATTCGC CATCACTGAA CACAACAAGA AGGAGAATGC TGCTCTGGAG
        CTGCTCGAAC GATTTAAGCG GTAGTGACTT GTGTTGTTCT TCCTCTTACG ACGAGACCTC

121  TTTGGAAAAG TAATAGAAAA AAAGCAGCAG GCGGTACAGG GCACCATGTA TTATATAAAA
        AAACCTTTTC ATTATCTTTT TTTCGTCGTC CGCCATGTCC CGTGGTACAT AATATATTTT

181  GCGGAAGCAA ATGATGGTGG TGAGAAGAAA ACTTATGAAG CCAAGGTGTG GGTTAAGCTA
        CGCCTTCGTT TACTACCACC ACTCTTCTTT TGAATACTTC GGTTCCACAC CCAATTCGAT

241  TGGGAAAATT TCAAGGAATT TGCAAGGAAC TCAAACCTTG TTTGATGATG CCACCTCACC
        ACCCTTTTAA AGTTCCTTAA ACGTTCCTTG AGTTTGGAAC AAACTACTAC GGTGGAGTGG

301  TTAACTCCAT ATGGACGGTG TGCTATGACA AAATAGCTCA AGGAGGTGAA GCATAAATGT
        AATTGAGGTA TACCTGCCAC ACGATACTGT TTTATCGAGT TCCTCCACTT CGTATTTACA

361  ATAAATATTC TTTTTAAGTT TAATAATAAA CATTTCTTGT AATATAGTAC AAGTTTATGT
        TATTTATAAG AAAAATTCAA ATTATTATTT GTAAAGAACA TTATATCATG TTCAAATACA

421  ACTTTGGTAT GTATAACAGA AAACATATCA TAAATTCAAA CTTAATGTTT TTTTTTCTCG
        TGAAACCATA CATATTGTCT TTTGTATAGT ATTTAAGTTT GAATTACAAA AAAAAAGAGC

481  CGGAATTC     (SEQ. ID NO:64)
        GCCTTAAG     (SEQ. ID NO:65)
```

Total number of bases is: 488.
DNA sequence composition:   174 A;   74 C;   103 G;   137 T;

Sequence name: NIPC_CLONE5.

FIG.7

IPC CLONE #6

From:

```
             10         20         30         40         50         60
             |          |          |          |          |          |
  1  TCGATTCGCT GTCGATGAAC ACAACAAGAA GCAGAATACC CTGCTGGAAT TTAAGAAGT
     AGCTAAGCGA CAGCTACTTG TGTTGTTCTT CGTCTTATGG GACGACCTTA AATTCTTCCA

61  ACTGAATACA AAGGAGCAGG TAGTAGCTGG TATAATGTAT TATATCACAC TTGAAGCAAC
     TGACTTATGT TTCCTCGTCC ATCATCGACC ATATTACATA ATATAGTGTG AACTTCGTTG

121  TGATGGTGGT GAGAAAAGA CTTATGAAGC CAAGGTTTGG GTTAAGCCAT GGGAAACTT
     ACTACCACCA CTCTTTTTCT GAATACTTCG GTTCCAAACC CAATTCGGTA CCCTTTTGAA

181  CAAAGAATTC    (SEQ. ID NO:66)
     GTTTCTTAAG    (SEQ. ID NO:67)
```

Total number of bases is: 190.
DNA sequence composition:  69 A;  29 C;  47 G;  45 T;

Sequence name: NIPC_CLONE6.

FIG. 8
IPC CLONE 1

The DNA inspector II e          Open Reading Frame Analysis

DNA > CLONE #1, FINAL                    DNA Length: 452 nts
Minimum analysis length: 80 amino acids    not starting with ATG 1 open reading frame found.

RF :1
RF :2
RF :3

The DNA Inspector II e          Open Reading Frame Analysis

Analysis of peptide # 1 Reading frame: 3
starts at nt #:  +3
number of amino acids:  92

One letter representation :

```
1  IPILGGITEV KDNDNSVDFD ELAKFAIAEH NKKENAALEF  GKVIEKKQQA  VQGTMYYIKV  EANDGGEKKT
71 YEAKVWVKLW ENFKELQELK LV*  (SEQ ID NO:68)
```

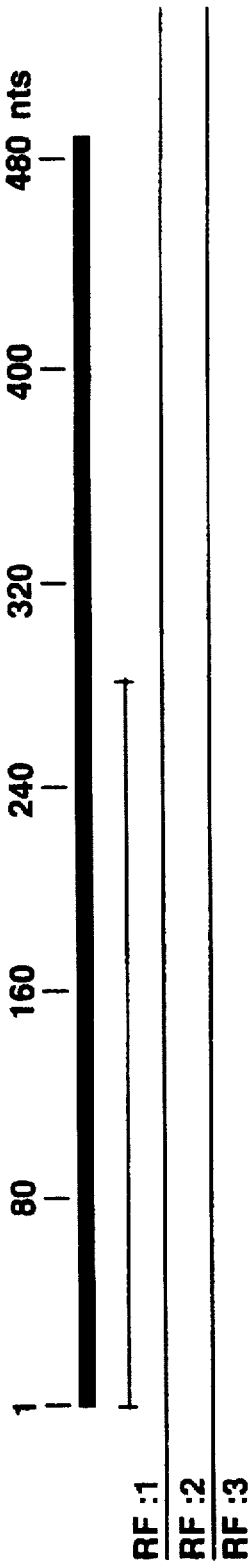

FIG. 9
IPC Clone 5

The DNA Inspector Ile          Open Reading Frame Analysis

DNA > CLONE #5, FINAL                    DNA Length: 488 nts
Minimum analysis length: 80 amino acids    not starting with ATG 1 open reading frame found.

RF :1
RF :2
RF :3

The DNA Inspector Ile          Open Reading Frame Analysis

Analysis of peptide # 1 Reading frame: 1
starts at nt #1:   +1
number of amino acids:  94

One letter representation:

1  EFPILGGITE  VKDNDNSVDF  DELAKFAITE  HNKKENAALE  FGKVIEKKQQ  AVQGTMYYIK  AEANDGGEKK
71 TYEAKVWVKL  WENFKEFARN  SNLV*     (SEQ ID NO:69)

FIG.10
IPC Clone 6

The DNA Inspector I I e      Open Reading Frame Analysis

DNA > #6, FINAL      DNA Length: 855 nts not starting with ATG
Minimum analysis length: 80 amino acids 1 open reading frame found.

RF :1
RF :2
RF :3

The DNA Inspector I I e      Open Reading Frame Analysis

Analysis of peptide # 1 Reading frame: 2
starts at nt #: +311
number of amino acids: 99

One letter representation :

```
 1  EKKTYEAKVW VKPWENFKEF          VDEHNKKQNT LLEFKKVLNT KEQVVAGIMY YITLEATDGG
71                                 (SEQ ID NO:70)
```

```
************************************************
*  TRANSLATION OF A NUCLEIC ACID SEQUENCE       *
************************************************
Done on DNA sequence AMB_A_IA.

DE    SEQUENCE OF AMB A IA CLONE.
```

FIG.11A

```
Total number of bases is: 1196.
Analysis done on the complete sequence.
Done on (absolute) phase(s): 1.
Using the Universal genetic code.
```

---

```
         10        20        30        40        50        60
          |         |         |         |         |         |
    TTGTATTTTACCTTAGCCCTTGTCACTTTGCTGCAACCTGTTCGTTCTGCCGAAGATCTC
      L  Y  F  T  L  A  L  V  T  L  L  Q  P  V  R  S  A  E  D  L 70        80        90       100       110       120
          |         |         |         |         |         |
    CAGGAAATCTTACCAGTTAACGAAACAAGGAGGCTGACAACAAGTGGAGCATACAACATT
      Q  E  I  L  P  V  N  E  T  R  R  L  T  T  S  G  A  Y  N  I 130       140       150       160       170       180
          |         |         |         |         |         |
    ATAGACGGGTGCTGGAGGGGCAAAGCCGATTGGGCGGAAAACCGAAAAGCGTTAGCCGAT
      I  D  G  C  W  R  G  K  A  D  W  A  E  N  R  K  A  L  A  D 190       200       210       220       230       240
          |         |         |         |         |         |
    TGTGCCCAAGGTTTTGGGAAGGGAACAGTGGGCGGAAAAGATGGTGATATATACACGGTC
      C  A  Q  G  F  G  K  G  T  V  G  G  K  D  G  D  I  Y  T  V 250       260       270       280       290       300
          |         |         |         |         |         |
    ACCAGTGAGCTAGATGATGATGTTGCAAATCCAAAAGAAGGCACACTCCGGTTTGGTGCC
      T  S  E  L  D  D  D  V  A  N  P  K  E  G  T  L  R  F  G  A 310       320       330       340       350       360
          |         |         |         |         |         |
    GCCCAAAACAGGCCCTTGTGGATCATTTTTGAAAGAGATATGGTGATTCGTTTGGATAAA
      A  Q  N  R  P  L  W  I  I  F  E  R  D  M  V  I  R  L  D  K 370       380       390       400       410       420
          |         |         |         |         |         |
    GAGATGGTGGTAAACAGTGACAAGACCATCGATGGCCGAGGGGCGAAAGTTGAAATCATT
      E  M  V  V  N  S  D  K  T  I  D  G  R  G  A  K  V  E  I  I
```

FIG.11B

```
             430       440       450       460       470       480
              |         |         |         |         |         |
     AACGCTGGTTTCACCCTTAATGGTGTCAAGAATGTAATCATTCATAACATAAATATGCAT
      N  A  G  F  T  L  N  G  V  K  N  V  I  I  H  N  I  N  M  H 490       500       510       520       530       540
              |         |         |         |         |         |
     GATGTTAAAGTGAATCCAGGAGGCCTGATTAAGTCCAACGATGGTCCAGCAGCTCCAAGA
      D  V  K  V  N  P  G  G  L  I  K  S  N  D  G  P  A  A  P  R 550       560       570       580       590       600
              |         |         |         |         |         |
     GCTGGTAGTGATGGTGATGCTATAAGTATTTCTGGTAGTTCACAAATATGGATCGACCAT
      A  G  S  D  G  D  A  I  S  I  S  G  S  S  Q  I  W  I  D  H 610       620       630       640       650       660
              |         |         |         |         |         |
     TGTTCGCTCAGTAAGTCTGTTGATGGGCTGGTAGATGCCAAGCTCGGCACCACACGCTTA
      C  S  L  S  K  S  V  D  G  L  V  D  A  K  L  G  T  T  R  L 670       680       690       700       710       720
              |         |         |         |         |         |
     ACCGTTTCCAACAGCTTATTCACCCAACACCAGTTTGTACTATTATTCGGGGCTGGTGAC
      T  V  S  N  S  L  F  T  Q  H  Q  F  V  L  L  F  G  A  G  D 730       740       750       760       770       780
              |         |         |         |         |         |
     GAAAATATTGAAGATAGAGGCATGCTAGCAACGGTCGCTTTCAACACGTTCACTGATAAC
      E  N  I  E  D  R  G  M  L  A  T  V  A  F  N  T  F  T  D  N 790       800       810       820       830       840
              |         |         |         |         |         |
     GTTGACCAAAGAATGCCTAGATGTCGACATGGGTTTTTCCAAGTCGTTAACAACAACTAT
      V  D  Q  R  M  P  R  C  R  H  G  F  F  Q  V  V  N  N  N  Y 850       860       870       880       890       900
              |         |         |         |         |         |
     GATAAATGGGGATCGTATGCCATCGGTGGTAGCGCGTCCCCAACCATACTCAGCCAAGGG
      D  K  W  G  S  Y  A  I  G  G  S  A  S  P  T  I  L  S  Q  G 910       920       930       940       950       960
              |         |         |         |         |         |
     AACAGATTCTGCGCCCCCGATGAACGCAGCAAGAAAAATGTCCTAGGAAGGCATGGTGAA
      N  R  F  C  A  P  D  E  R  S  K  K  N  V  L  G  R  H  G  E
```

FIG.11C

```
       970         980         990        1000        1010        1020
        |           |           |           |           |           |
GCCGCCCGAGAGTCGATGAAGTGGAAGAACGAATAAAGACCTGCTTGAAATGGT
 A  A  A  E  S  M  K  W  K  N  W  R  T  N  K  D  V  L  E  N  G 1030        1040        1050        1060        1070        1080
        |           |           |           |           |           |
GCTATTTTTGTTGCATCCGGGGTCGATCCAGTGCTAACCCCTGAGCAAAGCGCAGGGATG
 A  I  F  V  A  S  G  V  D  P  V  L  T  P  E  Q  S  A  G  M 1090        1100        1110        1120        1130        1140
        |           |           |           |           |           |
ATTCCAGCCGAACCAGGAGAGTCCCGCTCTAAGCCTCACTAGTAGTGCTGGTGTACTCTCA
 I  P  A  E  P  G  E  S  A  L  S  L  T  S  S  A  G  V  L  S 1150        1160        1170        1180        1190
        |           |           |           |           |
TGCCAACCCGGAGCACTTGCTAAGCACCGACCAATTACTAAGCACTTATAATGA  (SEQ. ID NO:71)
 C  Q  P  G  A  P  C  -  A  P  D  Q  L  L  S  T  Y  N      (SEQ. ID NO:72)
```

```
************************************************
* TRANSLATION OF A NUCLEIC ACID SEQUENCE *
************************************************
Done on DNA sequence AMB_A_IB.

DE    SEQUENCE OF AMB A IB CLONE.
```

FIG.12A

```
Total number of bases is: 1349.
Analysis done on the complete sequence.
Done on (absolute) phase(s): 1.
Using the Universal genetic code.
```

---

```
         10        20        30        40        50        60
          |         |         |         |         |         |
    ATGGGGATCAAACACTGTTGTTACATCTTGTATTTTACCTTAGCCCTTGTCACTTTGCTG
     M  G  I  K  H  C  C  Y  I  L  Y  F  T  L  A  L  V  T  L  L 70        80        90       100       110       120
          |         |         |         |         |         |
    CAACCTGTTCGTTCTGCAGAAGATGTTGAAGAATTCTTACCTTCAGCTAACGAAACAAGG
     Q  P  V  R  S  A  E  D  V  E  E  F  L  P  S  A  N  E  T  R 130       140       150       160       170       180
          |         |         |         |         |         |
    AGGAGCCTGAAAGCATGTGAAGCACACAACATTATAGACAAGTGCTGGAGGTGCAAAGCC
     R  S  L  K  A  C  E  A  H  N  I  I  D  K  C  W  R  C  K  A 190       200       210       220       230       240
          |         |         |         |         |         |
    GATTGGGCGAATAACCGACAAGCGTTAGCCGATTGTGCCCAAGGTTTTGCAAAGGGAACC
     D  W  A  N  N  R  Q  A  L  A  D  C  A  Q  G  F  A  K  G  T 250       260       270       280       290       300
          |         |         |         |         |         |
    TACGGTGGAAAACATGGTGATGTCTACACGGTCACCAGTGATAAAGATGATGATGTTGCA
     Y  G  G  K  H  G  D  V  Y  T  V  T  S  D  K  D  D  D  V  A 310       320       330       340       350       360
          |         |         |         |         |         |
    AATCCAAAAGAAGGCACACTCCGGTTTGCTGCTGCCCAAAACAGGCCCTTGTGGATCATT
     N  P  K  E  G  T  L  R  F  A  A  A  Q  N  R  P  L  W  I  I 370       380       390       400       410       420
          |         |         |         |         |         |
    TTTAAAAGAAATATGGTGATTCATTTGAATCAAGAGCTTGTCGTAAACAGCGACAAGACC
     F  K  R  N  M  V  I  H  L  N  Q  E  L  V  V  N  S  D  K  T
```

FIG.12B

```
         430       440       450       460       470       480
          |         |         |         |         |         |
ATCGATGGCCGAGGGGTGAAAGTTAACATCGTTAACGCCGGTCTCACCCTCATGAATGTC
  I D G R G V K V N I V N A G L T L M N V 490       500       510       520       530       540
          |         |         |         |         |         |
AAGAATATAATCATTCATAACATAAATATCCATGATATTAAAGTTTGTCCAGGAGGCATG
  K N I I I H N I N I H D I K V C P G G M 550       560       570       580       590       600
          |         |         |         |         |         |
ATTAAGTCCAACGATGGTCCACCAATTTTAAGACAACAAAGTGATGGTGATGCTATAAAT
  I K S N D G P P I L R Q Q S D G D A I N 610       620       630       640       650       660
          |         |         |         |         |         |
GTTGCTGGTAGTTCACAAATATGGATCGACCATTGCTCGCTCAGTAAGGCTTCCGATGGG
  V A G S S Q I W I D H C S L S K A S D G 670       680       690       700       710       720
          |         |         |         |         |         |
CTGCTCGATATCACCCTCGGCAGCTCACACGTGACCGTTTCCAACTGCAAATTCACCCAA
  L L D I T L G S S H V T V S N C K F T Q 730       740       750       760       770       780
          |         |         |         |         |         |
CACCAATTTGTATTATTGCTCGGGGCTGATGACACCCATTATCAAGATAAAGGCATGCTA
  H Q F V L L L G A D D T H Y Q D K G M L 790       800       810       820       830       840
          |         |         |         |         |         |
GCAACGGTAGCATTCAACATGTTCACCGATCACGTTGACCAAAGAATGCCTAGATGTAGA
  A T V A F N M F T D H V D Q R M P R C R 850       860       870       880       890       900
          |         |         |         |         |         |
TTTGGGTTTTTCCAAGTCGTTAACAACAACTACGACAGATGGGGAACGTACGCCATCGGT
  F G F F Q V V N N N Y D R W G T Y A I G 910       920       930       940       950       960
          |         |         |         |         |         |
GGTAGCTCGGCCCCAACTATACTCAGCCAAGGGAACAGATTCTTCGCCCCCGATGATATC
  G S S A P T I L S Q G N R F F A P D D I
```

FIG.12C

```
          970       980       990      1000      1010      1020
           |         |         |         |         |         |
    ATCAAGAAAAATGTCTTAGCGAGGACTGGTACTGGCAACGCAGAGTCGATGTCGTGGAAC
     I  K  K  N  V  L  A  R  T  G  T  G  N  A  E  S  M  S  W  N 1030      1040      1050      1060      1070      1080
           |         |         |         |         |         |
    TGGAGAACAGATAGAGACTTGCTTGAAAATGGTGCTATTTTTCTCCCATCCGGGTCTGAT
     W  R  T  D  R  D  L  L  E  N  G  A  I  F  L  P  S  G  S  D 1090      1100      1110      1120      1130      1140
           |         |         |         |         |         |
    CCAGTGCTAACCCCTGAGCAAAAAGCAGGGATGATTCCAGCTGAACCAGGAGAAGCCGTT
     P  V  L  T  P  E  Q  K  A  G  M  I  P  A  E  P  G  E  A  V 1150      1160      1170      1180      1190      1200
           |         |         |         |         |         |
    CTAAGACTCACTAGTAGTGCTGGTGTACTCTCATGCCATCAAGGAGCACCTTGCTAAGCA
     L  R  L  T  S  S  A  G  V  L  S  C  H  Q  G  A  P  -  A 1210      1220      1230      1240      1250      1260
           |         |         |         |         |         |
    CCTGGCCAATTCCTAAGCTTTTATAATAATCATAAATACTTATTTTATTTTATTTTTGAT
     P  G  Q  F  L  S  F  Y  N  N  H  K  Y  L  F  Y  F  I  F  D 1270      1280      1290      1300      1310      1320
           |         |         |         |         |         |
    ATTTTATATGAACCATTACGTTCAAGTACTCTATTAACATGTTTTAAATTCATAAGAGTT
     I  L  Y  E  P  L  R  S  S  T  L  L  T  C  F  K  F  I  R  V 1330      1340
           |         |
    TATTGATAAAAAAAAAAAAAAACCGAATTC     (SEQ. ID NO:73)
     Y  -  -  K  K  K  K  K  P  N     (SEQ. ID NO:74)
```

```
************************************************
* TRANSLATION OF A NUCLEIC ACID SEQUENCE *
************************************************
Done on DNA sequence AMB_A_IC.

DE   SEQUENCE OF AMB A IC CLONE.
```

FIG.13A

```
Total number of bases is: 1320.
Analysis done on the complete sequence.
Done on (absolute) phase(s): 1.
Using the Universal genetic code.
```

---

```
          10        20        30        40        50        60
           |         |         |         |         |         |
     ATGGGGATCAAACAATGTTGTTACATCTTGTATTTTACCTTAGCACTTGTCGCTTTGCTG
      M  G  I  K  Q  C  C  Y  I  L  Y  F  T  L  A  L  V  A  L  L 70        80        90       100       110       120
           |         |         |         |         |         |
     CAACCTGTTCGTTCTGCCGAAGGTGTCGGGGAAATCTTACCTTCAGTTAACGAAACGAGG
      Q  P  V  R  S  A  E  G  V  G  E  I  L  P  S  V  N  E  T  R 130       140       150       160       170       180
           |         |         |         |         |         |
     AGCCTGCAAGCATGTGAAGCACTCAACATTATAGACAAGTGCTGGAGGGGCAAAGCCGAT
      S  L  Q  A  C  E  A  L  N  I  I  D  K  C  W  R  G  K  A  D 190       200       210       220       230       240
           |         |         |         |         |         |
     TGGGAGAACAACCGACAAGCGTTAGCCGACTGTGCCCAAGGTTTTGCAAAGGGAACCTAC
      W  E  N  N  R  Q  A  L  A  D  C  A  Q  G  F  A  K  G  T  Y 250       260       270       280       290       300
           |         |         |         |         |         |
     GGCGGAAAATGGGGTGATGTCTACACGGTCACCAGCAATCTAGATGATGATGTTGCAAAT
      G  G  K  W  G  D  V  Y  T  V  T  S  N  L  D  D  D  V  A  N 310       320       330       340       350       360
           |         |         |         |         |         |
     CCAAAAGAAGGCACACTCCGGTTTGCTGCCGCCCAAAACAGGCCCTTGTGGATCATTTTT
      P  K  E  G  T  L  R  F  A  A  A  Q  N  R  P  L  W  I  I  F 370       380       390       400       410       420
           |         |         |         |         |         |
     AAAAATGATATGGTGATTAATTTGAATCAAGAGCTTGTCGTAAACAGCGACAAGACCATC
      K  N  D  M  V  I  N  L  N  Q  E  L  V  V  N  S  D  K  T  I
```

FIG. 13B

```
       430       440       450       460       470       480
        |         |         |         |         |         |
GATGGCCGAGGGGTGAAAGTTGAAATCATTAACGGAGGTCTCACCCTCATGAATGTCAAG
 D  G  R  G  V  K  V  E  I  I  N  G  G  L  T  L  M  N  V  K 490       500       510       520       530       540
        |         |         |         |         |         |
AATATAATCATTCATAACATAAATATCCATGATGTTAAAGTGCTTCCAGGAGGCATGATT
 N  I  I  I  H  N  I  N  I  H  D  V  K  V  L  P  G  G  M  I 550       560       570       580       590       600
        |         |         |         |         |         |
AAGTCCAACGATGGTCCACCAATTTTAAGACAAGCAAGTGATGGGGATACTATAAATGTT
 K  S  N  D  G  P  P  I  L  R  Q  A  S  D  G  D  T  I  N  V 610       620       630       640       650       660
        |         |         |         |         |         |
GCTGGTAGTTCCCAAATATGGATAGACCATTGCTCACTCAGCAAGTCTTTCGATGGGCTG
 A  G  S  S  Q  I  W  I  D  H  C  S  L  S  K  S  F  D  G  L 670       680       690       700       710       720
        |         |         |         |         |         |
GTCGATGTCACCCTCGGTAGCACACACGTGACCATTTCCAACTGCAAATTCACCCAACAG
 V  D  V  T  L  G  S  T  H  V  T  I  S  N  C  K  F  T  Q  Q 730       740       750       760       770       780
        |         |         |         |         |         |
TCAAAAGCAATATTGTTGGGAGCAGATGACACCCATGTTCAAGATAAAGGAATGCTAGCA
 S  K  A  I  L  L  G  A  D  D  T  H  V  Q  D  K  G  M  L  A 790       800       810       820       830       840
        |         |         |         |         |         |
ACGGTCGCTTTCAACATGTTCACCGATAACGTTGACCAAAGAATGCCTAGATGTCGATTT
 T  V  A  F  N  M  F  T  D  N  V  D  Q  R  M  P  R  C  R  F 850       860       870       880       890       900
        |         |         |         |         |         |
GGGTTTTTCCAAGTTGTTAACAACAACTACGACAGATGGGGAACGTACGCCATAGGTGGT
 G  F  F  Q  V  V  N  N  N  Y  D  R  W  G  T  Y  A  I  G  G 910       920       930       940       950       960
        |         |         |         |         |         |
AGCTCGGCCCCAACTATACTCTGCCAAGGGAACAGATTCTTGGCCCCTGATGATCAGATC
 S  S  A  P  T  I  L  C  Q  G  N  R  F  L  A  P  D  D  Q  I
```

FIG. 13C

```
        970         980         990         1000        1010        1020
         |           |           |           |           |           |
AAGAAAAATGTCCTAGGAGGACTGGTACAGGGCGGCTGCTGAGTCGATGGCGTGGAACTGG
 K  K  N  V  L  A  R  T  G  T  G  A  A  E  E  S  M  A  W  N  W 1030        1040        1050        1060        1070        1080
         |           |           |           |           |           |
AGATCTGATAAAGACTTGCTTGAAAATGGTGCTATTTTTGTTACATCTGGGTCTGATCCA
 R  S  D  K  D  L  L  E  N  G  A  I  F  V  T  S  G  S  D  P 1090        1100        1110        1120        1130        1140
         |           |           |           |           |           |
GTGCTAACCCCTGTTCAAAGGCCAGGATGATTCCAGCTGAACCAGGAGAAGCCGCTATA
 V  L  T  P  V  Q  S  A  G  M  I  P  A  E  P  G  E  E  A  A  I 1150        1160        1170        1180        1190        1200
         |           |           |           |           |           |
AAACTCACTAGTAGTGCTGGTGTATTCTCATGCCGTCCTGGAGCACCTTGCTAAGCACCC
 K  L  T  S  S  A  G  V  F  S  C  R  P  G  A  P  C  -  A  P 1210        1220        1230        1240        1250        1260
         |           |           |           |           |           |
TGCCAATTCTCCTAAGCTTTTGCAATGATCAAAAATACTTTTTATTTTTATTTTTAATAT
 C  Q  F  S  -  A  F  A  M  I  K  N  T  F  L  F  Y  F  -  Y 1270        1280        1290        1300        1310        1320
         |           |           |           |           |           |
TTTATATGTACTGGAAATGAACCATTACCTTCTAGTACTCTATAAACATGTTTTGCATTTA
 F  I  C  T  G  N  E  P  L  P  S  S  T  L  -  H  V  L  H  L
```

(SEQ. ID NO:75)
(SEQ. ID NO:76)

```
*******************************************
* TRANSLATION OF A NUCLEIC ACID SEQUENCE *
*******************************************
Done on DNA sequence AMB_A_ID.

DE    SEQUENCE OF AMB A ID CLONE.
```

FIG.14A

```
Total number of bases is: 1160.
Analysis done on the complete sequence.
Done on (absolute) phase(s): 1.
Using the Universal genetic code.
```

```
             10        20        30        40        50        60
              |         |         |         |         |         |
        TTGTATTTTACCTTAGCCCTTGTCACTTTGCTGCAACCTGTTCGTTCTGCCGAAGATCTC
         L  Y  F  T  L  A  L  V  T  L  L  Q  P  V  R  S  A  E  D  L 70        80        90       100       110       120
              |         |         |         |         |         |
        CAGGAAATCTTACCTTCAGCTAACGAAACAAGGAGCCTGACAACATGTGGAACATACAAC
         Q  E  I  L  P  S  A  N  E  T  R  S  L  T  T  C  G  T  Y  N 130       140       150       160       170       180
              |         |         |         |         |         |
        ATTATAGACGGGTGCTGGAGGGGCAAAGCCGATTGGGCGGAAAACCGAAAAGCGTTAGCC
         I  I  D  G  C  W  R  G  K  A  D  W  A  E  N  R  K  A  L  A 190       200       210       220       230       240
              |         |         |         |         |         |
        GATTGTGCCCAAGGTTTTGCAAAGGGAACAATCGGCGGAAAAGATGGTGATATATACACG
         D  C  A  Q  G  F  A  K  G  T  I  G  G  K  D  G  D  I  Y  T 250       260       270       280       290       300
              |         |         |         |         |         |
        GTCACCAGTGAGCTAGATGATGATGTTGCAAATCCAAAAGAAGGCACACTCCGGTTTGGT
         V  T  S  E  L  D  D  D  V  A  N  P  K  E  G  T  L  R  F  G 310       320       330       340       350       360
              |         |         |         |         |         |
        GCCGCCCAAAACAGGCCCTTGTGGATTATTTTTGAAAGAGATATGGTGATTCGTTTGGAT
         A  A  Q  N  R  P  L  W  I  I  F  E  R  D  M  V  I  R  L  D 370       380       390       400       410       420
              |         |         |         |         |         |
        AGAGAGTTGGCTATAAACAACGACAAGACCATCGATGGCCGAGGGGCGAAAGTTGAAATC
         R  E  L  A  I  N  N  D  K  T  I  D  G  R  G  A  K  V  E  I
```

FIG. 14B

```
           430       440       450       460       470       480
            |         |         |         |         |         |
        ATTAACGCTGGTTTCGCCATCTATAATGTCAAGAATATAATCATTCATAACATAATTATG
         I  N  A  G  F  A  I  Y  N  V  K  N  I  I  I  H  N  I  I  M 490       500       510       520       530       540
            |         |         |         |         |         |
        CATGATATTGTAGTGAATCCAGGAGGCCTGATTAAGTCCCACGATGGTCCACCAGTTCCA
         H  D  I  V  V  N  P  G  G  L  I  K  S  H  D  G  P  P  V  P 550       560       570       580       590       600
            |         |         |         |         |         |
        AGAAAGGGTAGTGATGGTGATGCTATAGGTATTTCTGGTGGTTCACAAATATGGATCGAC
         R  K  G  S  D  G  D  A  I  G  I  S  G  G  S  Q  I  W  I  D 610       620       630       640       650       660
            |         |         |         |         |         |
        CATTGCTCCCTCAGTAAGGCTGTTGATGGGCTAATCGATGCTAAACACGGCAGCACACAC
         H  C  S  L  S  K  A  V  D  G  L  I  D  A  K  H  G  S  T  H 670       680       690       700       710       720
            |         |         |         |         |         |
        TTCACCGTTTCTAACTGCTTATTCACCCAACACCAATATTTATTATTGTTCTGGGATTTT
         F  T  V  S  N  C  L  F  T  Q  H  Q  Y  L  L  L  F  W  D  F 730       740       750       760       770       780
            |         |         |         |         |         |
        GACGAGCGAGGCATGCTATGTACGGTCGCATTCAACAAGTTCACTGATAACGTTGACCAA
         D  E  R  G  M  L  C  T  V  A  F  N  K  F  T  D  N  V  D  Q 790       800       810       820       830       840
            |         |         |         |         |         |
        AGAATGCCTAACTTACGACATGGGTTTGTCCAAGTCGTTAACAACAACTACGAAAGATGG
         R  M  P  N  L  R  H  G  F  V  Q  V  V  N  N  N  Y  E  R  W 850       860       870       880       890       900
            |         |         |         |         |         |
        GGATCGTACGCCCTCGGTGGTAGCGCAGGCCCAACCATACTTAGCCAAGGGAACAGATTC
         G  S  Y  A  L  G  G  S  A  G  P  T  I  L  S  Q  G  N  R  F 910       920       930       940       950       960
            |         |         |         |         |         |
        TTAGCCTCCGATATCAAGAAAGAGGTCGTAGGGAGGTATGGTGAATCCGCCATGTCAGAG
         L  A  S  D  I  K  K  E  V  V  G  R  Y  G  E  S  A  M  S  E
```

FIG. 14C

```
       970         980         990         1000        1010        1020
        |           |           |           |           |           |
TCGATTAATTGGAACTGGAGATCGTATATGGACGTATATTTGAAAATGTGCTATTTTGTT
 S  I  N  W  R  S  Y  M  D  V  F  E  N  G  A  I  F  V 1030        1040        1050        1060        1070        1080
        |           |           |           |           |           |
CCATCCGGGGTTGATCCAGTGCTAACCCCTGAGCAAAACCGCAGGGATGATTCCAGCCCGAA
 P  S  G  V  D  P  V  L  T  P  E  Q  N  A  G  M  I  P  A  E 1090        1100        1110        1120        1130        1140
        |           |           |           |           |           |
CCAGGAGAAGCCGTTCTAAGACTCACTAGTAGTGCTGGTGTCCTCTCATGCCAACCTGGA
 P  G  E  A  V  L  R  L  T  S  S  A  G  V  L  S  C  Q  P  G 1150        1160
        |           |
GCACCCTTGCTAAGCACTGCA          (SEQ. ID NO:77)
 A  P  C  -  A  L              (SEQ. ID NO:78)
```

```
***********************************************
* TRANSLATION OF A NUCLEIC ACID SEQUENCE *
***********************************************
Done on DNA sequence AMB_A_II.

DE    SEQUENCE OF AMB A II CLONE.
```

FIG.15A

```
Total number of bases is: 1368.
Analysis done on the complete sequence.
Done on (absolute) phase(s): 1.
Using the Universal genetic code.
```

---

```
          10        20        30        40        50        60
           |         |         |         |         |         |
      TTGTATTTTACCTTAGCACTTGTCACTTTGGTGCAAGCTGGACGTCTTGGCGAAGAGGTC
        L  Y  F  T  L  A  L  V  T  L  V  Q  A  G  R  L  G  E  E  V 70        80        90       100       110       120
           |         |         |         |         |         |
      GACATCTTACCTTCACCTAACGATACAAGGAGGAGCCTGCAAGGATGTGAAGCACACAAC
        D  I  L  P  S  P  N  D  T  R  R  S  L  Q  G  C  E  A  H  N 130       140       150       160       170       180
           |         |         |         |         |         |
      ATTATAGACAAGTGTTGGAGGTGCAAACCCGATTGGGCGGAGAACCGACAAGCGTTAGGC
        I  I  D  K  C  W  R  C  K  P  D  W  A  E  N  R  Q  A  L  G 190       200       210       220       230       240
           |         |         |         |         |         |
      GATTGTGCGCAAGGTTTTGGAAAGGCAACTCACGGCGGAAAATGGGGTGATATCTACATG
        D  C  A  Q  G  F  G  K  A  T  H  G  G  K  W  G  D  I  Y  M 250       260       270       280       290       300
           |         |         |         |         |         |
      GTCACAAGTGATCAGGATGATGATGTTGTAAATCCAAAAGAAGGCACACTCCGGTTCGGT
        V  T  S  D  Q  D  D  D  V  V  N  P  K  E  G  T  L  R  F  G 310       320       330       340       350       360
           |         |         |         |         |         |
      GCTACCCAGGACAGGCCCTTGTGGATCATTTTTCAAAGAGATATGATTATTTATTTGCAA
        A  T  Q  D  R  P  L  W  I  I  F  Q  R  D  M  I  I  Y  L  Q 370       380       390       400       410       420
           |         |         |         |         |         |
      CAAGAGATGGTCGTAACCAGCGACACGACCATTGATGGTCGAGGGGCGAAAGTTGAGCTC
        Q  E  M  V  V  T  S  D  T  T  I  D  G  R  G  A  K  V  E  L
```

FIG. 15B

```
         430       440       450       460       470       480
          |         |         |         |         |         |
      GTTTATGGAGGTATCACCCTCATGAATGTCAAGAATGTAATCATTCACAACATAGATATC
       V   Y   G   G   I   T   L   M   N   V   K   N   V   I   I   H   N   I   D   I 490       500       510       520       530       540
          |         |         |         |         |         |
      CATGATGTTAGAGTGCTTCCAGGAGGTAGGATTAAGTCCAATGGTGGTCCAGCCATACCA
       H   D   V   R   V   L   P   G   G   R   I   K   S   N   G   G   P   A   I   P 550       560       570       580       590       600
          |         |         |         |         |         |
      AGACATCAGAGTGATGGTGATGCTATCCATGTTACGGGTAGTTCAGACATATGGATCGAC
       R   H   Q   S   D   G   D   A   I   H   V   T   G   S   S   D   I   W   I   D 610       620       630       640       650       660
          |         |         |         |         |         |
      CATTGCACGCTCAGTAAGTCATTTGATGGGCTCGTCGATGTCAACTGGGGCAGCACAGGA
       H   C   T   L   S   K   S   F   D   G   L   V   D   V   N   W   G   S   T   G 670       680       690       700       710       720
          |         |         |         |         |         |
      GTAACCATTTCCAACTGCAAATTCACCCACCACGAAAAAGCTGTTTTGCTCGGGCTAGT
       V   T   I   S   N   C   K   F   T   H   H   E   K   A   V   L   L   G   A   S 730       740       750       760       770       780
          |         |         |         |         |         |
      GACACGCATTTTCAAGATCTGAAAATGCATGTAACGCTTGCATACAACATCTTCACCAAT
       D   T   H   F   Q   D   L   K   M   H   V   T   L   A   Y   N   I   F   T   N 790       800       810       820       830       840
          |         |         |         |         |         |
      ACCGTTCACGAAAGAATGCCCAGATGCCGATTTGGGTTTTTCCAAATCGTTAACAACTTC
       T   V   H   E   R   M   P   R   C   R   F   G   F   F   Q   I   V   N   N   F 850       860       870       880       890       900
          |         |         |         |         |         |
      TACGACAGATGGGATAAGTACGCCATCGGTGGTAGCTCGAACCCTACTATTCTCAGCCAA
       Y   D   R   W   D   K   Y   A   I   G   G   S   S   N   P   T   I   L   S   Q 910       920       930       940       950       960
          |         |         |         |         |         |
      GGGAACAAATTCGTGGCCCCCGATTTCATTTACAAGAAAAACGTCTGTCTAAGGACTGGT
       G   N   K   F   V   A   P   D   F   I   Y   K   K   N   V   C   L   R   T   G
```

FIG. 15C

```
            970       980       990      1000      1010      1020
             |         |         |         |         |         |
       GCACAGGAGCCAGAATGGATGACTTGGAACTGGAGAACACAAAACGACGTGCTTGAAAAT
         A  Q  E  P  E  W  M  T  W  N  W  R  T  Q  N  D  V  L  E  N 1030      1040      1050      1060      1070      1080
             |         |         |         |         |         |
       GGTGCTATCTTTGTGGCATCTGGGTCTGATCCAGTGCTAACCGCTGAACAAAATGCAGGC
         G  A  I  F  V  A  S  G  S  D  P  V  L  T  A  E  Q  N  A  G 1090      1100      1110      1120      1130      1140
             |         |         |         |         |         |
       ATGATGCAAGCTGAACCGGGAGATATGGTTCCACAACTCACCATGAATGCAGGTGTACTC
         M  M  Q  A  E  P  G  D  M  V  P  Q  L  T  M  N  A  G  V  L 1150      1160      1170      1180      1190      1200
             |         |         |         |         |         |
       ACATGCTCGCCTGGAGCACCTTGCTAAGCACCTGGCCAATTCCTATGCAACGATCATAAA
         T  C  S  P  G  A  P  C  -  A  P  G  Q  F  L  C  N  D  H  K 1210      1220      1230      1240      1250      1260
             |         |         |         |         |         |
       TACTTGCTCACCATAAGTGTTCATTTGATTAGATTTGGACACGAATGATGTAACCGATTC
         Y  L  L  T  I  S  V  H  L  I  R  F  G  H  E  -  C  N  R  F 1270      1280      1290      1300      1310      1320
             |         |         |         |         |         |
       GTCTGAATTATGATTTGTTTTGATTCTCAGTTTCATAATATGGCTTCTTGAGAGCAAAAT
         V  -  I  M  I  C  F  D  S  Q  F  H  N  M  A  S  -  E  Q  N 1330      1340      1350      1360
             |         |         |         |
       TAGAGAAGAGTGTCTTTGATCAACTACATTTTATGGTTTTTATATTAA   (SEQ. ID NO:79)
         -  R  R  V  S  L  I  N  Y  I  L  W  F  L  Y  -  (SEQ. ID NO:80)
```

FIG. 16A

COMPOSITE Amb a I and a II SEQUENCES RELATIVE TO Amb a IA

FIG. 16B

Sample Loaded
1- Pollen Extract
2- JM 109
3- Amb a I A
4- Amb a I B
5- Amb a I C
6- Amb a II A ALLERGIC PATIENT No. 295

1- POLLEN EXTRACT
2- JM109
3- Amb a I B
4- Amb a I A(t)
5- Amb a I A
6- Amb a II
7- Amb a I C

NUCLEIC ACIDS ENCODING ALLERGENIC PROTEINS FROM RAGWEED

RELATED APPLICATION

This application is a divisional of U.S. Ser. No. 07/529,951 filed on May 29, 1990, now abandoned, which is a continuation-in-part of U.S. Ser. No. 07/325,365 filed on Mar. 17, 1989; now abandoned; the disclosures of all of which are hereby incorporated by reference.

FUNDING

Work described herein was supported by the National Institutes of Health (Grant No. AI14908).

BACKGROUND OF THE INVENTION

Genetically predisposed individuals, who make up about 10% of the population, become hypersensitized (allergic) to antigens from a variety of environmental sources to which they are exposed. Those antigens that can induce immediate and/or delayed types of hypersensitivity in people are called allergens. King, T. P., *Adv. Immun.*, 23: 77–105 (1976). Anaphylaxis or atopy, which includes the symptoms of hay fever, asthma and hives, is one form of immediate allergy. It can be caused by a variety of atopic allergens, such as products of grasses, trees, weeds, animal dander, insects, and food, drugs and chemicals.

The antibodies involved in atopic allergy belong primarily to the IgE class of immunoglobulins. IgE binds to mast cells and basophils. Upon combination of a specific allergen with IgE bound to mast cells, the IgE is cross-linked on the cell surface, resulting in the physiological effects of IgE-antigen interaction. Degranulation results in release of, among other substances, histamine, heparin, a chemotactic factor for eosinophilic leukocytes and the leukotrienes, C4, D4 and E4, which cause prolonged constriction of bronchial smooth muscle cells. Hood, L. E. et al., *Immunology*, (2nd ed.), pp460–462, The Benjamin/Cumming Publishing Co., Inc. (1984). These released substances are the mediators which result in allergic symptoms caused by combination of IgE with a specific allergen. Through them, the effects of an allergen are manifested. Such effects may be systemic or local in nature, depending on the route by which the antigen entered the body and the pattern of deposition of IgE and mast cells. Local manifestations generally occur on epithelial surfaces at the location at which the allergen entered the body. Systemic effects can include anaphylaxis (anaphylactic shock), which is the result of an IgE-basophil response to circulating (intravascular) antigen.

One allergen of particular concern for many people is Antigen E or Amb a I, a poorly-defined constituent (or group of constituents) which is the major allergenic component(s) of short ragweed (*Ambrosia artemisiifolia l.* or *Ambrosia elatior*) pollen and the major cause of late summer hayfever in North America and Canada. Smith, J. J., et al., *Mol. Immun* 25: 355–364 (1988); King, T. P., et al., *Biochem.*, 3: 458–468 (1964); King, T. P., *Adv. Immun.*, 23: 77–105 (1976). It has been estimated that, on average, as much as 13% of the total serum IgE in ragweed-sensitive individuals is specific for Amb a I. Zeiss, C. R., et al., *J. Immun.*, 110: 414–421 (1973). Amb a I has been claimed to be an acidic, 38,000 molecular weight, non-glycosylated protein which is cleaved during extraction and chromatographic isolation into two non-covalently associated chains: an alpha chain of 26,000 molecular weight and a beta chain of 12,000 molecular weight. Knox, R. B., et al., *Nature*, 255: 1066–1068 (1970); Knox, R. B., and Heslop-Harrison, J., *J. Cell Sci.*, 6: 1–27 (1970); King, T. P., *Adv. Immun.*, 23: 77–105 (1976); King, T. P., et al., *Archs. Biochem. Biophys.*, 212: 127–135 (1981). The two-chain and the single chain forms of Amb a I, which are both highly reactive with IgE, are allergenically and antigenically related. King, T. P., et al., *Biochemistry*, 3: 458–468 (1964). It has been shown, however, that several physical and chemical modifications of Amb a I cause a marked loss of antigen and allergenic activity. King, T. P., et al., *Archs Biochem. Biophys.*, 212: 127–135 (1981); King, T. P., et al., *Immunochemistry*, 11: 83–92 (1974).

Because ragweed pollen is the chief causative agent of late-summer hay fever in the eastern United States and Canada, it has been the subject of more studies by different laboratories than any other pollen allergen. King, T. P., *Adv. Immun.*, 23: 77–105 (1976). Despite extensive study, the immunochemical definition of Amb a I is still far from complete. Smith and co-workers have begun characterization of the epitope structure of Amb a I, using a series of murine monoclonal antibodies raised against purified, native Amb a I. Three non-overlapping, non-repeating antigenic sites were defined (sites A, B, and C) and monoclonal antibodies directed to sites A and B together resulted in inhibition of 80% of human IgE binding to Amb a I. The reactivity of the monoclonal antibodies used was greatly diminished when Amb a I was physically or chemically modified. Olsen, Ph.D. thesis, University of North Carolina, Chapel Hill (1986); Olson, J. R., and Klapper, D. G., *J. Immun.*, 136: 2109–2115 (1986). They indicated that the two sites (A and B) are conformationally dependent epitopes. That is, they are either single structures which lose their conformation during modification or composite structures made up of two or more discontinuous peptides which are proximal in the native allergen but separate once the allergen has been modified. Smith, J. J., et al., *Mol. Immun.*, 25: 355–365 (1988).

Despite the considerable attention ragweed allergens have received, definition or characterization of the structure(s) or component(s) of the allergen responsible for its adverse effects on people is far from complete and current desentization therapy involves treatment with a complex, ill-defined extract of ragweed pollen.

SUMMARY OF THE INVENTION

The present invention relates to allergenic proteins or peptides from ragweed, DNAs encoding all or a portion of such allergenic proteins or peptides; to compositions containing such an allergen(s) or portions of the allergen(s); and to methods of administering the allergen(s) or a portion thereof or a composition which includes the allergen(s) or portions thereof to reduce or prevent the adverse effects that exposure to the allergen normally has on ragweed-sensitive individuals (i.e., to desensitize individuals to the allergen or block the effects of the allergen). The present invention further relates to methods of diagnosing sensitivity to ragweed pollen.

It has now been shown that Antigen E or Amb a I is not a single protein but, rather, a family or families of proteins to which ragweed-sensitive individuals react. In particular, the present invention relates to DNA encoding an amino acid sequence or peptide present in allergenic proteins from ragweed pollen. It relates to DNA encoding all or a portion of the ragweed allergen Amb a I or Antigen E preparation which has been isolated. Such ragweed allergen preparations are heterogeneous in nature and may include, in addition to what is currently referred to as Amb a I or Antigen E, other ragweed components which are allergenic (i.e., cause the typical adverse effects observed in a ragweed-sensitive individual upon exposure to ragweed pollen). These may include, for example, what is referred to in the literature as Antigen K and referred to herein as Amb a II. The present invention also relates to DNAs encoding similar amino acid sequences (i.e., DNA encoding amino acid sequences of allergens) in types of ragweed other than short ragweed, such as giant ragweed and western ragweed.

BRIEF DESCRIPTION OF THE DRAWINGS

FIG. 1A is a schematic representation of screening of an Amb a I or Antigen E preparation, using monoclonal antibodies and oligoprobes.

FIG. 1B is a schematic representation of screening of a ragweed flowerhead λgt10 library. It also illustrates the use of cross-hybridization and polymerase chain reaction (PCR) methods to obtain full-length cDNA clones encoding Amb a I and Amb a II.

FIG. 2 is the nucleotide sequence of the DNA insert of UNC Clone 1 (referred to as Amb a IA), (SEQ ID NO: 56) which was isolated from a λgt11 library by screening with monoclonal antibodies specific for components of an Amb a I preparation.

FIG. 3 is the nucleotide sequence of the DNA insert of UNC Clone 6 (referred to as Amb a IB), (SEQ ID NO: 58) which was isolated from a λgt11 library by screening with monoclonal antibodies specific for components of an Amb a I preparation.

FIG. 4 is the nucleotide sequence of the DNA insert of UNC Clone 15 (referred to as Amb a IC), (SEQ ID NO: 60) which was isolated from a λgt11 library by screening with monoclonal antibodies specific for components of an Amb a I preparation.

FIG. 5 is the nucleotide sequence of the cDNA insert of IPC Clone 1, (SEQ ID NO: 62) which was isolated from a λgt10 CDNA library using an oligonucleotide probe whose sequence was deduced from an amino acid sequence known to be present in the ragweed allergen preparation Amb a I. The location of the sequence from which the sequence of the oligonucleotide probe was deduced is underlined.

FIG. 6 is the nucleotide sequence of the cDNA insert of IPC Clone 5, (SEQ ID NO: 64) which was isolated from a λgt10 cDNA library using an oligonucleotide probe whose sequence was deduced from an amino acid sequence known to be present in the ragweed allergen preparation Amb a I. The location of the sequence from which the sequence of the oligonucleotide probe was deduced is underlined.

FIG. 7 is the nucleotide sequence of the cDNA insert of IPC Clone 6, (SEQ ID NO: 66) which was isolated from a λgt10 cDNA library using an oligonucleotide probe whose sequence was deduced from an amino acid sequence known to be present in the ragweed allergen preparation Amb a I. The location of the sequence from which the sequence of the oligonucleotide probe was deduced is underlined.

FIG. 8 is a schematic representation of open reading frame analysis of the DNA insert of IPC Clone 1.

FIG. 9 is a schematic representation of open reading frame analysis of the DNA insert of IPC Clone 5.

FIG. 10 is a schematic representation of open reading frame analysis of the DNA insert of IPC Clone 6.

FIG. 11 is the nucleotide sequence (SEQ ID NO: 71) and deduced amino acid sequence of a full length Amb a IA clone (related to UNC clone 1) (SEQ ID NO: 72).

FIG. 12 is the nucleotide sequence (SEQ ID NO: 73) and deduced amino acid sequence of a full length Amb a IB clone (related to UNC clone 6) (SEQ ID NO: 74).

FIG. 13 is the nucleotide sequence (SEQ ID NO: 75) and deduced amino acid sequence of a full length Amb a IC clone (related to UNG clone 15) (SEQ ID NO: 76).

FIG. 14 is the nucleotide sequence (SEQ ID NO: 77) and deduced amino acid sequence of a full length Amb a ID clone (SEQ ID NO: 78).

FIG. 15 is the nucleotide sequence (SEQ ID NO: 79) and deduced amino acid sequence of a full length Amb a II clone (SEQ ID NO: 80).

FIG. 16 is the composite amino acid sequences of the Amb a I and Amb a II multigene family showing regions of similarity as well as regions of disagreements.

DETAILED DESCRIPTION OF THE INVENTION

The present invention is based on an investigation of ragweed pollen allergens, particularly the preparation known as Amb a I (or Antigen E) from short ragweed, using several inter-related approaches, each described below. The terms Amb a I and Antigen E are used interchangeably. Such a preparation, obtained from ragweed pollen, is likely to contain other ragweed allergens, such as Antigen K or Amb a II. The possibility that such a preparation does contain other such allergens has been assessed and results demonstrate that this is the case.

Results of work described herein show that Amb a I is not a single protein or peptide but is, in fact, heterogeneous in nature. That is, what is presently referred to as Antigen E (or Amb a I) appears to be a family or families of proteins or to be polymorphic in nature. The work described herein has resulted in identification and isolation of DNAs encoding peptides or amino acid sequences present in a ragweed allergen. As described, full-length cDNAs encoding Amb a IA, Amb a IB, Amb a IC and Amb a ID and Amb a II have been isolated and sequenced. It has also resulted in isolation and purification from an Amb a I preparation of a protein shown to bind human ragweed IgE and to bind rabbit Amb a I antisera produced using a purified Amb a I preparation.

Interrelationships among DNAs and proteins or peptides identified and isolated using the approaches described in the following section have been demonstrated. For ease of presentation, the several approaches used are represented schematically in FIGS. 1A and 1B, to which reference is made in the following discussion.

As a result of the work described herein, DNAs encoding proteins or peptides present in ragweed allergens have been identified and isolated and the amino acid sequence of the encoded product has been deduced. In addition, through the use of monoclonal antibodies specific for Amb a I or Antigen E, a protein has been obtained from an Amb a I preparation. This protein, referred to as affinity purified Amb a I, has been shown to have biological activity (human IgE binding ability and ability to bind rabbit Amb a I antisera) and, thus, is highly likely to be an allergen. It has also been shown to be encoded by a region of the nucleotide sequences present in two of the isolated DNAs.

Figure 1A:
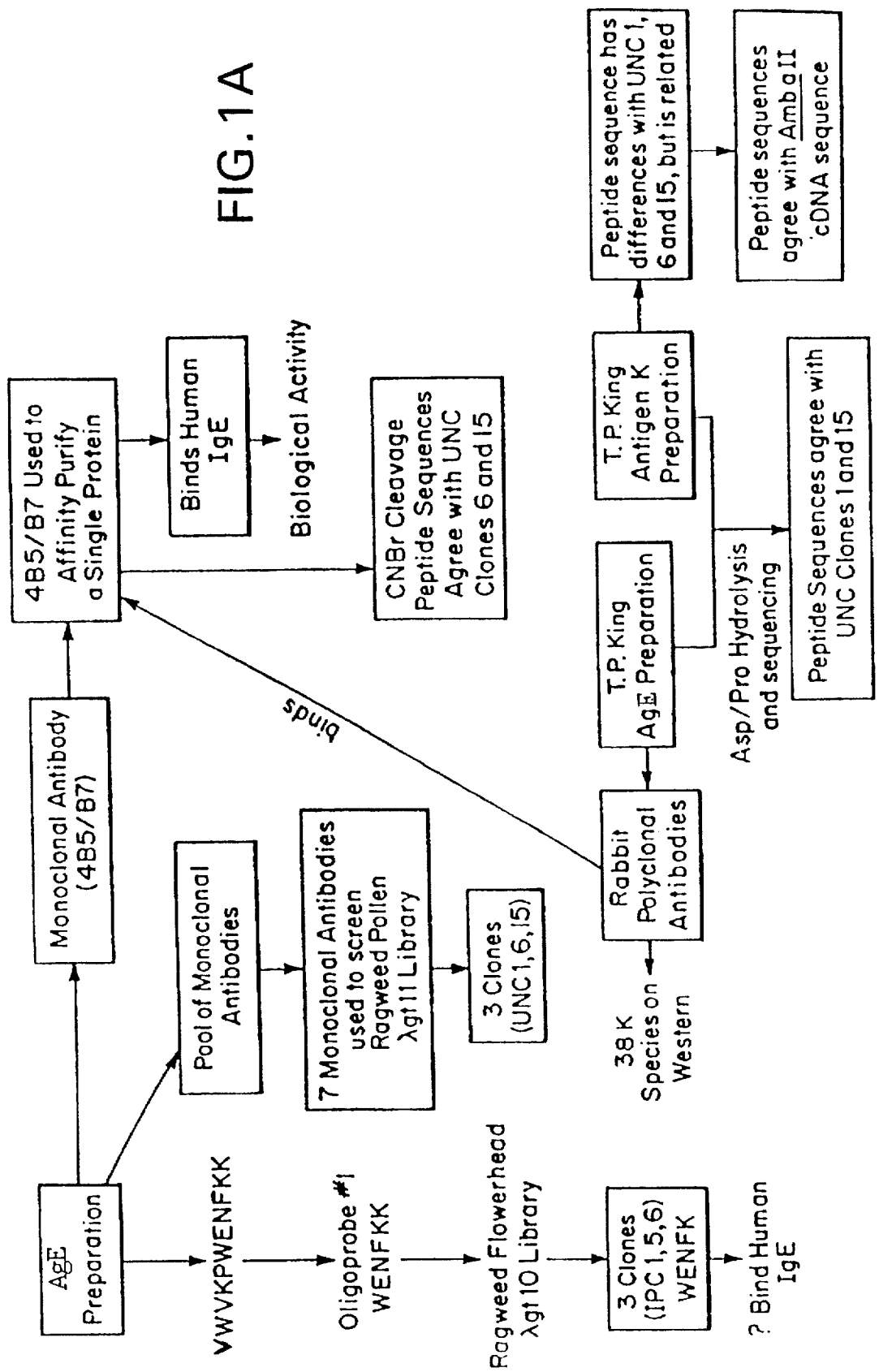
FIGS. 1A–1B is a schematic representation of several routes by which assessment of proteins or peptides present in Amb a I and DNA encoding such proteins or peptides have been identified isolated and characterized.

The following is a description of several approaches which have been used to identify and isolate DNAs encoding proteins or peptides from Amb a I or Antigen E preparations, as well as to isolate from an Amb a I preparation a protein shown to have Amb a I activity. As represented in FIG. 1A, an Amb a I or Antigen E preparation, which was prepared from pollen extract by a method based on the method of T. P. King and co-workers, was produced. King, T. P. et al, *Arch. Bioch. and Biophys.*, 212: 127–135 (1981). A panel of monoclonal antibodies produced by Klapper and co-workers was used to identify proteins in the preparation. Smith, J. J. et al., *Mol. Immun.*, 25: 355–365 (1988). Sequences of several peptides from an Antigen E preparation were determined by conventional techniques.

The following sections describe: 1) use of a pool of these monoclonal antibodies (i.e., a pool of monoclonal antibodies reactive with Amb a I) to identify clones containing DNA inserts encoding the reactive product and 2) use of an oligonucleotide probe, constructed from an amino acid sequence present in the Amb a I preparation to identify clones containing DNA inserts encoding the amino acid sequence. Each approach resulted in identification of three clones containing DNA encoding an amino acid sequence present in the Amb a I or Antigen E preparation. The two sets of clones isolated as described below have been shown to be different from each other.

Use of Monoclonal Antibodies to Identify Clones Containing DNA Inserts Encoding Ragweed Protein A pool of seven monoclonal antibodies specifically reactive with components of the Amb a I preparation was used to screen a ragweed pollen λgt11 library, using a known method. Young, R. A. and R. W. Davis, *Proceedings of the National Academy of Sciences USA*, 80: 1194–1198 (1983). This resulted in identification of three clones, initially designated UNC Clones 1, 6 and 15 and referred to herein as Amb a IA, IB and IC, respectively, which expressed a product recognized by at least one of the monoclonal antibodies in the panel. The nomenclature of cDNAs encoding the allergens Amb a I and Amb a II have been named according to the recommendations of the International Union of Immunological Societies Sub-Committee for Allergen Nomenclature (Marsh. et al., *Annals of Allergy*, 60: 499–504 (1988)).

DNA isolated from the three reactive clones was sequenced, using the method of Sanger, F. et al. Sanger, F. et al., *Proc. Natl. Acad. Sci., USA*, 74: 5463 (1977). The nucleotide sequences of the three clones are presented in FIGS. 2–4.

Using the partial cDNA sequences presented in FIGS. 2–4, cross-hybridization (as described in Example 2) and PCR methods (as described in Example 3) were used to isolate full-length cDNAs encoding Amb a IA (FIG. 11), Amb a IB (FIG. 12), Amb a IC (FIG. 13) and Amb a ID (FIG. 14).

In the course of DNA sequencing of cross-hybridizing cDNAs from a separately constructed λgt10 ragweed flowerhead library, a new cDNA was derived that shared sequence with Amb a II peptide sequence (FIG. 15 and FIG. 16). Construction of this library and isolation of the new cDNA are described in Example 2. The composite amino acid sequences of the Amb a I and Amb a II multigene family are shown in FIG. 16, with the regions of similarity and of disagreement represented. In FIG. 16, the sequence of Amb a I is given in standard one-letter code. Sequences for the other Amb a I family members are given relative to that of Amb a I, with only differences being shown. A dash indicates identity between the two sequences. An asterisk indicates a break in the sequence introduced to maintain maximal alignment. Amino acid numbering is based on the Amb a IB sequence. Wherever sequence polymorphism has been observed in a given family member, the dominant sequence is given in superscript and the minor sequence is given in subscript. Polymorphisms in a given family member occur as independent events, except for amino acids 183–189 of Amb a ID, in which the polymorphism occurs as a block.

Use of an Oligonucleotide Probe to Identify Clones Containing DNA Inserts Encoding Ragweed Protein As also represented in FIG. 1A, an amino acid sequence (SEQ ID NO: 1) (WENFK) in the Amb a I preparation, which was identified and sequenced by conventional techniques, was used to deduce the sequence of an oligonucleotide probe (oligoprobe) encoding the amino acid sequence. The amino acid sequence used to deduce the oligonucleotide sequence was VWVKPWENFK (SEQ ID NO: 2). A portion of that amino acid sequence (WENFK) was used to deduce the sequence of the oligoprobe, designated AGE#1. AGE#1 was used, as described in Example 1, to screen a cDNA library constructed in λgt10 using polyA$^+$ enriched RNA from pooled short ragweed flower heads. Screening with this oligoprobe resulted in identification of ten duplicated signals. These duplicated signals (clones) were subjected to a secondary screening with the same AGE #1 oligonucleotide probe. Three of the positives (referred to as secondary positives) were clearly detected in duplicate. The clones (designated IPC Clone 1, IPC Clone 5 and IPC Clone 6) identified in this manner were grown under appropriate conditions and verified as positive, by Southern blot analysis.

The cDNA insert from each of the three clones was isolated and cloned into M13mp18 and sequenced (FIGS. 5–7). The amino acid sequence was also deduced (FIGS. 8–10). Open reading frames in the sequenced cDNAs were examined (FIGS. 8–10) and the sequence (from which the sequence of the oligonucleotide probe had been deduced) was identified. That the cDNA inserts encode a portion of translated protein was supported by the fact that the surrounding amino acid sequence deduced from the DNA sequence (VWVKP) agreed with the amino acid sequence initially used to deduce the sequence of the oligoprobe (FIG. 8–10). T cells from allergic patients could be stimulated by a synthetic peptide RAE4 (Table 5). The RAE4 sequence was deduced from IPC Clone 5 (FIG. 8).

As is evident from a comparison of the two "sets" of nucleotide sequences (i.e., set 1, which are the DNAs isolated through use of monoclonal antibodies, and set 2, which are the DNAs isolated through use of the oligoprobe), there is homology among sequences within a set (i.e., within FIGS. 2–4 and within FIGS. 5–7) but little similarity in sequences between sets.

Thus, it is apparent that the Amb a I or Antigen E preparation is heterogenous in nature and represents a family (or families) of proteins or that there is considerable polymorphism in Amb a I-encoding DNA. This is in contrast to present literature descriptions of Amb a I or Antigen E, which refer to Antigen E as a protein, rather than as a group or groups of allergenic proteins, present in ragweed pollen, to which ragweed-sensitive individuals respond.

Additional Demonstration of Isolation of Antigenic Peptides and DNAs of Amb a I

Additional results further demonstrate that antigenic peptides of Amb a I and DNAs encoding them have been identified and isolated. As represented in FIG. 1A, a selected monoclonal antibody (designated 4B5/B7) which recognizes an Amb a I preparation unsubjected to denaturing conditions was used to affinity purify from pollen extract a single protein, which is referred to as affinity purified Amb a I. This was carried out, using known techniques, by producing the desired monoclonal antibody, isolating it in large quantities from ascites and immobilizing it on Sepharose (Pharmacia). Aqueous pollen extract was passed over the monoclonal antibody-containing column and a protein species was eluted. Antigen E isolated in this manner was shown, using both Western blot (FIG. 17) and ELISA techniques, to bind human IgE, thus demonstrating biological activity expected of an Amb a I protein or peptide.

Peptide sequence analysis was carried out as follows: Two peptides were isolated from partial tryptic digestion or cyanogen bromide (CNBr) cleavage of affinity purified Amb a I, respectively, and then subjected to peptide sequencing. Because the N-terminal of Amb a I is blocked, no amino acid sequence can be obtained from direct N-terminal protein sequence analysis. The result of the sequence analysis of the tryptic peptide demonstrated that the major portion of its amino acid sequence agreed with peptide sequence 45 to 77 encoded by the Amb a IA cDNA (Table 1). Table 1 is a comparison of the amino acid sequences of Amb a I protein, determined by protein sequence analysis, with the amino acid sequence deduced from Amb a I cDNA. The CNBr cleavage peptide sequencing demonstrated that the CNBr cleavage peptide was similar to the peptide sequence 171 to 184 encoded by the Amb a IA cDNA (Table 1).

Further peptide sequence analysis was performed from the protein cleavage mixture without isolating individual peptides. The techniques employed involved specific hydrolysis (with 70% formic acid or CNBr) of the putative Asp-Pro and Met-Pro bonds deduced from the cDNA sequences of Amb a I. Any primary amino groups were then blocked by reaction with o-phthalaldehyde prior to conventional sequencing from any available N-terminal proline residue.

TABLE 1

Amb a I PROTEIN SEQUENCES[a] COMPARED TO PROTEIN SEQUENCE DEDUCED FROM Amb a IA cDNA SEQUENCES

PARTITAL TRYPTIC DIGEST[b]

```
                                    45      50      55      60      65      70      75      80      85      90
Amb a IA    cDNA                    T S G A Y N I I D G C W R G K A D W A E N R K A L A D C A Q G F G K T V G G K D G D I Y T V T
Amb a I[c]  MAJOR[d]  (SEQ ID NO:5)  (T)S(G)A Y N I I D G C(W)R G K A D(W)A E N(R K)A L A D C A Q G F(G)
            MINOR[e]  (SEQ ID NO:6)  (D)                                      (S R)
AgE[f]                (SEQ ID NO:7)  (T)S G A Y N I I D G C W R G K A D W A E N R K A L A D C A Q G F G K T V G G K D G D I Y(T)V(T)
```

CNBr CLEAVAGE

```
                                    175     180     185
Amb a IA    cDNA      (SEQ ID NO:8)  H D V K V N P G G L I K S N D G
Amb a I[c]  MAJOR     (SEQ ID NO:9)  F D L K V N I G Q L I K(S)N
            MINOR     (SEQ ID NO:10) (A)F N Y(I)P L    (N)

AgE[f]                (SEQ ID NO:12) (H D V K V )P G G L I K( )N( )G
```

```
                                    280     285     290     295     300     305     310     315     320
Amb a IA    cDNA      (SEQ ID NO:13) P R C R H G F F Q V V N N N Y D K W G S Y A I G G S A S P T I L S Q G M R F C A P D K R S
Amb a I[f]  MAJOR     (SEQ ID NO:14) P R C R H G F F Q V V N N N Y D R W G(S)Y A I G G S(A )P T I L S Q G N( )F(C)A P(D G Y)
            MINOR#1[j] (SEQ ID NO:15)              F         I      P          D(H)         (N)                         V
            MINOR#2[k] (SEQ ID NO:16) P V L(T)P E(Q)S A(G N)
            MINOR#3[l]                T S G A Y N I I D G C W R G(K)A(D W)A

AgE         MAJOR     (SEQ ID NO:17) P R( )R H G F F Q V V N N N Y D(E W)G S Y A I G G S A S P T I
            MINOR#1[m] (SEQ ID NO:18) A(W)N(W)R(T E K)D L
            MINOR#2[n] (SEQ ID NO:19) V (I)N L (D Q)E I(F V)
```

70% FORMIC ACID HYDROLYSIS OF ASP-PRO PEPTIDE BOND[i]

```
                                    365     370     375     380     385     390     395
Amb a IA    cDNA      (SEQ ID NO:20) P V L T P E Q S A G M I P A E P G E S A L S L T S S A G V L S C Q F G A P
Amb a I     MAJOR     (SEQ ID NO:21) P V L(N P)E( )N A G M I Q A E(P G)E A
            MINOR[e]  (SEQ ID NO:22)             I

AgE                   (SEQ ID NO:23) P V L T P E Q S A G M I P A E P G E S A L S L T S(S)A G V L( C)Q P(G A)P

35kD[p,q]             (SEQ ID NO:24) P V L T P V Q S A G M I P A E P G E A A I(K)L T S S
```

[a]the amino acids are presented in single letter code; uncertain residues are included in paranthesis
[b]the peptides were separated by SDS-PAGE then Western blotted on PVDP membrane for sequence analysis
[c]IPC's affinity purified Amb a I preparation
[d]major squence determined in protein sequence analysis TABLE 1-continued Amb a I PROTEIN SEQUENCES* COMPARED TO PROTEIN SEQUENCE DEDUCED FROM Amb a IA cDNA SEQUENCES

[e] minor squence determined in protein sequence analysis
[f] T. P. King's Amb a I preparation
[g] the cleavage mixture was separated by SDS-PAGE then Western blotted on PVDP membrane
[h] the sequence is most similar to a IA cDNA sequence among all the cloned cDNA sequence
[i] the primary amine of the cleavage mixture was blocked by o-phthalaldehyde on the 7th step of sequence analysis
[j] similar to the a IIA cDNA sequence 277–315
[k] similar to the a IA cDNA sequence 361–371
[l] similar to the a IA cDNA sequence 45–63
[m] similar to the a IC cDNA sequence 338–347
[n] similar to the a IC cDNA sequence 126–135
[o] matches to a IC cDNA sequence 363
[p] TPC's Amb a I preparation with molecular weight of 35,000 dalton
[q] matches to a IC cDNA sequence 361–386

Results of these assessment (shown in Table 1) demonstrated that two peptide sequences determined from the affinity purified Amb a I preparation agreed with that encoded by two portions of Amb a IA DNA sequence (277–321 or 361–397). The minor sequences detected in the peptide sequence analysis also corresponded to a portion of peptide sequence encoded by cDNA's of Amb a I or Amb a II. The above peptide sequence analyses provided strong support that Amb a I or Antigen E-encoding DNA had been isolated.

An Antigen E preparation obtained from Dr. T. P. King was also subjected to peptide sequencing. The same peptide sequencing techniques were employed. Four peptides sequences were identified which agreed with the same four segments of peptide sequence encoded by Amb a IA DNA (45–92, 171–186, 277–321 and 361–397 in Table 1). This provided additional proof that Amb a I or Antigen E-encoding DNA had been isolated.

The same techniques were used with purified Antigen K (Amb a II) from Dr. T. P. King. Results demonstrated that two peptide sequences agreed with two portions of peptide sequence encoded by DNA of Amb a II (Table 2, see Example 2; FIG. 15). Table 2 is a comparison of the amino acid sequences of Amb a II protein, determined by protein sequence analysis, with the amino acid sequence deduced from Amb a II cDNA. This finding provided support that ragweed pollen allergen encoding DNA had been isolated.

ion-exchange chromatography (King, T. P. et al., *Ach. Biochem. Biophys.*, 212: 127–135 (1981)). The different isoforms described, designated A, B, C and D, were interpreted to be produced by limited proteolysis of the intact Amb a I and Amb a II species. It should be noted that these isoforms, designated A, B, C, etc., have no direct relationship with the nomenclature outlined in this invention (i.e., Amb a IA, Amb a IB, etc.).

A 35,000 dalton species coprecipitates from ragweed pollen extract with Amb a II in 45% saturation of ammonium sulfate. Most of these proteins are shown to be agregated by gel filtration chromatography. Some monomeric forms of these proteins were separated from Amb a II by ion exchange chromatography. The sequencing technique, which involved 70% formic acid hydrolysis of putative Asp-Pro bound and o-phthalaldehyde blocking of primary amino groups, demonstrated that the predominant protein corresponds to that encoded by the DNA sequence of Amb a IC. This peptide sequence is referred to as 35 kD in Table 1. This result provided additional support that Amb a I proteins are heterogeneous in nature and are encoded by closely related DNA's.

Figure 17:
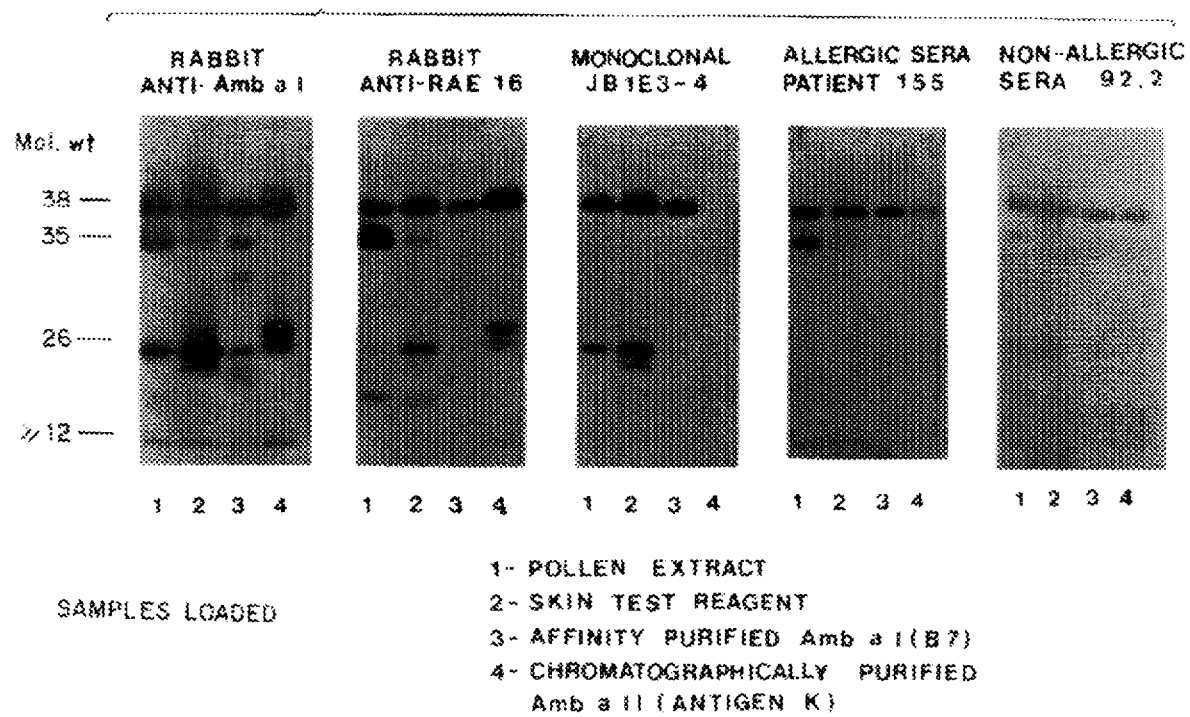
FIG. 17 is a photograph of a Western blot of affinity purified Amb a I treated with rabbit anti-Amb a I polyclonal antibody, JB1E3-4 anti-Amb a I monoclonal antibody or ragweed allergic patient sera.

As is also represented in FIG. 1A, rabbit polyclonal antibodies were produced using the King Antigen E preparation. These antibodies were shown to identify a 38 kd protein species on a Western blot of pollen extracts (FIG. 17). A two-dimensional gel of ragweed pollen extract,

TABLE 2

Amb a II PROTEIN SEQUENCES* COMPARED TO PROTEIN SEQUENCE DEDUCED FROM Amb a IIA c DNA SEQUENCE

CNBr CLEAVAGE[b]

| | | | 280 285 290 295 300 305 310 315 320 |
|---|---|---|---|
| Amb a IIA | cDNA | (SEQ ID NO:25) | P R C R F G F F Q I V N N F Y D R W D K Y A I G G S S N P T I L S Q G M K F V A F D F I Y |
| AgK[c] | MAJOR[d] | (SEQ ID NO:26) | P R( )R F G F F Q I V N N F Y D R W D(H)Y A I G G S S N P T I L S Q G N(R)F V A P(D )I(Y) |
| | MINOR[e,f] | (SEQ ID NO:27) | P V L T P E Q N A G M |
| Amb a II[g] | | (SEQ ID NO: 27) | P (R R)F G F F Q I V N N F Y D |

70% FORMIC ACID HYDROLYSIS OF ASP—PRO PEPTIDE BOND[b]

| | | | 365 370 375 380 385 390 395 |
|---|---|---|---|
| Amb a IIA | cDNA | (SEQ ID NO:29) | P V L T A E Q N A G M M Q A E P G D H V P Q L T M N A G V L T C S P G A P |
| AgK | | (SEQ ID NO: 30) | P V L T A E Q N A G M M Q A E P G D H V P Q L T M N A(G)V(L S)P G A P |
| Amb a II | MAJOR | (SEQ ID NO: 31) | P V L T A E Q N A G M M Q A E P G D M V P Q L T M N A G V L T( )S P G A P |
| | MINOR | (DEQ ID NO:32) | P      S      I P      E S   A L S      S           (S) |

*the amino acids are presented in single letter code; uncertain residues are included in paranthesis
[b]o-phthalaldehyde is reacted with peptide mixture prior to conventional peptide sequence analysis
[c]T. P. King's Amb a II preparation
[d]major squence determined in protein sequence analysis
[e]minor squence determined in protein sequence analysis
[f]matches the a IIA cDNA sequence 361–371
[g]matches the a IIA cDNA sequence 361–371
[h]matches to a IA cDNA sequence 361–397

Figure 18:
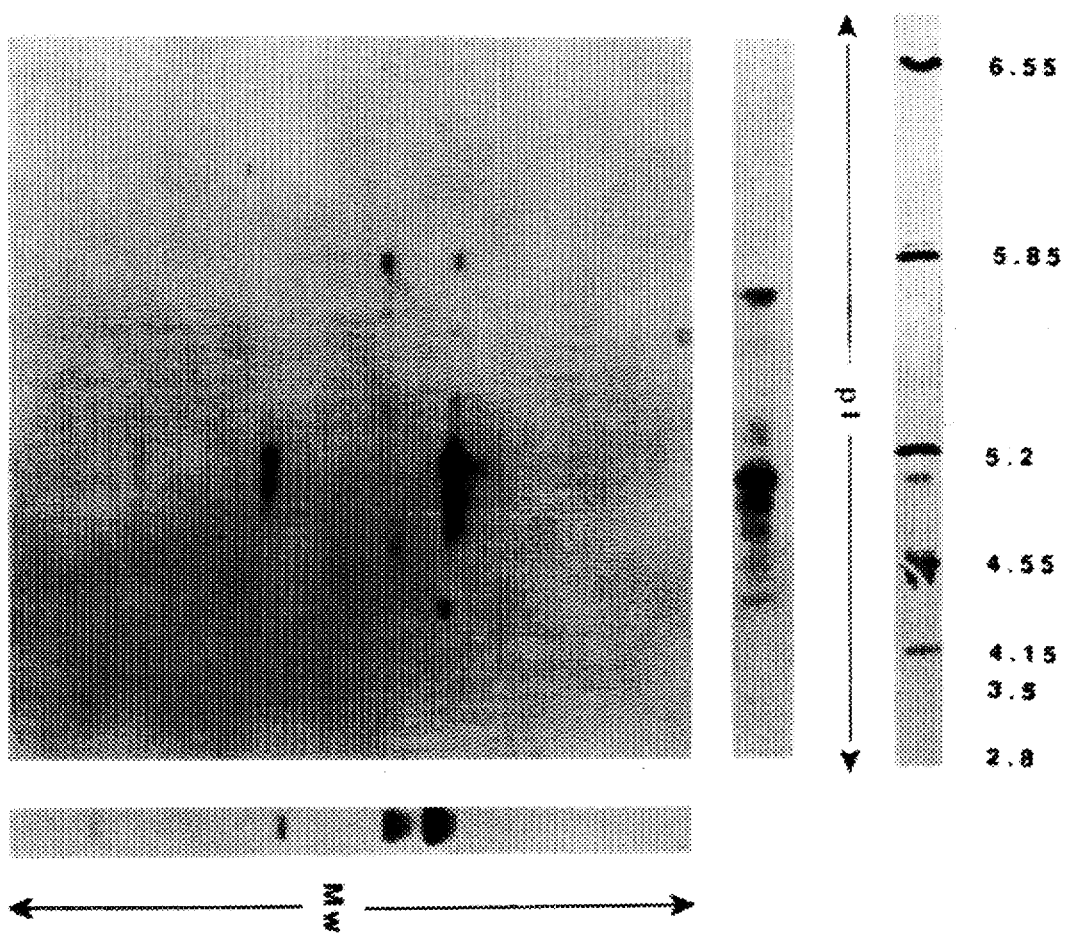
FIG. 18 is a photograph of a two dimensional gel of an aqueous extract of short ragweed pollen, separated on the basis of size and charge and stained with T. P. King's antibody, which recognizes Amb a I (goat polyclonal anti-Amb a I).

It has been previously reported that Amb a I and Amb a II share some antigenic determinants using rabbit and human antisera (King, T. P., *Adv. Immun.*, 23: 77–105 (1976)). However, the exact relationship between the two antigens, until the present invention, has remained unclear. King and colleagues have also reported that different isoforms of antigen E and K (Amb a I and Amb a II) can be isolated by electrophoresed in one dimension on the basis of charge and in the other dimension on the basis of size and treated with goat anti-Amb antibodies is shown in FIG. 18. Results demonstrate binding to several proteins present in ragweed pollen extract with a relative molecular weight of 38 kD, corresponding to differently charged forms of what was formerly referred to as Amb a I protein. These antibodies were also shown, using a similar technique, to bind to the affinity purified Amb a I described previously (FIG. 17).

It is clear from the antibody reactivity that the 4B5/B7 affinity purified Amb a I has a recognition pattern similar to that of the Amb a I of pollen and skin test reagent with both rabbit polyclonal anti-Amb a I and JB1E3-4 anti-Amb a I monoclonal antibody (FIG. 17). It also has readily detectable IgE reactivity on a Western blot (FIG. 17; patient number 155). It is also clear that chromatographically purified Amb a II (Antigen K) has cross-reactive B-cell epitopes with the affinity purified Amb a I (FIG. 17; anti-Amb a I polyclonal).

As a result of the work described herein,. cDNAs encoding allergenic peptides of proteins from a preparation of Amb a I, the major human allergen of ragweed and a preparation of Amb a II, have been cloned, isolated and sequenced; the encoded amino acid sequences (of the allergen(s)) have been deduced and peptides derived from Amb a I and Amb a II have been identified and isolated.

Figure 19:
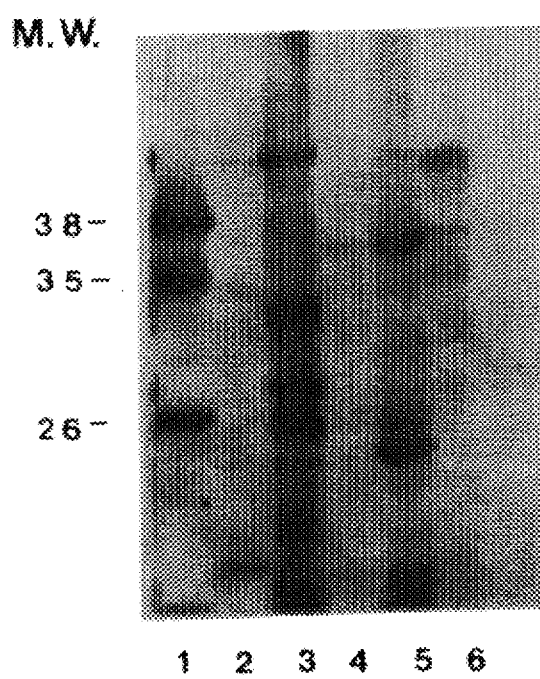
FIG. 19 is a photograph of a Western blot of several E. coli-expressed recombinant Amb a I cDNAs treated with goat anti-Amb a I antibody.
Figure 20:
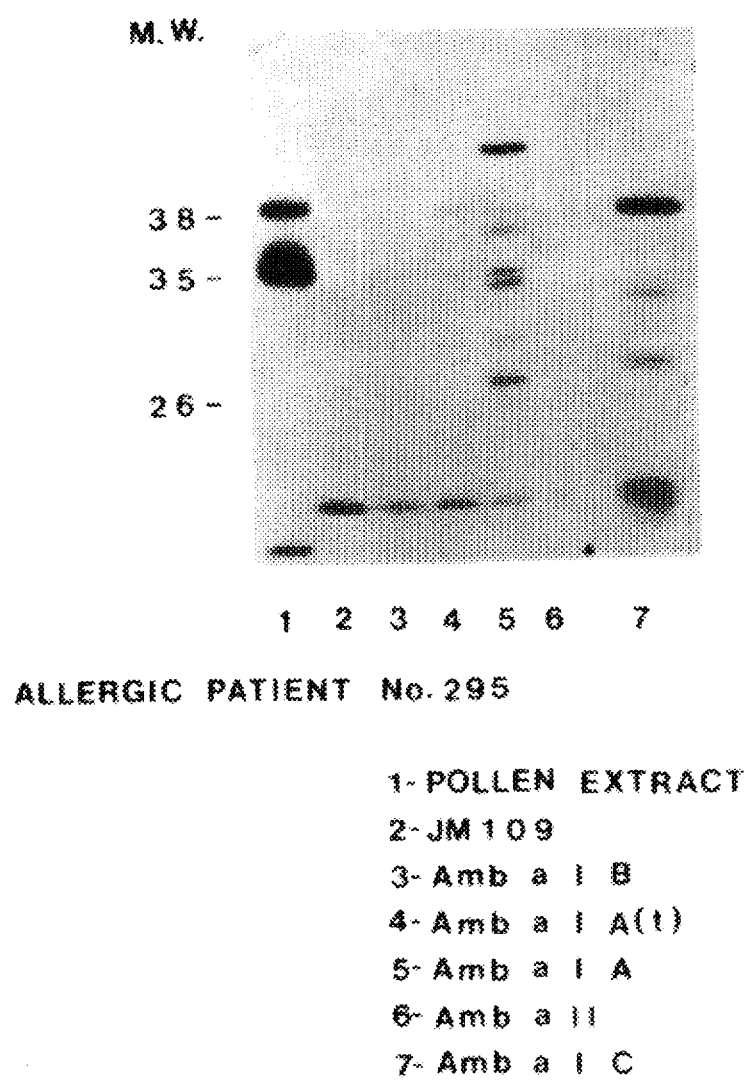
FIG. 20 is a photograph of a Western blot of several E. coli expressed recombinant Amb a I cDNAs treated with human allergic sera strained with anti-human IgE.

Furthermore, full-length and truncated cDNAs encoding several members of the Amb a I multigene family, as well as Amb a II, were cloned in-frame into the expression vector pTrc99 (Amann et al. Gene, 69: 301–315, (1988)) and transformed into the JM109 host. Expression of recombinant Amb a I and Amb a II protein was induced by 1 mM isoprophyl-β-D-thiogalactopyranoside, cells were harvested, lysozyme treated, sonicated and insoluble inclusion bodies recovered by a low speed centrifugation. Recombinant Amb a I and Amb a II protein present in the recovered pellet was solubilized in buffer containing 8M urea, 50 mM Tris HCl pH8.0, 50 mM NaCl, 1 mM EDTA, 1 mM dithiothreitol, 1 mM phenylmethylsulfonyl fluoride. After solubilization, the crude urea lysate was dialyzed at 4° C. against PBS. The expressed recombinant Amb a I and Amb a II proteins were Western blotted and results are shown in FIGS. 19 and 20. Results demonstrate (FIG. 19) that goat anti-Amb a I antibody binds specifically to several forms of Amb a I (A, B and C), as well as to Amb a II (antigen K). This antigenic cross-reactivity is consistent with the observed sequence homology of the cDNAs (see FIG. 16). They further demonstrate (FIG. 20) that allergic human IgE binds specifically to some members of the Amb a I multigene family. In the case of patient #295, Amb a IA (full-length) and Amb a IC are bound specifically by IgE to a far greater extent than Amb a IB or Amb a II. A high level of variability in the patterns of IgE binding is seen (Table 3 and data not shown), suggesting that different patients respond to the different Amb a I proteins to different extents.

TABLE 3

SUMMARIZED WESTERN BLOT DATA*

| Patient | Pollen | Antigen IA(t) | IA | IB | IC | IIA |
|---|---|---|---|---|---|---|
| 151 | + | − | + | − | + | + |
| 222 | +− | +− | +− | +− | +− | + |
| 291 | +++ | + | +++ | − | +++ | +− |
| 295 | +++ | + | +++ | + | +++ | − |
| 296 | ++ |  | ++ |  | ++ | − |

− no signal over background
+− barely discernable over background
+ clearly positive
++ strongly positive
+++ highly positive
*selected from the total of ten patients screened to date.

An analysis of SDS-PAGE Western blot of IgE binding to several recombinant forms of Amb a I and Amb a II has demonstrated that there is considerable variation in the pattern observed with different patients. Of the ten ragweed allergic patients examined, all possess serum IgE that binds to at least one recombinant Amb a I or Amb a II, with some patient's IgE binding several different recombinant species (summarized in Table 3). Comparison of human IgE binding to recombinant Amb a I and Amb a II proteins with anti-peptide and monoclonal anti-Amb a I antibodies have provided data consistent with the conclusion that the N-terminal portion (historically referred to as the β-region) of Amb a IA includes the major IgE epitope(s). This data (Table 3) is based on the observation that Amb a IA(t) (truncated Amb a IA; amino acid 70–398) binds ragweed allergic patient IgE less well than the full-length Amb a IA (amino acid 10–398). It is expected that the other Amb a I and Amb a II forms possess the same IgE binding properties (see FIG. 20, for example).

T cells from patients allergic to ragweed, previously stimulated with a mixed ragweed pollen extract, can recognize and proliferate in response to pollen extract, ragweed skin test reagent (RWST), affinity purified Amb a I protein and crude bacterial lysates containing recombinant Amb a I gene products IA, IB and IC (Table 4). T cells from these patients do not proliferate in the presence of an equivalent amount of control bacterial lysate, JM109. These results demonstrate that each gene product can stimulate some T cell reactivity. The use of crude bacterial lysates as antigens precludes a firm conclusion from the negative responses, since the relative levels of recombinant proteins in lysate have not been determined.

TABLE 4

STIMULATORY RESPONSE[a] OF THE HUMAN T CELL TO RECOMBINANT RAGWEED PROTEINS

| PATIENT # | POLLEN | RWST[b] | Amb a I[c] | Amb a IB LYSATE | Amb a IC LYSATE | Amb a IA(t) LYSATE | Amb a IA LYSATE | JM109 LYSATE |
|---|---|---|---|---|---|---|---|---|
| 151 2° | +++ | + | (+) | + | + | + | (+) | − |
| 222 2° | +++ | +++ | +++ | − | ++ | ++ | ++ | − |
| 274 2° | ++ | ++ | ++ | + | ++ |  |  | − |
| 295 2° | +++ |  |  | + | + | + |  | − |
| 296 2° | +++ | +++ | +++ | +++ | +++ | +++ |  | − |
| 314 2° | +++ | +++ | +++ | +++ | +++ | +++ |  | − |
| 316 2° | +++ | +++ | +++ | ++ | +++ | +++ |  | − |
| 319 2° | +++ | +++ | ++ | (+) | ++ | − |  | − |
| 320 2° | ++ | ++ | +++ | + | − | ++ |  | − |
| 321 2° | +++ | +++ | + | ++ | + | ++ |  | − |

[a]proliferation responses as compared to medium control:
(+) 2 fold
+ 2–4 fold
++ 4–10 fold
+++ >10 fold
[b]ragweed skin test reagent from Hollister-Stier
[c]affinity purified Amb a I Uses of the Subject Allergenic Proteins/Peptides and DNA Encoding Same The materials resulting from the work described herein, as well as compositions containing these materials, can be used in methods of diagnosing, treating and preventing ragweed allergy. In addition, the cDNA (or the mRNA from which it was transcribed) can be used to identify similar sequences in any variety or type of ragweed and, thus, to identify or "pull out" sequences which have sufficient homology to hybridize to, for example, DNA from short ragweed pollen. This can be carried out, for example, under conditions of low stringency; those sequences which have sufficient homology (generally greater than 40%) can be selected for further assessment using the method described herein. Alternatively, high stringency conditions can be used.

In this manner, DNA of the present invention can be used to identify, in other types of ragweed (such as giant ragweed or Western ragweed) sequences encoding peptides having amino acid sequences similar to that of Amb a I and, thus, to identify allergens in such other types of ragweed. Thus, the present invention includes not only Amb a I and other ragweed allergens (e.g., Amb a II or Antigen K) encoded by the present DNA sequences, but also other ragweed allergens encoded by DNA which hybridizes to DNA of the present invention.

Proteins or peptides encoded by the cDNA of the present invention can be used, for example, as "purified" allergens. Such purified allergens are useful in the standardization of allergen extracts which are key reagents for the diagnosis and treatment of ragweed allergy. Furthermore, by using peptides based on the sequences listed in FIGS. 2 through 16, anti-peptide antisera or monoclonal antibodies can be made using standard methods. Such reagents can be specifically directed against individual isoforms of Amb a I or Amb a II (i.e., directed against divergent regions/epitopes of the molecule) or can be specific for all forms of Amb a I or Amb a II (i.e., directed against common sequences/epitopes). These sera or monoclonal antibodies, directed against Amb a I or Amb a II, can be used to standardize allergen extracts. One such monospecific anti-peptide antisera has already been successfully produced. This rabbit antisera, directed against an Amb a II sequence (amino acid 326–338; designated RAE 50.K with the sequence: CLRTGAQEPEWMT) (SEQ ID NO: 33) binds specifically on Western blots to recombinant Amb a II but not Amb a IA, B or C (data not shown).

Through use of the peptides of the present invention, allergen preparations of consistent, well-defined composition and biological activity can be made and administered for therapeutic purposes (e.g., to modify the allergic response of a ragweed-sensitive individual to a ragweed pollen). Such peptides or proteins (or modified versions thereof, such as are described below) may, for example, modify B-cell response to a ragweed allergen, T-cell response to a ragweed allergen or both responses. Purified allergens can also be used to study the mechanism of immunotherapy of ragweed allergy and to design modified derivatives or analogues which are more useful in immunotherapy than are the unmodified ("naturally-occurring") peptides.

Work by others has shown that high doses of allergens generally produce the best results (i.e., best symptom relief). However, many people are unable to tolerate large doses of allergens because of allergic reactions to the allergens. Modification of naturally-occurring allergens can be designed in such a manner that modified peptides or modified allergens which have the same or enhanced therapeutic properties as the corresponding naturally-occurring allergen but have reduced side effects (especially anaphylactic reactions) can be produced. These can be, for example, a peptide of the present invention (e.g., one having all or a portion of the amino acid sequence of a peptide derived from the DNA insert of Clone Amb a IA, Clone Amb a IB, Clone Amb a IC, Amb a II, IPC Clone 1, IPC Clone 5 or IPC Clone 6, or their full-length cDNAs) or a modified peptide or peptide analogue (e.g., a peptide in which the amino acid sequence has been altered to modify immunogenicity and/or reduce allergenicity or to which a component has been added for the same purpose). For example, Amb a I peptides can be modified using the polyethylene glycol method of A. Sehon and co-workers.

Administration of the peptides of the present invention to an individual to be desensitized can be carried out using known techniques. A peptide or combination of different peptides can be administered to an individual in a composition which includes, for example, an appropriate buffer, a carrier and/or an adjuvant. Such compositions will generally be administered by injection, oral administration, inhalation, transdermal application or rectal administration. Using the structural information now available, it is possible to design a ragweed pollen peptide which, when administered to a ragweed-sensitive individual in sufficient quantities, will modify the individual's allergic response to a ragweed allergen. This can be done, for example, by examining the structures of the ragweed proteins, producing peptides to be examined for their ability to influence B-cell and/or T-cell responses in ragweed-sensitive individuals and selecting appropriate epitopes recognized by the cells. Synthetic amino acid sequences which mimic those of the epitopes and which are capable of down regulating allergic response to ragweed allergen can also be used. Proteins, peptides or antibodies of the present invention can also be used for detecting and diagnosing ragweed allergy. For example, by combining blood or blood products obtained from an individual to be assessed for sensitivity to ragweed allergen with an isolated allergenic peptide of ragweed pollen, under conditions appropriate for binding of components (e.g., antibodies, T cells, B cells) in the blood with the peptide and determining the extent to which such binding occurs.

It is now also possible to design an agent or a drug capable of blocking or inhibiting the ability of ragweed allergens to induce an allergic reaction in ragweed-sensitive individuals. Such agents could be designed, for example, in such a manner that they would bind to relevant anti-ragweed IgEs, thus preventing IgE-allergen binding and subsequent mast cell degranulation. Alternatively, such agents could bind to cellular components of the immune system, resulting in suppression or desensitization of the allergic response to ragweed allergens. A non-restrictive example of this is the use of appropriate B- and T-cell epitope peptides, or modifications thereof, based on the cDNA/protein structures of the present invention to suppress the allergic response to ragweed allergens. This can be carried out by defining the structures of B- and T-cell epitope peptides which affect B- and T-cell function in in vitro studies with blood cells from ragweed-sensitive individuals.

The cDNA encoding an allergenic protein or peptide from ragweed can be used to produce additional peptides, using known techniques such as gene cloning. A method of producing a protein or a peptide of the present invention can include, for example, culturing a host cell containing an expression vector which, in turn, contains DNA encoding all or a portion of a selected allergenic protein or peptide (e.g., Amb a I protein or peptide). Cells are cultured under conditions appropriate for expression of the DNA insert (production of the encoded protein or peptide). The expressed product is then recovered, using known techniques. Alternatively, the Amb a I allergen or portion thereof can be synthesized using known mechanical or chemical techniques. As used herein, the term protein or peptide refers to proteins or peptides made by any of these techniques. The resulting peptide can, in turn, be used as described previously.

DNA to be used in any embodiment of this invention can be cDNA obtained as described herein or, alternatively, can be any oligodeoxynucleotide sequence having all or a portion of a sequence represented herein (See FIGS. 2–16), or their functional equivalents. Such oligodeoxynucleotide sequences can be produced chemically or mechanically, using known techniques. A functional equivalent of an oligonucleotide sequence is one which is capable of hybridizing to a complementary oligonucleotide sequence to which the sequence (or corresponding sequence portions) of FIGS. 2–16 hybridizes and/or which encodes a product (e.g., a polypeptide or peptide) having the same functional characteristics of the product encoded by the sequence (or corresponding sequence portion) of FIGS. 2–16. Whether a functional equivalent must meet one or both criteria will depend on its use (e.g., if it is to be used only as an oligoprobe, it need meet only the first criterion and if it is to be used to produce an Amb a I allergen, it need only meet the second criterion).

Antibodies against Amb a I peptides can be used to isolate additional components of ragweed allergens which can be used for further definition of the characteristics of the Amb a I family. Furthermore, anti-peptide sera or monoclonal antibodies directed against Amb a I and/or Amb a II can be used to standardize and define the content of ragweed skin test reagents (RWST). This use would include RWST other than those derived from *Ambrosia artemisiifolia l.* (e.g., Western, Desert, Giant ragweeds, etc.).

The structural information now available (e.g., DNA, protein/peptide sequences) can also be used to identify or define T cell epitope peptides and/or B cell epitope peptides which are of importance in ragweed allergic reactions and to elucidate the mediators or mechanisms (e.g., interleukin-2, interleukin-4, gamma interferon) by which these reactions occur. This knowledge should make it possible to design peptide-based ragweed therapeutic agents or drugs which can be used to modulate these responses.

The present invention will now be further illustrated by the following Examples, which are not intended to be limiting in any way.

EXAMPLE 1

Screening of a λgt10 cDNA Library Using an Oligonucleotide Probe

PolyA$^+$ enriched RNA extracted from pooled short ragweed flower heads was used to construct a cDNA library in the vector λgt10. The cDNA library was constructed using the Gubler and Hoffman method and the kit supplied by Amersham. Gubler, U. and B. J. Hoffman, *Gene*, 25: 263 (1983). A library of $1.4\times10^5$ plaques constituting approximately $7\times10^4$ recombinants was constructed. This library was plated out and screened according to the method of Benton and Davis. Benton, W. D. and R. W. Davis, *Science*, 196: 180 (1977).

Screening of the cDNA Library:

An amino acid sequence (VWVKPWENFKK) (SEQ ID NO: 34) thought to be derived from antigen E was used to deduce an oligonucleotide probe with which to screen the cDNA library.

| | | | | | | | |
|---|---|---|---|---|---|---|---|
| Amino Acid Sequence | W | E | N | F | K | K | (SEQ ID NO: 35) |
| Deduced Nucleotide Sequence | TGG | GAA | AAT | TTC | AAA | AAA | (SEQ ID NO: 36) |
| | | G | C | T | G | G | (SEQ ID NO: 37) |

Age #1 Oligoprobe

The AGE #1 oligoprobe was end-labeled with $^{32}P$ and used to probe 70,000 recombinants using the hybridization conditions listed below:

6×SSC

1×Denhardt's at 30 degrees C. for 22 hours

50 μg/ml *E. coli* tRNA

Ten duplicated signals were detected and these clones were subjected to a secondary screening with the same AGE #1 oligoprobe. It was subsequently discovered that the correct amino acid sequence is WENFKE (SEQ ID NO: 38).

A summary of the cloning procedure is listed below:

Primary Screen:

70,000 plaques
³²P—AGE #1 oligoprobe
Numerous spots with 10 signals were clearly seen on duplicated filters.

Secondary Screen:
Plaques from the 10 duplicate signals were picked and plated out at low density and rescreened using methods outlined in Clontech's catalog.

Tertiary Screening:
Three secondary positives numbered #1, #5, and #6 were clearly detected in duplicate. Each clone was grown up and verified as positive by Southern Blot analysis.

Sequencing of Positive Clones:
cDNA inserts from each of the clones were isolated then cloned into M13mp18. Each clone was sequenced using the Sanger dideoxy method and the deduced amino acid sequence was determined. Sanger, F. et al., *Proc. Natl. Acad. Sci. USA*, 74: 5463 (1977).

Identification of WENFKK and Surrounding Sequence:
The DNA sequences of the cDNA clones are presented in FIGS. 5, 6 and 7. The cDNA clones are not full-length and are less than 500 nucleotides in length. The AGE#1 oligoprobe nucleotide sequence is underlined in FIGS. 5, 6 and 7. Open reading frames in the sequenced cDNAs were examined and are presented in FIGS. 8, 9 and 10. The translated amino acid sequence (WENFK) used to deduce AGE#1 oligoprobe sequence is underlined as well as the N-terminal surrounding sequence (VWVKPWENFK (SEQ ID NO: 2); see FIGS. 8, 9 and 10). IPC clones 1 and 5 disagree with the amino acid sequence at only one out of ten residues (i.e., L instead of P). The presence of the correct surrounding sequence (VWVKP) (SEQ ID NO: 39) verifies that the cDNAs encode protein in pollen. Furthermore, a synthetic peptide based on the cDNA sequence designated RAE 4, which has the sequence EFPILGGITEVKDNDNSVDFC, (SEQ ID NO: 40) stimulates ragweed allergic patient T cells, in in vitro proliferation assays (see Table 5 and sequences in FIGS. 8, 9 and 10).

EXAMPLE 2
Cross-hybridization Methods Used to Obtain Full-Length cDNAs

Antigen E is reported to be a protein of approximately 38,000 molecular weight and consequently a full-length cDNA encoding this protein must be at least 1.1 Kb in length (King, T. P et al., *Arch. Biochem. Biophys.*, 212: 127 (1981)). Consequently, IPC clones 1, 5 and 6 as well as UNC clones 1, 6 and 15 (designated Amb a IA, IB and IC, respectively) are not full-length.

Figure 1B:
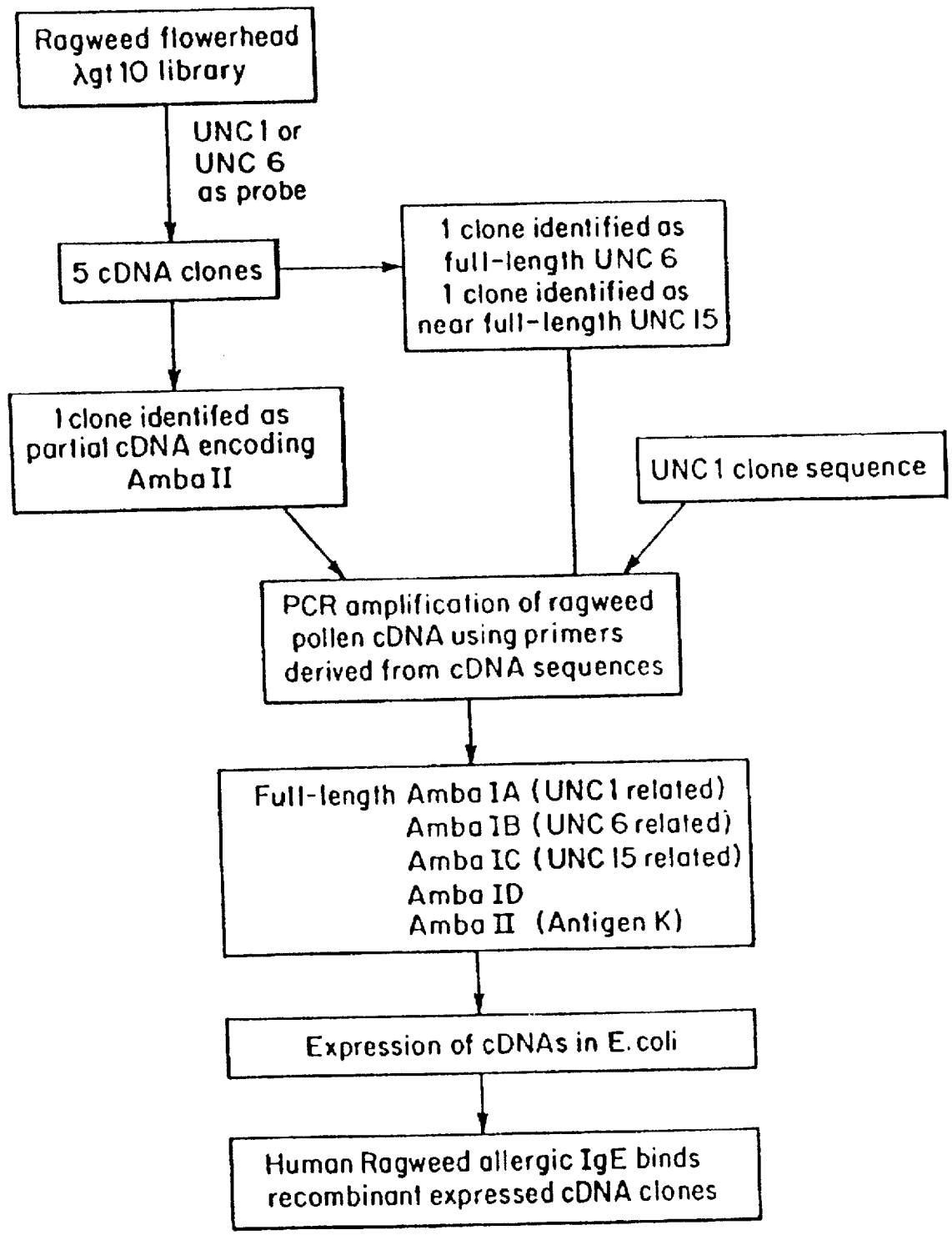

In order to isolate full-length clones, nick-translated ³²P-labelled Amb a I cDNA probes were used to screen the ragweed flowerhead λgt10 (see Example 1) and the ragweed pollen λgt11 library using standard methods (Maniatis et al., *Molecular Cloning*, Cold Spring Harbor Laboratory, (1982) ). Full-length or near full-length cDNAs encoding Amb a IB (FIGS. 12 and 16) and Amb a IC (FIGS. 13 and 16) were isolated using this method (FIG. 1B). One cross-hybridizing cDNA clone (called K6-5), which has an open reading frame of approximately 145 amino acids (amino acids 253–398; FIG. 15), was found to be significantly divergent from the previously isolated Amb a IA, Amb a IB, Amb a IC and Amb a ID and showed complete agreement (Table 2) with a peptide sequence derived from conventionally purified antigen K (a gift from T. P. King, New York). Consequently, this partial cDNA was designated as Amb a II (see FIG. 15 and below).

EXAMPLE 3
Polymerase Chain Reaction (PCR) Methods Used to Obtain Full-length cDNAs PCR methods can be successfully used to isolate both rare message cDNA as well as genomic clones of known sequence (Mullis et al., *Cold Spring Harbor Symposium Quant. Biol.*, 51: 263–273 (1986)). 5' and 3' oligonucleotide primers were synthesized and used in a PCR experiment with ragweed pollen cDNA serving as template. The 5' primers were deduced from N-terminal conserved regions of Amb a IB (FIG. 12) and Amb a IC (FIG. 13). The 3' primers were deduced from Amb a IA specific (UNC clone 1, designated Amb a IA, FIG. 2) and Amb a II specific (clone K6-5, partial 3' sequence of FIG. 15) non-coding strand sequences at the 3' end of the cDNA. A third 3' primer used to PCR clone Amb a ID was derived from a conserved region of the C-terminal end of Amb a IA, B and C (amino-acids 395–398 corresponding to GAPC stop). The oligonucleotide primers used to amplify and clone Amb a IA, Amb a ID and Amb a II cDNAs are listed below:

N-terminal primers used to produce full-length Amb a IA and Amb a II (amino acids 10–15)

```
         ECORI     L    Y    F    T    L    A    (SEQ ID NO:41)
IG38
         GGGAATTC  TTG  TAT  TTT  ACC  TTA  GC        (SEQ ID NO:42)
         5'                                            3'
```

N-terminal primer used to produce truncated Amb a IA and Amb a II (amino acids 10–15)

```
         ECORI     D    C    A    Q    G    F    (SEQ ID NO: 43)
IG33
         GGGAATTC  GAC  TGT  GCC  CAA  GGT  TTT  G    (SEQ ID NO: 44)
```

C-terminal primer used to produce full-length and truncated Amb a IA (12–29 nucleotides of the noncoding strand 3' of the TAA stop codon; see FIG. 2).

```
       PstI
IG32
       GGGCTGCAG  TCATTATAAGTGCTTAGT   (SEQ ID NO: 45)
       5'                               3'
```

C-terminal primer used to produce full-length Amb a ID (corresponding to the C-terminal conserved GAPC encoding region). The primer is of the non-coding strand and includes the stop codon and an artificially introduced Pst I cloning site (see FIG. 15).

```
       PstI
IG49
       GGGCTGCAG  TGC  TTA  GCA  AGG  TGC  TCC  (SEQ ID NO:46)
       5'                                        3'
```

C-terminal primer used to produce full-length and truncated Amb a II (44–76 nucleotides of the noncoding strand 3' of the TAA stop codon; see FIG. 15).

Pst I
AgK2
    GGGCTGCAG CGT GTC CAA ATC TAA TCA AAT GAA CAC TTA TGG  (SEQ ID NO:47)
    5'                                                       3'

First strand cDNA was synthesized from 1 μg RNA with the cDNA synthesis system plus kit (Amersham) using poly dT as primer. This single stranded cDNA was amplified using sets of primers (IG38 plus IG32; IG33 plus IG32; IG38 plus IG49; IG38 plus AgK2; IG33 plus AgK2) according to methods recommended in the GeneAmp kit (U.S. Biochemicals, Cleveland, Ohio). The samples were amplified with a programmable thermal controller; the first five rounds of amplification consisted of denaturation at 94° for 30 sec., annealing of primers to the template at 45° for 1 min. 30 sec., and chain elongation at 70° for 4 min. The final 20 rounds of amplification consisted of denaturation as above, annealing at 55° for 1 min. 30 sec. and elongation as above. The PCR generated bands corresponding to the predicted size on an analytical gel and DNA sequencing confirmed that the cDNAs corresponded to full-length and truncated Amb a IA and Amb a II (FIGS. 11 and 15, respectively) and full-length Amb a ID (FIG. 14).

The near full-length cDNAs presented in FIGS. 11 through 15, have their nucleotide sequences numbered such that the first nucleotide is designated number 1. Although some cDNAs start at what is probably the N-terminal methionine (Amb a IB, FIG. 12; Amb a IC, FIG. 13), some do not (Amb a IA, FIG. 11; Amb a ID, FIG. 14; Amb a II, FIG. 15). Consequently, since the cDNAs are of different lengths, their nucleotide numbers do not necessarily correspond from one sequence to another. The universal genetic code is used to deduce the amino acid sequences from the cDNA sequences and the complete amino acid sequence comparisons between the clones are presented in FIG. 16. In FIG. 16, the amino acids are numbered sequentially from the probably N-terminal methionine (designated number 1) of the Amb a IB sequence.

EXAMPLE 4
T Cell Responses to Ragweed Proteins and Peptides

Figure 21:
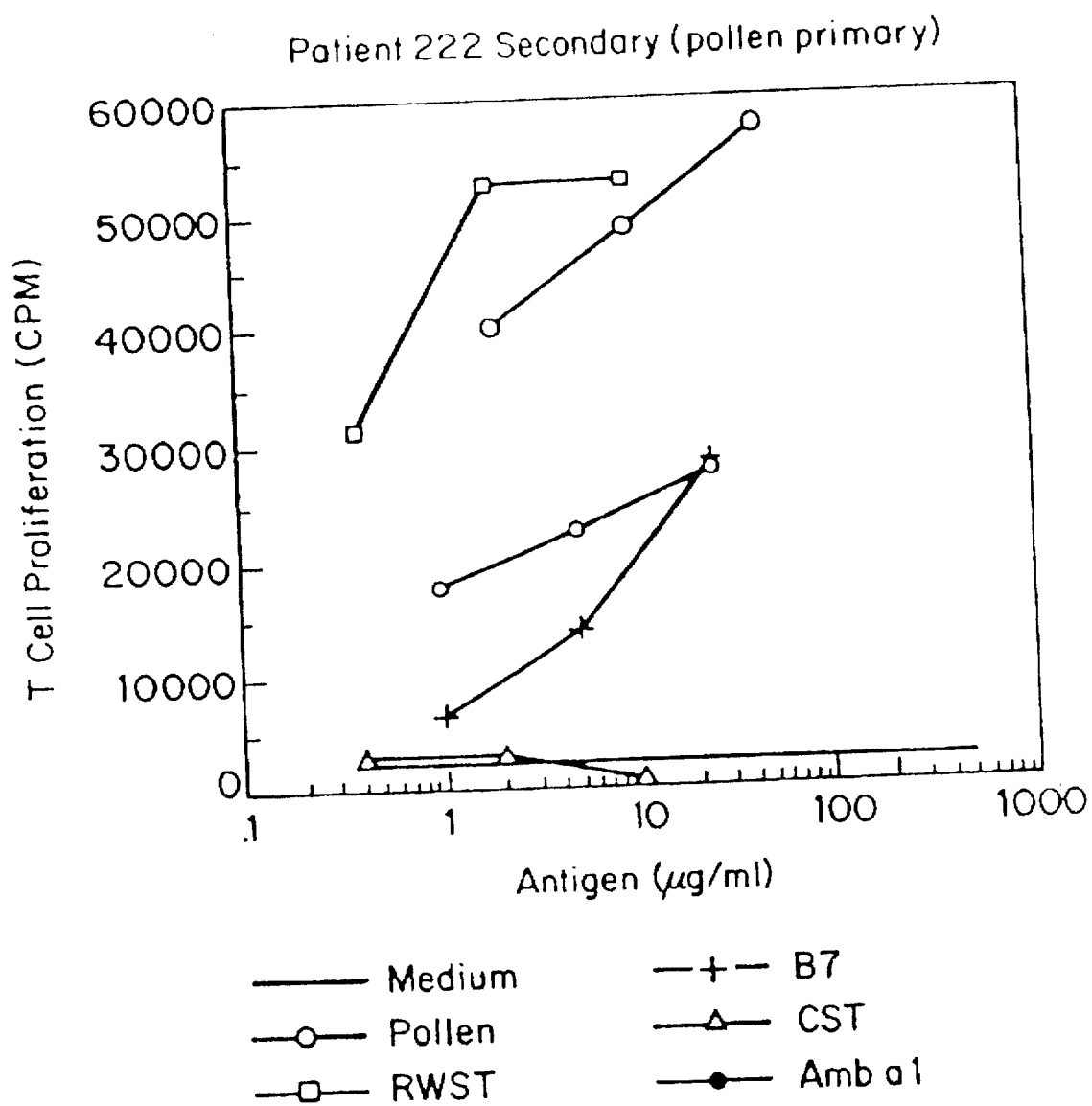
FIG. 21 is a graphic representation of T cell proliferation responses of ragweed allergic patient PBMC toward an aqueous extract of short ragweed pollen, affinity purified Amb a I (B7) chromatographically purified Amb a I and E. coli lysate containing expressed recombinant Amb a I proteins.

Peripheral blood mononuclear cells (PBMC) were purified from 60 ml of heparinized blood from ragweed-allergic patients. PBMC were subsequently treated as described below, although in individual cases, the length of time of cultivation with IL-2 and IL-4 and the specific ragweed proteins and peptides used for stimulation varied. As an example, ten ml of patient 222 PBMC at $10^6$/ml were cultured at 37° C. for 7 days in the presence of 20 micrograms aqueous ragweed pollen extract/ml RPMI-1640 supplemented with 5% pooled human AB serum. Viable cells were purified by Ficoll-Hypaque centrifugation and cultured for three weeks at 5 units recombinant human IL-2/ml and 5 units recombinant human IL-4/ml. The resting T cells were then restimulated (secondary) with 20 micrograms aqueous ragweed pollen extract/ml at a density of $2 \times 10^5$ T cells/ml in the presence of X-irradiated (3500 RADS) autologous PBMC ($5 \times 10^5$/ml) for three days, purified by Ficoll-Hypaque centrifugation and grown in 5 units IL-2/ml and 5 units IL-4/ml for two weeks. For assay, $2 \times 10^4$ resting secondary T cells were restimulated (tertiary) in the presence of $5 \times 10^4$ X-irradiated (3500 RADS) autologous PBMC or $2 \times 10^4$ autologous Epstein-Barr virus-transformed B cells (20,000 RADS) with various concentrations of allergen or their fragments in a volume of 200 microliters in 96-well round bottom assay plates for 3 days. Each well then received 1 microCurie tritiated (methyl) thymidine for 16 hours. The counts incorporated were collected onto glass fiber filters and processed for liquid scintillation counting. FIG. 21 shows the results of a representative assay, demonstrating the reactivity and specificity of the T cell culture to ragweed pollen proteins. Antigens used: IPC aqueous pollen extract (pollen), Hollister-Stier ragweed skin test. extract (RWST), ALK cat epithelium skin test extract (CST), affinity 4B5/B7 antibody purified (dialyzed) Amb a I (B7), and chromatographically purified Amb a I (Amb a I). Medium only control is shown as a line with no symbol. Alternatively, PBMC were sometimes carried only into a secondary assay (as outlined above for a tertiary assay) with 20 micrograms aqueous pollen extract for 7 days, followed by culture in 5 units IL-2/ml and 5 units IL-4/ml for 2–3 weeks. One ragweed allergic patient's T cells in secondary assay responded to pollen extract, RWST, B7 or Amb a I, but did not respond to CST or medium only (FIG. 21). Secondary and tertiary assays of a panel of ragweed allergic patients were performed using synthetic peptides derived from the sequences of various ragweed pollen proteins. The results of several experiments are shown in Table 5. Three peptides (RAE16.6, RAE45.15, RAE24.E) which are derived from the sequence of three different Amb a I cDNA's could not stimulate any of the patients' T cells. Another four peptides (RAE15.6, RAE3.D, RAE28.1, RAE26.15) which are also derived from the sequence of the same three cDNA's could stimulate 35 to 58% of the patients' T cells. One peptide (RAE4) which is derived from the cDNA of IPC Clone 5 could also stimulate 25% of the patients' T cells. These results are consistent with the above cDNA's encoding ragweed pollen proteins. They further demonstrate the opportunity offered by knowledge of the protein structures of the Amb I/II family/ies to identify peptidic fragments which stimulate a response in T cells from ragweed allergic patients and others which do not. By this method it is possible to identify novel therapeutic and diagnostics entities for use in the treatment and the diagnosis of ragweed allergy.

TABLE 5

Human Ragweed-Allergic T Cell Responses to Ragweed Peptides

| PEPTIDE[b] NAME | SEQUENCE BASED ON | NO. PATIENTS TESTED | NUMBER POSITIVE | POSITIVE % |
|---|---|---|---|---|
| RAE 16.6 | Amb a IB | 7 | 0 | 0 |
| RAE 45.15 | Amb a IC | 2 | 0 | 0 |
| RAE 24.E | Amb a IA | 9 | 0 | 0 |
| RAE 4 | Clone #5 | 28 | 7 | 25 |
| RAE 15.6 | Amb a IB | 20 | 7 | 35 |
| RAE 3.D | Amb a IA | 35 | 13 | 37 |
| RAE 28.1 | Amb a IA | 33 | 17 | 52 |
| RAE 26.15 | Amb a IC | 24 | 14 | 58 |

[a]Responses were scored as positive when the T cell proliferative response of ragweed pollen-specific T cells was greater than 2-fold above the culture medium control.
[b]Sequence of named peptide is as follows:
RAE 16.6 RIDKDLLENGAIC (SEQ ID NO: 48)
RAE 45.15 LNGELVVNSDKTIDGRGVK (SEQ ID NO: 49)

TABLE 5-continued

Human Ragweed-Allergic T Cell Responses to Ragweed Peptides

| PEPTIDE[b] NAME | SEQUENCE BASED ON | NO. PATIENTS TESTED | NUMBER POSITIVE | POSITIVE % |
|---|---|---|---|---|
| RAE 24.E | ETRRSLKTSGAYNIIDGCWRGKAD (SEQ ID NO: 50) | | | |
| RAE 4 | EFPILGGITEVKDNDNSVDFC (SEQ ID NO: 51) | | | |
| RAE 15.6 | YTVTSDKDDDVANC (SEQ ID NO: 52) | | | |
| RAE 3.D | GKADWAENRC (SEQ ID NO: 53) | | | |
| RAE 28.1 | LENGAIFVASGVDPVLTPEQ (SEQ ID NO: 54) | | | |
| RAE 26.15 | GFFQVVNNNYDRWGTYA (SEQ ID NO: 55) | | | |

EXAMPLE 5

Antibody Binding to Recombinant Affinity Purified Amb a I, and Pollen Extract Derived Amb a I and Amb a II Affinity purified Amb a I was electrophoresed, Western transfered (Towbin et al., *Proc. Natl. Acad. Sci. USA*, 76: 4350 (1979)) and probea with a variety of antibodies, including IgE from an allergic patient (FIG. 17). In pollen extract Amb a I is not only present as an intact 38-KD species, but also characterized by its component 26-KD alpha chains and 12-KD beta chains which are formed by enzymatic cleavage. The intact 38-KD species and the alpha chain are clearly detected using rabbit anti-Amb a I, polyclonal affinity purified anti-RAE 16 and monoclonal anti-Amb a I JBIE3-4 (FIG. 17; RAE 16 peptide has the sequence RTDKDLLENGAIC derived from amino-acids 342–353 of Amb a IB, FIG. 16). Affinity purified Amb a I (partial sequence presented in Table 1) as well as chromatographically purified Amb a II (partial sequence presented in Table 2) are bound on Western blots by these antibodies as well as by patient IgE (FIG. 17). The goat anti-Amb a I polyclonal antibody also binds multiple Amb a I and Amb a II species on a two dimensional Western blot of pollen extract (FIG. 18). The Western blot was performed as outlined below.

Isoelectric focusing was done on a Hoeffer gel apparatus with 15 μg of crude soluble pollen protein. The gel consisted of 7.5% acrylamide with 3.5% Pharmalytes pH 4.5–5.3 (Pharmacia) and 3.5% Ampholines pH 3.5–10 (LKB), run at 13 W for 3.5 hours until a constant voltage was reached. The gel section was placed on a slab of 10% acrylamide SDS-PAGE and electrophoresed for 3.5 hours at 40 mA according to the protocol cited. The proteins were transferred overnight in phosphate buffer to 0.1 micron nitrocellulose (Schleicher and Schuell) at 0.2 A. The blot was rinsed in blot solution (25 mM Tris-HCl pH 7.5, 0.171M NaCl, 0.05% Tween-20; Sigma). The first antibody incubation was overnight at room temperature with a 1:000 dilution of goat anti-Amb a I IgG (obtained from Dr. David Marsh) in blot solution. The excess first antibody was removed with three 15 minute rinses with blot solution. The second antibody was a 1:2,500 dilution of biotinylated swine anti-goat IgG (Boehringer-Manneheim) in blot solution for two hours. The blot was then rinsed with blot solution three times for 15 minutes and incubated for 1 hr in blot solution with 2 μCi I$^{125}$ streptavidin (Amersham). The blots were rinsed with blot solution until the waste wash was down to background. The blot was then exposed to film at –80° C. overnight. In the case of one-dimensional SDS-PAGE Western blots (FIGS. 17, 19 and 20) the isoelectric focusing step was omitted. When human sera was used to probe the Western blots (FIGS. 17 and 20), 10% human plasma in 1% milk in blot solution was incubated overnight with the blot prior to using as second antibody biotinylated goat anti-human IgE.

Equivalents

Those skilled in the art will recognize, or be able to ascertain using no more than routine experimentation, many equivalents to the specific embodiments of the invention described specifically herein. Such equivalents are intended to be encompassed in the scope of the following claims.

Equivalents

Those skilled in the art will recognize, or be able to ascertain using no more than routine experimentation, many equivalents to the specific embodiments of the invention described specifically herein. Such equivalents are intended to be encompassed in the scope of the following claims.

---

SEQUENCE LISTING ( 1 ) GENERAL INFORMATION:

( i i i ) NUMBER OF SEQUENCES: 93

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:1:

Trp Glu Asn Phe Lys
    1                 5

( 2 ) INFORMATION FOR SEQ ID NO:2:

( i ) SEQUENCE CHARACTERISTICS:
        ( A ) LENGTH: 10 amino acids ( B ) TYPE: amino acid
( D ) TOPOLOGY: linear ( i i ) MOLECULE TYPE: peptide ( v ) FRAGMENT TYPE: internal ( x i ) SEQUENCE DESCRIPTION: SEQ ID NO:2:

Val Trp Val Lys Pro Trp Glu Asn Phe Lys
1               5                   10

( 2 ) INFORMATION FOR SEQ ID NO:3:

( i ) SEQUENCE CHARACTERISTICS:
( A ) LENGTH: 5 amino acids
( B ) TYPE: amino acid
( D ) TOPOLOGY: linear ( i i ) MOLECULE TYPE: peptide ( v ) FRAGMENT TYPE: internal ( x i ) SEQUENCE DESCRIPTION: SEQ ID NO:3:

Val Trp Val Lys Pro
1               5

( 2 ) INFORMATION FOR SEQ ID NO:4:

( i ) SEQUENCE CHARACTERISTICS:
( A ) LENGTH: 48 amino acids
( B ) TYPE: amino acid
( D ) TOPOLOGY: linear ( i i ) MOLECULE TYPE: peptide ( v ) FRAGMENT TYPE: internal ( x i ) SEQUENCE DESCRIPTION: SEQ ID NO:4:

Thr Ser Gly Ala Tyr Asn Ile Ile Asp Gly Cys Trp Arg Gly Lys Ala
1               5                   10                  15
Asp Trp Ala Glu Asn Arg Lys Ala Leu Ala Asp Cys Ala Gln Gly Phe
                20                  25                  30
Gly Lys Gly Thr Val Gly Gly Lys Asp Gly Asp Ile Tyr Thr Val Thr
            35                  40                  45

( 2 ) INFORMATION FOR SEQ ID NO:5:

( i ) SEQUENCE CHARACTERISTICS:
( A ) LENGTH: 33 amino acids
( B ) TYPE: amino acid
( D ) TOPOLOGY: linear ( i i ) MOLECULE TYPE: peptide ( v ) FRAGMENT TYPE: internal ( x i ) SEQUENCE DESCRIPTION: SEQ ID NO:5:

Thr Ser Gly Ala Tyr Asn Ile Ile Asp Gly Cys Trp Arg Gly Lys Ala
1               5                   10                  15
Asp Trp Ala Glu Asn Arg Lys Ala Leu Ala Asp Cys Ala Gln Gly Phe
                20                  25                  30
Gly ( 2 ) INFORMATION FOR SEQ ID NO:6:

( i ) SEQUENCE CHARACTERISTICS:
( A ) LENGTH: 33 amino acids
( B ) TYPE: amino acid ( D ) TOPOLOGY: linear ( i i ) MOLECULE TYPE: peptide ( v ) FRAGMENT TYPE: internal ( x i ) SEQUENCE DESCRIPTION: SEQ ID NO:6:

```
Asp  Ser  Gly  Ala  Tyr  Asn  Ile  Ile  Asp  Gly  Cys  Trp  Arg  Gly  Lys  Ala
1                   5                        10                       15

Asp  Trp  Ala  Glu  Asn  Ser  Arg  Ala  Leu  Ala  Asp  Cys  Ala  Gln  Gly  Phe
              20                        25                       30

Gly
```

( 2 ) INFORMATION FOR SEQ ID NO:7:

( i ) SEQUENCE CHARACTERISTICS:
 ( A ) LENGTH: 48 amino acids
 ( B ) TYPE: amino acid
 ( D ) TOPOLOGY: linear ( i i ) MOLECULE TYPE: peptide ( v ) FRAGMENT TYPE: internal ( x i ) SEQUENCE DESCRIPTION: SEQ ID NO:7:

```
Thr  Ser  Gly  Ala  Tyr  Asn  Ile  Ile  Asp  Gly  Cys  Trp  Arg  Gly  Lys  Ala
1                   5                        10                       15

Asp  Trp  Ala  Glu  Asn  Arg  Lys  Ala  Leu  Ala  Asp  Cys  Ala  Gln  Gly  Phe
              20                        25                       30

Gly  Lys  Gly  Thr  Val  Gly  Gly  Lys  Asp  Gly  Asp  Ile  Tyr  Thr  Val  Thr
          35                       40                       45
```

( 2 ) INFORMATION FOR SEQ ID NO:8:

( i ) SEQUENCE CHARACTERISTICS:
 ( A ) LENGTH: 16 amino acids
 ( B ) TYPE: amino acid
 ( D ) TOPOLOGY: linear ( i i ) MOLECULE TYPE: peptide ( v ) FRAGMENT TYPE: internal ( x i ) SEQUENCE DESCRIPTION: SEQ ID NO:8:

```
His  Asp  Val  Lys  Val  Asn  Pro  Gly  Gly  Leu  Ile  Lys  Ser  Asn  Asp  Gly
1                   5                        10                       15
```

( 2 ) INFORMATION FOR SEQ ID NO:9:

( i ) SEQUENCE CHARACTERISTICS:
 ( A ) LENGTH: 14 amino acids
 ( B ) TYPE: amino acid
 ( D ) TOPOLOGY: linear ( i i ) MOLECULE TYPE: peptide ( v ) FRAGMENT TYPE: internal ( x i ) SEQUENCE DESCRIPTION: SEQ ID NO:9:

```
Phe  Asp  Leu  Lys  Val  Asn  Ile  Gly  Gln  Leu  Ile  Lys  Ser  Asn
1                   5                        10
```

( 2 ) INFORMATION FOR SEQ ID NO:10:

( i ) SEQUENCE CHARACTERISTICS:
 ( A ) LENGTH: 14 amino acids
 ( B ) TYPE: amino acid
 ( D ) TOPOLOGY: linear ( i i ) MOLECULE TYPE: peptide ( v ) FRAGMENT TYPE: internal ( x i ) SEQUENCE DESCRIPTION: SEQ ID NO:10:

```
Phe Ala Phe Lys Asn Tyr Ile Pro Leu Leu Ile Asn Ser Asn
1               5                   10
```

( 2 ) INFORMATION FOR SEQ ID NO:11:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:11:

```
His Asp Val Lys Val Pro Gly Gly Leu Ile Lys Asn Gly
1               5                   10
```

( 2 ) INFORMATION FOR SEQ ID NO:12:

( i ) SEQUENCE CHARACTERISTICS:
        ( A ) LENGTH: 45 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:12:

```
Pro Arg Cys Arg His Gly Phe Phe Gln Val Val Asn Asn Asn Tyr Asp
1               5                   10                  15
Lys Trp Gly Ser Tyr Ala Ile Gly Gly Ser Ala Ser Pro Thr Ile Leu
                20                  25                  30
Ser Gln Gly Met Arg Phe Cys Ala Pro Asp Glu Arg Ser
            35                  40                  45
```

( 2 ) INFORMATION FOR SEQ ID NO:13:

( i ) SEQUENCE CHARACTERISTICS:
        ( A ) LENGTH: 42 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:13:

```
Pro Arg Cys Arg His Gly Phe Phe Gln Val Val Asn Asn Asn Tyr Asp
1               5                   10                  15
Arg Trp Gly Ser Tyr Ala Ile Gly Gly Ser Ala Pro Thr Ile Leu Ser
                20                  25                  30
Gln Gly Asn Phe Cys Ala Pro Asp Gly Tyr
            35                  40
```

( 2 ) INFORMATION FOR SEQ ID NO:14:

( i ) SEQUENCE CHARACTERISTICS:
        ( A ) LENGTH: 43 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:14:

```
Pro Arg Cys Arg Phe Gly Phe Phe Gln Ile Val Asn Asn Phe Tyr Asp
1               5                   10                  15
Arg Trp Asp His Tyr Ala Ile Gly Gly Ser Ala Asn Pro Thr Ile Leu
            20                  25                  30
Ser Gln Gly Asn Phe Val Ala Pro Asp Gly Tyr
        35              40
```

( 2 ) INFORMATION FOR SEQ ID NO:15:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:15:

```
Pro Val Leu Thr Pro Glu Gln Ser Ala Gly Met
1               5                   10
```

( 2 ) INFORMATION FOR SEQ ID NO:16:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:16:

```
Thr Ser Gly Ala Tyr Asn Ile Ile Asp Gly Cys Trp Arg Gly Lys Ala
1               5                   10                  15
Asp Trp Ala
```

( 2 ) INFORMATION FOR SEQ ID NO:17:

( i ) SEQUENCE CHARACTERISTICS:
        ( A ) LENGTH: 30 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:17:

```
Pro Arg Arg His Gly Phe Phe Gln Val Val Asn Asn Asn Tyr Asp Glu
1               5                   10                  15
Trp Gly Ser Tyr Ala Ile Gly Gly Ser Ala Ser Pro Thr Ile
            20                  25                  30
```

( 2 ) INFORMATION FOR SEQ ID NO:18:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:18:

```
Ala Trp Asn Trp Arg Thr Glu Lys Asp Leu
 1               5                   10
```

( 2 ) INFORMATION FOR SEQ ID NO:19:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:19:

```
Val Ile Asn Leu Asp Gln Glu Ile Phe Val
 1               5                   10
```

( 2 ) INFORMATION FOR SEQ ID NO:20:

( i ) SEQUENCE CHARACTERISTICS:
        ( A ) LENGTH: 37 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:20:

```
Pro Val Leu Thr Pro Glu Gln Ser Ala Gly Met Ile Pro Ala Glu Pro
 1               5                   10                  15
Gly Glu Ser Ala Leu Ser Leu Thr Ser Ser Ala Gly Val Leu Ser Cys
                20                  25                  30
Gln Pro Gly Ala Pro
                35
```

( 2 ) INFORMATION FOR SEQ ID NO:21:

( i ) SEQUENCE CHARACTERISTICS:
        ( A ) LENGTH: 18 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:21:

```
Pro Val Leu Asn Pro Glu Asn Ala Gly Met Ile Gln Ala Glu Pro Gly
 1               5                   10                  15
Glu Ala
```

( 2 ) INFORMATION FOR SEQ ID NO:22:

( i ) SEQUENCE CHARACTERISTICS:
        ( A ) LENGTH: 18 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:22:

Pro Val Ile Asn Pro Glu Asn Ala Gly Met Ile Gln Ala Glu Pro Gly
1               5                   10                  15

Glu Ala ( 2 ) INFORMATION FOR SEQ ID NO:23:

( i ) SEQUENCE CHARACTERISTICS:
      ( A ) LENGTH: 36 amino acids
      ( B ) TYPE: amino acid
      ( D ) TOPOLOGY: linear ( i i ) MOLECULE TYPE: peptide ( v ) FRAGMENT TYPE: internal ( x i ) SEQUENCE DESCRIPTION: SEQ ID NO:23:

Pro Val Leu Thr Pro Glu Gln Ser Ala Gly Met Ile Pro Ala Glu Pro
1               5                   10                  15

Gly Glu Ser Ala Leu Ser Leu Thr Ser Ala Gly Val Leu Cys Gln
              20                  25                  30

Pro Gly Ala Pro
          35

( 2 ) INFORMATION FOR SEQ ID NO:24:

( i ) SEQUENCE CHARACTERISTICS:
      ( A ) LENGTH: 26 amino acids
      ( B ) TYPE: amino acid
      ( D ) TOPOLOGY: linear ( i i ) MOLECULE TYPE: peptide ( v ) FRAGMENT TYPE: internal ( x i ) SEQUENCE DESCRIPTION: SEQ ID NO:24:

Pro Val Leu Thr Pro Val Gln Ser Ala Gly Met Ile Pro Ala Glu Pro
1               5                   10                  15

Gly Glu Ala Ala Ile Lys Leu Thr Ser Ser
              20                  25

( 2 ) INFORMATION FOR SEQ ID NO:25:

( i ) SEQUENCE CHARACTERISTICS:
      ( A ) LENGTH: 45 amino acids
      ( B ) TYPE: amino acid
      ( D ) TOPOLOGY: linear ( i i ) MOLECULE TYPE: peptide ( v ) FRAGMENT TYPE: internal ( x i ) SEQUENCE DESCRIPTION: SEQ ID NO:25:

Pro Arg Cys Arg Phe Gly Phe Phe Gln Ile Val Asn Asn Phe Tyr Asp
1               5                   10                  15

Arg Trp Asp Lys Tyr Ala Ile Gly Gly Ser Ser Asn Pro Thr Ile Leu
              20                  25                  30

Ser Gln Gly Asn Lys Phe Val Ala Pro Asp Phe Ile Tyr
          35                  40                  45

( 2 ) INFORMATION FOR SEQ ID NO:26:

( i ) SEQUENCE CHARACTERISTICS:
      ( A ) LENGTH: 43 amino acids
      ( B ) TYPE: amino acid
      ( D ) TOPOLOGY: linear ( i i ) MOLECULE TYPE: peptide ( v ) FRAGMENT TYPE: internal ( x i ) SEQUENCE DESCRIPTION: SEQ ID NO:26:

```
Pro Arg Arg Phe Gly Phe Phe Gln Ile Val Asn Asn Phe Tyr Asp Arg
1               5                   10                  15

Trp Asp His Tyr Ala Ile Gly Gly Ser Ser Asn Pro Thr Ile Leu Ser
            20                  25                  30

Gln Gly Asn Arg Phe Val Ala Pro Asp Ile Tyr
        35                  40
```

( 2 ) INFORMATION FOR SEQ ID NO:27:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:27:

```
Pro Val Leu Thr Pro Glu Gln Asn Ala Gly Met
1               5                   10
```

( 2 ) INFORMATION FOR SEQ ID NO:28:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:28:

```
Pro Arg Arg Phe Gly Phe Phe Gln Ile Val Asn Asn Phe Tyr Asp
1               5                   10                  15
```

( 2 ) INFORMATION FOR SEQ ID NO:29:

( i ) SEQUENCE CHARACTERISTICS:
        ( A ) LENGTH: 37 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:29:

```
Pro Val Leu Thr Ala Glu Gln Asn Ala Gly Met Met Gln Ala Glu Pro
1               5                   10                  15

Gly Asp Met Val Pro Gln Leu Thr Met Asn Ala Gly Val Leu Thr Cys
            20                  25                  30

Ser Pro Gly Ala Pro
        35
```

( 2 ) INFORMATION FOR SEQ ID NO:30:

( i ) SEQUENCE CHARACTERISTICS:
        ( A ) LENGTH: 35 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:30:

```
Pro Val Leu Thr Ala Glu Gln Asn Ala Gly Met Met Gln Ala Glu Pro
1               5                   10                  15

Gly Asp Met Val Pro Gln Leu Thr Met Asn Ala Gly Val Leu Ser Pro
            20                  25                  30

Gly Ala Pro
        35
```

( 2 ) INFORMATION FOR SEQ ID NO:31:

( i ) SEQUENCE CHARACTERISTICS:
        ( A ) LENGTH: 36 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:31:

```
Pro Val Leu Thr Ala Glu Gln Asn Ala Gly Met Met Gln Ala Glu Pro
1               5                   10                  15

Gly Asp Met Val Pro Gln Leu Thr Met Asn Ala Gly Val Leu Thr Ser
            20                  25                  30

Pro Gly Ala Pro
            35
```

( 2 ) INFORMATION FOR SEQ ID NO:32:

( i ) SEQUENCE CHARACTERISTICS:
        ( A ) LENGTH: 36 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:32:

```
Pro Val Leu Thr Pro Glu Gln Ser Ala Gly Met Ile Pro Ala Glu Pro
1               5                   10                  15

Gly Glu Ser Ala Leu Ser Leu Thr Ser Asn Ala Gly Val Leu Ser Ser
            20                  25                  30

Pro Gly Ala Pro
            35
```

( 2 ) INFORMATION FOR SEQ ID NO:33:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:33:

```
Cys Leu Arg Thr Gly Ala Gln Glu Pro Glu Trp Met Thr
1               5                   10
```

( 2 ) INFORMATION FOR SEQ ID NO:34:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:34:

```
Val  Trp  Val  Lys  Pro  Trp  Glu  Asn  Phe  Lys  Lys
1                   5                        10
```

( 2 ) INFORMATION FOR SEQ ID NO:35:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:35:

```
Trp  Glu  Asn  Phe  Lys  Lys
1                   5
```

( 2 ) INFORMATION FOR SEQ ID NO:36:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:36:

TGGGAAAATT TCAAAAAA                                                                                                           18

( 2 ) INFORMATION FOR SEQ ID NO:37:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:37:

TGGGAGAACT TTAAGAAG                                                                                                           18

( 2 ) INFORMATION FOR SEQ ID NO:38:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:38:

```
Trp  Glu  Asn  Phe  Lys  Glu
1                   5
```

( 2 ) INFORMATION FOR SEQ ID NO:39:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:39:

```
Val  Trp  Val  Lys  Pro
1                   5
```

( 2 ) INFORMATION FOR SEQ ID NO:40:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:40:

```
Glu  Phe  Pro  Ile  Leu  Gly  Gly  Ile  Thr  Glu  Val  Lys  Asp  Asn  Asp  Asn
1                   5                        10                       15
Ser  Val  Asp  Phe  Cys
                    20
```

( 2 ) INFORMATION FOR SEQ ID NO:41:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:41:

```
Leu  Tyr  Phe  Thr  Leu  Ala
1                   5
```

( 2 ) INFORMATION FOR SEQ ID NO:42:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:42:

GGGAATTCTT GTATTTTACC TTAGC                        25

( 2 ) INFORMATION FOR SEQ ID NO:43:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:43:

Asp Cys Ala Gln Gly Phe
1               5

( 2 ) INFORMATION FOR SEQ ID NO:44:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:44:

GGGAATTCGA CTGTGCCCAA GGTTTTG  27

( 2 ) INFORMATION FOR SEQ ID NO:45:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:45:

GGGCTGCAGT CATTATAAGT GCTTAGT  27

( 2 ) INFORMATION FOR SEQ ID NO:46:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:46:

GGGCTGCAGT GCTTAGCAAG GTGCTCC  27

( 2 ) INFORMATION FOR SEQ ID NO:47:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:47:

GGGCTGCAGC GTGTCCAAAT CTAATCAAAT GAACACTTAT GG  42

( 2 ) INFORMATION FOR SEQ ID NO:48:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:48:

```
Arg  Thr  Asp  Lys  Asp  Leu  Leu  Glu  Asn  Gly  Ala  Ile  Cys
1              5                        10
```

(2) INFORMATION FOR SEQ ID NO:49:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:49:

```
Leu  Asn  Gln  Glu  Leu  Val  Val  Asn  Ser  Asp  Lys  Thr  Ile  Asp  Gly  Arg
1              5                        10                       15

Gly  Val  Lys
```

(2) INFORMATION FOR SEQ ID NO:50:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:50:

```
Glu  Thr  Arg  Arg  Ser  Leu  Lys  Thr  Ser  Gly  Ala  Tyr  Asn  Ile  Ile  Asp
1              5                        10                       15

Gly  Cys  Trp  Arg  Gly  Lys  Ala  Asp
                20
```

(2) INFORMATION FOR SEQ ID NO:51:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:51:

```
Glu  Phe  Pro  Ile  Leu  Gly  Gly  Ile  Thr  Glu  Val  Lys  Asp  Asn  Asp  Asn
1              5                        10                       15

Ser  Val  Asp  Phe  Cys
                20
```

(2) INFORMATION FOR SEQ ID NO:52:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:52:

```
Tyr  Thr  Val  Thr  Ser  Asp  Lys  Asp  Asp  Val  Ala  Asn  Cys
1              5                        10
```

5,776,761

( 2 ) INFORMATION FOR SEQ ID NO:53:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:53:

```
Gly Lys Ala Asp Trp Ala Glu Asn Arg Cys
 1               5                   10
```

( 2 ) INFORMATION FOR SEQ ID NO:54:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:54:

```
Leu Glu Asn Gly Ala Ile Phe Val Ala Ser Gly Val Asp Pro Val Leu
 1               5                   10                  15
Thr Pro Glu Gln
            20
```

( 2 ) INFORMATION FOR SEQ ID NO:55:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:55:

```
Gly Phe Phe Gln Val Val Asn Asn Asn Tyr Asp Arg Trp Gly Thr Tyr
 1               5                   10                  15
Ala
```

( 2 ) INFORMATION FOR SEQ ID NO:56:

( i ) SEQUENCE CHARACTERISTICS:
        ( A ) LENGTH: 323 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..321

( x i ) SEQUENCE DESCRIPTION: SEQ ID NO:56:

```
GAA TTC GGC TGG AGA ACG AAT AAA GAC GTG CTT GAA AAT GGT GCT ATT    48
Glu Phe Gly Trp Arg Thr Asn Lys Asp Val Leu Glu Asn Gly Ala Ile
 1               5                   10                  15

TTT GTT GCA TCC GGG GTC GAT CCA GTG CTA ACC CCT GAG CAA AGC GCA    96
Phe Val Ala Ser Gly Val Asp Pro Val Leu Thr Pro Glu Gln Ser Ala
                20                  25                  30
```

| | | | | | | | | | | | | | | | | |
|---|---|---|---|---|---|---|---|---|---|---|---|---|---|---|---|---|
| GGG | ATG | ATT | CCA | GCC | GAA | CCA | GGA | GAG | TCC | GCT | CTA | AGC | CTC | ACT | AGT | 144 |
| Gly | Met | Ile | Pro | Ala | Glu | Pro | Gly | Glu | Ser | Ala | Leu | Ser | Leu | Thr | Ser | |
| | | 35 | | | | 40 | | | | | 45 | | | | | |
| AGT | GCT | GGT | GTA | CTC | TCA | TGC | CAA | CCC | GGA | GCA | CCT | TGC | TAA | GCA | CCC | 192 |
| Ser | Ala | Gly | Val | Leu | Ser | Cys | Gln | Pro | Gly | Ala | Pro | Cys | * | Ala | Pro | |
| | 50 | | | | 55 | | | | | 60 | | | | | | |
| GAC | CAA | TTA | CTA | AGC | ACT | TAT | AAT | GAT | CAT | TAA | TAC | TTT | TTT | TTA | TTT | 240 |
| Asp | Gln | Leu | Leu | Ser | Thr | Tyr | Asn | Asp | His | * | Tyr | Phe | Phe | Leu | Phe | |
| 65 | | | | | 70 | | | | | 75 | | | | | 80 | |
| TAT | TTT | TGA | TAT | TTT | ATA | TGT | ACT | AAG | GTA | ATG | GAA | ATG | AAC | CTT | TAC | 288 |
| Tyr | Phe | * | Tyr | Phe | Ile | Cys | Thr | Lys | Val | Met | Glu | Met | Asn | Leu | Tyr | |
| | | | | 85 | | | | | 90 | | | | | 95 | | |
| CTT | CTA | GTA | CTC | TAA | AAA | AAA | AAA | AAA | CCG | AAT | TC | | | | | 323 |
| Leu | Leu | Val | Leu | * | Lys | Lys | Lys | Lys | Pro | Asn | | | | | | |
| | | | 100 | | | | | 105 | | | | | | | | |

( 2 ) INFORMATION FOR SEQ ID NO:57:

( i ) SEQUENCE CHARACTERISTICS:
        ( A ) LENGTH: 61 amino acids
        ( B ) TYPE: amino acid
        ( D ) TOPOLOGY: linear ( i i ) MOLECULE TYPE: protein ( x i ) SEQUENCE DESCRIPTION: SEQ ID NO:57:

| | | | | | | | | | | | | | | | |
|---|---|---|---|---|---|---|---|---|---|---|---|---|---|---|---|
| Glu | Phe | Gly | Trp | Arg | Thr | Asn | Lys | Asp | Val | Leu | Glu | Asn | Gly | Ala | Ile |
| 1 | | | | 5 | | | | | 10 | | | | | 15 | |
| Phe | Val | Ala | Ser | Gly | Val | Asp | Pro | Val | Leu | Thr | Pro | Glu | Gln | Ser | Ala |
| | | | 20 | | | | | 25 | | | | | 30 | | |
| Gly | Met | Ile | Pro | Ala | Glu | Pro | Gly | Glu | Ser | Ala | Leu | Ser | Leu | Thr | Ser |
| | | 35 | | | | | 40 | | | | | 45 | | | |
| Ser | Ala | Gly | Val | Leu | Ser | Cys | Gln | Pro | Gly | Ala | Pro | Cys | | | |
| | 50 | | | | | 55 | | | | | 60 | | | | |

( 2 ) INFORMATION FOR SEQ ID NO:58:

( i ) SEQUENCE CHARACTERISTICS:
        ( A ) LENGTH: 1328 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..1328

( x i ) SEQUENCE DESCRIPTION: SEQ ID NO:58:

| | | | | | | | | | | | | | | | | |
|---|---|---|---|---|---|---|---|---|---|---|---|---|---|---|---|---|
| TAC | ATC | TTG | TAT | TTT | ACC | TTA | GCC | CTT | GTC | ACT | TTG | CTG | CAA | CCT | GTT | 48 |
| Tyr | Ile | Leu | Tyr | Phe | Thr | Leu | Ala | Leu | Val | Thr | Leu | Leu | Gln | Pro | Val | |
| 1 | | | | 5 | | | | | 10 | | | | | 15 | | |
| CGT | TCT | GCA | GAA | GAT | GTT | GAA | GAA | TTC | TTA | CCT | TCA | GCT | AAC | GAA | ACA | 96 |
| Arg | Ser | Ala | Glu | Asp | Val | Glu | Glu | Phe | Leu | Pro | Ser | Ala | Asn | Glu | Thr | |
| | | | 20 | | | | | 25 | | | | | 30 | | | |
| AGG | AGG | AGC | CTG | AAA | GCA | TGT | GAA | GCA | CAC | AAC | ATT | ATA | GAC | AAG | TGC | 144 |
| Arg | Arg | Ser | Leu | Lys | Ala | Cys | Glu | Ala | His | Asn | Ile | Ile | Asp | Lys | Cys | |
| | | 35 | | | | 40 | | | | | 45 | | | | | |
| TGG | AGG | TGC | AAA | GCC | GAT | TGG | GCG | AAT | AAC | CGA | CAA | GCG | TTA | GCC | GAT | 192 |
| Trp | Arg | Cys | Lys | Ala | Asp | Trp | Ala | Asn | Asn | Arg | Gln | Ala | Leu | Ala | Asp | |
| | | 50 | | | | 55 | | | | | 60 | | | | | |
| TGT | GCC | CAA | GGT | TTT | GCA | AAG | GGA | ACC | TAC | GGT | GGA | AAA | CAT | GGT | GAT | 240 |
| Cys | Ala | Gln | Gly | Phe | Ala | Lys | Gly | Thr | Tyr | Gly | Gly | Lys | His | Gly | Asp | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| GTC | TAC | ACG | GTC | ACC | AGT | GAT | AAA | GAT | GAT | GAT | GTT | GCA | AAT | CCA | AAA | 288 |
| Val | Tyr | Thr | Val | Thr 85 | Ser | Asp | Lys | Asp 90 | Asp | Asp | Val | Ala | Asn | Pro 95 | Lys | |
| GAA | GGC | ACA | CTC | CGG | TTT | GCT | GCT | GCC | CAA | AAC | AGG | CCC | TTG | TGG | ATC | 336 |
| Glu | Gly | Thr | Leu 100 | Arg | Phe | Ala | Ala | Ala 105 | Gln | Asn | Arg | Pro | Leu 110 | Trp | Ile | |
| ATT | TTT | AAA | AGA | AAT | ATG | GTG | ATT | CAT | TTG | AAT | CAA | GAG | CTT | GTC | GTA | 384 |
| Ile | Phe | Lys 115 | Arg | Asn | Met | Val | Ile 120 | His | Leu | Asn | Gln | Glu 125 | Leu | Val | Val | |
| AAC | AGC | GAC | AAG | ACC | ATC | GAT | GGC | CGA | GGG | GTG | AAA | GTT | AAC | ATC | GTT | 432 |
| Asn | Ser 130 | Asp | Lys | Thr | Ile | Asp 135 | Gly | Arg | Gly | Val | Lys 140 | Val | Asn | Ile | Val | |
| AAC | GCC | GGT | CTC | ACC | CTC | ATG | AAT | GTC | AAG | AAT | ATA | ATC | ATT | CAT | AAC | 480 |
| Asn | Ala | Gly | Leu | Thr 150 | Leu | Met | Asn | Val | Lys 155 | Asn | Ile | Ile | Ile | His | Asn 160 | |
| Asn 145 | | | | | | | | | | | | | | | | |
| ATA | AAT | ATC | CAT | GAT | ATT | AAA | GTT | TGT | CCA | GGA | GGC | ATG | ATT | AAG | TCC | 528 |
| Ile | Asn | Ile | His | Asp 165 | Ile | Lys | Val | Cys | Pro 170 | Gly | Gly | Met | Ile | Lys 175 | Ser | |
| AAC | GAT | GGT | CCA | CCA | ATT | TTA | AGA | CAA | CAA | AGT | GAT | GGT | GAT | GCT | ATA | 576 |
| Asn | Asp | Gly | Pro 180 | Pro | Ile | Leu | Arg | Gln 185 | Gln | Ser | Asp | Gly | Asp 190 | Ala | Ile | |
| AAT | GTT | GCT | GGT | AGT | TCA | CAA | ATA | TGG | ATC | GAC | CAT | TGC | TCG | CTC | AGT | 624 |
| Asn | Val | Ala 195 | Gly | Ser | Ser | Gln | Ile 200 | Trp | Ile | Asp | His | Cys 205 | Ser | Leu | Ser | |
| AAG | GCT | TCC | GAT | GGG | CTG | CTC | GAT | ATC | ACC | CTC | GGC | AGC | TCA | CAC | GTG | 672 |
| Lys | Ala | Ser | Asp 210 | Gly | Leu | Leu | Asp | Ile 215 | Thr | Leu | Gly | Ser | Ser 220 | His | Val | |
| ACC | GTT | TCC | AAC | TGC | AAA | TTC | ACC | CAA | CAC | CAA | TTT | GTA | TTA | TTG | CTC | 720 |
| Thr | Val | Ser | Asn | Cys 230 | Lys | Phe | Thr | Gln | His 235 | Gln | Phe | Val | Leu | Leu 240 | Leu | |
| Thr 225 | | | | | | | | | | | | | | | | |
| GGG | GCT | GAT | GAC | ACC | CAT | TAT | CAA | GAT | AAA | GGC | ATG | CTA | GCA | ACG | GTA | 768 |
| Gly | Ala | Asp | Asp | Thr 245 | His | Tyr | Gln | Asp | Lys 250 | Gly | Met | Leu | Ala | Thr 255 | Val | |
| GCA | TTC | AAC | ATG | TTC | ACC | GAT | CAC | GTT | GAC | CAA | AGA | ATG | CCT | AGA | TGT | 816 |
| Ala | Phe | Asn | Met 260 | Phe | Thr | Asp | His | Val 265 | Asp | Gln | Arg | Met | Pro 270 | Arg | Cys | |
| AGA | TTT | GGG | TTT | TTC | CAA | GTC | GTT | AAC | AAC | AAC | TAC | GAC | AGA | TGG | GGA | 864 |
| Arg | Phe | Gly 275 | Phe | Phe | Gln | Val | Val 280 | Asn | Asn | Asn | Tyr | Asp 285 | Arg | Trp | Gly | |
| ACG | TAC | GCC | ATC | GGT | GGT | AGC | TCG | GCC | CCA | ACT | ATA | CTC | AGC | CAA | GGG | 912 |
| Thr | Tyr | Ala | Ile | Gly 295 | Gly | Ser | Ser | Ala | Pro 300 | Thr | Ile | Leu | Ser | Gln | Gly | |
| Thr 290 | | | | | | | | | | | | | | | | |
| AAC | AGA | TTC | TTC | GCC | CCC | GAT | GAT | ATC | ATC | AAG | GAA | AAT | GTC | TTA | GCG | 960 |
| Asn | Arg | Phe | Phe | Ala 310 | Pro | Asp | Asp | Ile | Ile 315 | Lys | Glu | Asn | Val | Leu 320 | Ala | |
| Asn 305 | | | | | | | | | | | | | | | | |
| AGG | ACT | GGT | ACT | GGC | AAC | GCA | GAG | TCG | ATG | TCG | TGG | AAC | TGG | AGA | ACA | 1008 |
| Arg | Thr | Gly | Thr | Gly 325 | Asn | Ala | Glu | Ser | Met 330 | Ser | Trp | Asn | Trp | Arg 335 | Thr | |
| GAT | AAA | GAC | TTG | CTT | GAA | AAT | GGT | GCT | ATT | TTT | CTC | CCA | TCC | GGG | TCT | 1056 |
| Asp | Lys | Asp | Leu 340 | Leu | Glu | Asn | Gly | Ala 345 | Ile | Phe | Leu | Pro | Ser 350 | Gly | Ser | |
| GAT | CCA | GTG | CTA | ACC | CCT | GAG | CAA | AAA | GCA | GGG | ATG | ATT | CCA | GCT | GAA | 1104 |
| Asp | Pro | Val 355 | Leu | Thr | Pro | Glu | Gln 360 | Lys | Ala | Gly | Met | Ile 365 | Pro | Ala | Glu | |
| CCA | GGA | GAA | GCC | GTT | CTA | AGA | CTC | ACT | AGT | AGT | GCT | GGT | GTA | CTC | TCA | 1152 |
| Pro | Gly 370 | Glu | Ala | Val | Leu | Arg 375 | Leu | Thr | Ser | Ser | Ala 380 | Gly | Val | Leu | Ser | |
| TGC | CAT | CAA | GGA | GCA | CCT | TGC | TAA | GCA | CCT | GGC | CAA | TTC | CTA | AGC | TTT | 1200 |
| Cys | His | Gln | Gly | Ala 390 | Pro | Cys | * | Ala | Pro 395 | Gly | Gln | Phe | Leu | Ser 400 | Phe | |
| Cys 385 | | | | | | | | | | | | | | | | |

| | | | | | | | | | | | | | | | | |
|---|---|---|---|---|---|---|---|---|---|---|---|---|---|---|---|---|
| TAT | AAT | AAT | CAT | AAA | TAC | TTA | TTT | TAT | TTT | ATT | TTT | GAT | ATT | TTA | TAT | 1248 |
| Tyr | Asn | Asn | His | Lys<br>405 | Tyr | Leu | Phe | Tyr<br>410 | Phe | Ile | Phe | Asp | Ile | Leu<br>415 | Tyr | |
| GAA | CCA | TTA | CGT | TCA | AGT | ACT | CTA | TTA | ACA | TGT | TTT | AAA | TTC | ATA | AGA | 1296 |
| Glu | Pro | Leu | Arg<br>420 | Ser | Ser | Thr | Leu | Leu<br>425 | Thr | Cys | Phe | Lys | Phe<br>430 | Ile | Arg | |
| GTT | TAT | TGA | TAA | AAA | AAA | AAA | AAA | CCG | AAT | TC | | | | | | 1328 |
| Val | Tyr | *<br>435 | * | Lys | Lys | Lys | Lys<br>440 | Pro | Asn | | | | | | | |

( 2 ) INFORMATION FOR SEQ ID NO:59:

( i ) SEQUENCE CHARACTERISTICS:
      ( A ) LENGTH: 391 amino acids
      ( B ) TYPE: amino acid
      ( D ) TOPOLOGY: linear ( i i ) MOLECULE TYPE: protein ( x i ) SEQUENCE DESCRIPTION: SEQ ID NO:59:

| | | | | | | | | | | | | | | |
|---|---|---|---|---|---|---|---|---|---|---|---|---|---|---|
| Tyr<br>1 | Ile | Leu | Tyr | Phe<br>5 | Thr | Leu | Ala | Leu | Val<br>10 | Thr | Leu | Leu | Gln | Pro<br>15 | Val |
| Arg | Ser | Ala | Glu<br>20 | Asp | Val | Glu | Glu | Phe<br>25 | Leu | Pro | Ser | Ala | Asn<br>30 | Glu | Thr |
| Arg | Arg | Ser<br>35 | Leu | Lys | Ala | Cys | Glu<br>40 | Ala | His | Asn | Ile | Ile<br>45 | Asp | Lys | Cys |
| Trp | Arg<br>50 | Cys | Lys | Ala | Asp | Trp<br>55 | Ala | Asn | Asn | Arg | Gln<br>60 | Ala | Leu | Ala | Asp |
| Cys<br>65 | Ala | Gln | Gly | Phe<br>70 | Ala | Lys | Gly | Thr | Tyr<br>75 | Gly | Gly | Lys | His | Gly<br>80 | Asp |
| Val | Tyr | Thr | Val | Thr<br>85 | Ser | Asp | Lys | Asp | Asp<br>90 | Val | Ala | Asn | Pro<br>95 | Lys | |
| Glu | Gly | Thr | Leu<br>100 | Arg | Phe | Ala | Ala | Ala<br>105 | Gln | Asn | Arg | Pro | Leu<br>110 | Trp | Ile |
| Ile | Phe | Lys<br>115 | Arg | Asn | Met | Val | Ile<br>120 | His | Leu | Asn | Gln | Glu<br>125 | Leu | Val | Val |
| Asn | Ser<br>130 | Asp | Lys | Thr | Ile | Asp<br>135 | Gly | Arg | Gly | Val | Lys<br>140 | Val | Asn | Ile | Val |
| Asn<br>145 | Ala | Gly | Leu | Thr | Leu<br>150 | Met | Asn | Val | Lys | Asn<br>155 | Ile | Ile | His | Asn<br>160 | |
| Ile | Asn | Ile | His | Asp<br>165 | Ile | Lys | Val | Cys | Pro<br>170 | Gly | Gly | Met | Ile | Lys<br>175 | Ser |
| Asn | Asp | Gly | Pro<br>180 | Pro | Ile | Leu | Arg | Gln<br>185 | Gln | Ser | Asp | Gly | Asp<br>190 | Ala | Ile |
| Asn | Val | Ala<br>195 | Gly | Ser | Ser | Gln | Ile<br>200 | Trp | Ile | Asp | His | Cys<br>205 | Ser | Leu | Ser |
| Lys | Ala<br>210 | Ser | Asp | Gly | Leu | Leu<br>215 | Asp | Ile | Thr | Leu | Gly<br>220 | Ser | Ser | His | Val |
| Thr<br>225 | Val | Ser | Asn | Cys | Lys<br>230 | Phe | Thr | Gln | His | Gln<br>235 | Phe | Val | Leu | Leu<br>240 | Leu |
| Gly | Ala | Asp | Asp | Thr<br>245 | His | Tyr | Gln | Asp | Lys<br>250 | Gly | Met | Leu | Ala | Thr<br>255 | Val |
| Ala | Phe | Asn | Met<br>260 | Phe | Thr | Asp | His | Val<br>265 | Asp | Gln | Arg | Met | Pro<br>270 | Arg | Cys |
| Arg | Phe | Gly<br>275 | Phe | Phe | Gln | Val | Val<br>280 | Asn | Asn | Asn | Tyr | Asp<br>285 | Arg | Trp | Gly |
| Thr | Tyr | Ala | Ile | Gly | Gly | Ser | Ser | Ala | Pro | Thr | Ile | Leu | Ser | Gln | Gly |

```
                  290                     295                      300
Asn  Arg  Phe  Phe  Ala  Pro  Asp  Ile  Ile  Lys  Glu  Asn  Val  Leu  Ala
305                      310                      315                     320

Arg  Thr  Gly  Thr  Gly  Asn  Ala  Glu  Ser  Met  Ser  Trp  Asn  Trp  Arg  Thr
                    325                      330                     335

Asp  Lys  Asp  Leu  Leu  Glu  Asn  Gly  Ala  Ile  Phe  Leu  Pro  Ser  Gly  Ser
               340                      345                                350

Asp  Pro  Val  Leu  Thr  Pro  Glu  Gln  Lys  Ala  Gly  Met  Ile  Pro  Ala  Glu
          355                      360                     365

Pro  Gly  Glu  Ala  Val  Leu  Arg  Leu  Thr  Ser  Ser  Ala  Gly  Val  Leu  Ser
     370                      375                     380

Cys  His  Gln  Gly  Ala  Pro  Cys
385                      390
```

( 2 ) INFORMATION FOR SEQ ID NO:60:

( i ) SEQUENCE CHARACTERISTICS:
        ( A ) LENGTH: 324 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..300

( x i ) SEQUENCE DESCRIPTION: SEQ ID NO:60:

```
GAA  TTC  GGC  TGG  AGA  ACG  AAT  AAA  GAC  GTG  CTT  GAA  AAT  GGT  GCT  ATT       48
Glu  Phe  Gly  Trp  Arg  Thr  Asn  Lys  Asp  Val  Leu  Glu  Asn  Gly  Ala  Ile
  1                 5                      10                      15

TTT  GTT  GCA  TCC  GGG  GTC  GAT  CCA  GTG  CTA  ACC  CCT  GAG  CAA  AGC  GCA       96
Phe  Val  Ala  Ser  Gly  Val  Asp  Pro  Val  Leu  Thr  Pro  Glu  Gln  Ser  Ala
                     20                      25                      30

GGG  ATG  ATT  CCA  GCC  GAA  CCA  GGA  GAG  TCC  GCT  CTA  AGC  CTC  ACT  AGT      144
Gly  Met  Ile  Pro  Ala  Glu  Pro  Gly  Glu  Ser  Ala  Leu  Ser  Leu  Thr  Ser
                35                      40                      45

AGT  GCT  GGT  GTA  CTC  TCA  TGC  CAA  CCC  GGA  GCA  CCT  TGC  TAA  GCA  CCC      192
Ser  Ala  Gly  Val  Leu  Ser  Cys  Gln  Pro  Gly  Ala  Pro  Cys   *   Ala  Pro
           50                      55                      60

GAC  CAA  TTA  CTA  AGC  ACT  TAT  AAT  GAT  CAT  TAA  TAC  TTT  TTT  TTA  TTT      240
Asp  Gln  Leu  Leu  Ser  Thr  Tyr  Asn  Asp  His   *   Tyr  Phe  Phe  Leu  Phe
 65                      70                      75                      80

TAT  TTT  TGA  TAT  TTT  ATA  TGT  ACT  AAG  GTA  ATG  GAA  ATG  AAC  CTT  TAC      288
Tyr  Phe   *   Tyr  Phe  Ile  Cys  Thr  Lys  Val  Met  Glu  Met  Asn  Leu  Tyr
                     85                      90                      95

CTT  CTT  AGT  ACT  CTAAAAAAAA  AAAAAACCGA  ATTC                                     324
Leu  Leu  Ser  Thr
               100
```

( 2 ) INFORMATION FOR SEQ ID NO:61:

( i ) SEQUENCE CHARACTERISTICS:
        ( A ) LENGTH: 61 amino acids
        ( B ) TYPE: amino acid
        ( D ) TOPOLOGY: linear ( i i ) MOLECULE TYPE: protein ( x i ) SEQUENCE DESCRIPTION: SEQ ID NO:61:

```
Glu  Phe  Gly  Trp  Arg  Thr  Asn  Lys  Asp  Val  Leu  Glu  Asn  Gly  Ala  Ile
  1                 5                      10                      15
```

| Phe | Val | Ala | Ser | Gly | Val | Asp | Pro | Val | Leu | Thr | Pro | Glu | Gln | Ser | Ala |
|---|---|---|---|---|---|---|---|---|---|---|---|---|---|---|---|
| | | | 20 | | | | 25 | | | | | 30 | | | |

| Gly | Met | Ile | Pro | Ala | Glu | Pro | Gly | Glu | Ser | Ala | Leu | Ser | Leu | Thr | Ser |
|---|---|---|---|---|---|---|---|---|---|---|---|---|---|---|---|
| | | 35 | | | | 40 | | | | | 45 | | | | |

| Ser | Ala | Gly | Val | Leu | Ser | Cys | Gln | Pro | Gly | Ala | Pro | Cys |
|---|---|---|---|---|---|---|---|---|---|---|---|---|
| | 50 | | | | | 55 | | | | | 60 | |

( 2 ) INFORMATION FOR SEQ ID NO:62:

( i ) SEQUENCE CHARACTERISTICS:
        ( A ) LENGTH: 452 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:62:

```
GAATTCCGAT  TCTTGGAGGA  ATTACCGAAG  TTAAAGACAA  TGATAACAGC  GTCGATTTCG    60
ACGAGCTTGC  TAAATTCGCC  ATCGCTGAAC  ACAACAAGAA  GGAGAATGCT  GCTCTGGAGT   120
TTGGAAAAGT  AATAGAAAAA  AAGCAGCAGG  CGGTACAGGG  CACCATGTAT  TATATAAAAG   180
TGGAAGCAAA  TGATGGTGGT  GAGAAGAAAA  CTTATGAAGC  CAAGGTGTGG  GTTAAGCTAT   240
GGGAAAATTT  CAAGGAATTG  CAGGAACTCA  AACTTGTTTG  ATGGACGGGT  GTGTGCTATG   300
ACAAAATAGC  TCGAGCAGGT  GAAGCATGAA  TGTATAAATA  TTCTTTTTAA  GTTAATAAT    360
AAACATTTCT  TGTAATATGG  TACAGGTTTA  TGTACTTTGG  TATGTATAAC  AGAAAACATA   420
TCATAAATTC  AAACTTAGAA  TTTTGGGAAT  TC                                  452
```

( 2 ) INFORMATION FOR SEQ ID NO:63:

( i ) SEQUENCE CHARACTERISTICS:
        ( A ) LENGTH: 452 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:63:

```
GAATTCCCAA  AATTCTAAGT  TTGAATTTAT  GATATGTTTT  CTGTTATACA  TACCAAAGTA    60
CATAAACCTG  TACCATATTA  CAAGAAATGT  TTATTATTAA  ACTTAAAAAG  AATATTTATA   120
CATTCATGCT  TCACCTGCTC  GAGCTATTTT  GTCATAGCAC  ACACCCGTCC  ATCAAACAAG   180
TTTGAGTTCC  TGCAATTCCT  TGAAATTTTC  CCATAGCTTA  ACCCACACCT  TGGCTTCATA   240
AGTTTCTTC   TCACCACCAT  CATTTGCTTC  CACTTTTATA  TAATACATGG  TGCCCTGTAC   300
CGCCTGCTGC  TTTTTTTCTA  TTACTTTTCC  AAACTCCAGA  GCAGCATTCT  CCTTCTTGTT   360
GTGTTCAGCG  ATGGCGAATT  TAGCAAGCTC  GTCGAAATCG  ACGCTGTTAT  CATTGTCTTT   420
AACTTCGGTA  ATTCCTCCAA  GAATCGGAAT  TC                                  452
```

( 2 ) INFORMATION FOR SEQ ID NO:64:

( i ) SEQUENCE CHARACTERISTICS:
        ( A ) LENGTH: 488 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:64:

-continued

```
GAATTCCCGA TTCTTGGAGG AATTACCGAA GTTAAAGACA ATGATAACAG CGTCGATTTC     60
GACGAGCTTG CTAAATTCGC CATCACTGAA CACAACAAGA AGGAGAATGC TGCTCTGGAG    120
TTTGGAAAAG TAATAGAAAA AAAGCAGCAG GCGGTACAGG GCACCATGTA TTATATAAAA    180
GCGGAAGCAA ATGATGGTGG TGAGAAGAAA ACTTATGAAG CCAAGGTGTG GGTTAAGCTA    240
TGGGAAAATT TCAAGGAATT TGCAAGGAAC TCAAACCTTG TTTGATGATG CCACCTCACC    300
TTAACTCCAT ATGGACGGTG TGCTATGACA AAATAGCTCA AGGAGGTGAA GCATAAATGT    360
ATAAATATTC TTTTTAAGTT TAATAATAAA CATTTCTTGT AATATAGTAC AAGTTTATGT    420
ACTTTGGTAT GTATAACAGA AAACATATCA TAAATTCAAA CTTAATGTTT TTTTTCTCG    480
CGGAATTC                                                             488
```

( 2 ) INFORMATION FOR SEQ ID NO:65:

( i ) SEQUENCE CHARACTERISTICS:
        ( A ) LENGTH: 488 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:65:

```
GAATTCCGCG AGAAAAAAAA ACATTAAGTT TGAATTTATG ATATGTTTTC TGTTATACAT     60
ACCAAAGTAC ATAAACTTGT ACTATATTAC AAGAAATGTT TATTATTAAA CTTAAAAAGA    120
ATATTTATAC ATTTATGCTT CACCTCCTTG AGCTATTTTG TCATAGCACA CCGTCCATAT    180
GGAGTTAAGG TGAGGTGGCA TCATCAAACA AGGTTTGAGT TCCTTGCAAA TTCCTTGAAA    240
TTTTCCCATA GCTTAACCCA CACCTTGGCT TCATAAGTTT TCTTCTCACC ACCATCATTT    300
GCTTCCGCTT TTATATAATA CATGGTGCCC TGTACCGCCT GCTGCTTTTT TTCTATTACT    360
TTTCCAAACT CCAGAGCAGC ATTCTCCTTC TTGTTGTGTT CAGTGATGGC GAATTTAGCA    420
AGCTCGTCGA AATCGACGCT GTTATCATTG TCTTTAACTT CGGTAATTCC TCCAAGAATC    480
GGGAATTC                                                             488
```

( 2 ) INFORMATION FOR SEQ ID NO:66:

( i ) SEQUENCE CHARACTERISTICS:
        ( A ) LENGTH: 190 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:66:

```
TCGATTCGCT GTCGATGAAC ACAACAAGAA GCAGAATACC CTGCTGGAAT TTAAGAAGGT     60
ACTGAATACA AAGGAGCAGG TAGTAGCTGG TATAATGTAT TATATCACAC TTGAAGCAAC    120
TGATGGTGGT GAGAAAAAGA CTTATGAAGC CAAGGTTTGG GTTAAGCCAT GGGAAAACTT    180
CAAAGAATTC                                                            190
```

( 2 ) INFORMATION FOR SEQ ID NO:67:

( i ) SEQUENCE CHARACTERISTICS:
        ( A ) LENGTH: 190 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:67:

GAATTCTTTG AAGTTTTCCC ATGGCTTAAC CCAAACCTTG GCTTCATAAG TCTTTTTCTC    60

ACCACCATCA GTTGCTTCAA GTGTGATATA ATACATTATA CCAGCTACTA CCTGCTCCTT   120

TGTATTCAGT ACCTTCTTAA ATTCCAGCAG GGTATTCTGC TTCTTGTTGT GTTCATCGAC   180

AGCGAATCGA                                                         190

( 2 ) INFORMATION FOR SEQ ID NO:68:

( i ) SEQUENCE CHARACTERISTICS:
    ( A ) LENGTH: 92 amino acids
    ( B ) TYPE: amino acid
    ( D ) TOPOLOGY: linear ( i i ) MOLECULE TYPE: peptide ( v ) FRAGMENT TYPE: internal ( x i ) SEQUENCE DESCRIPTION: SEQ ID NO:68:

Ile Pro Ile Leu Gly Gly Ile Thr Glu Val Lys Asp Asn Asp Asn Ser
1               5                   10                  15

Val Asp Phe Asp Glu Leu Ala Lys Phe Ala Ile Ala Glu His Asn Lys
            20                  25                  30

Lys Glu Asn Ala Ala Leu Glu Phe Gly Lys Val Ile Glu Lys Lys Gln
        35                  40                  45

Gln Ala Val Gln Gly Thr Met Tyr Tyr Ile Lys Val Glu Ala Asn Asp
    50                  55                  60

Gly Gly Glu Lys Lys Thr Tyr Glu Ala Lys Val Trp Val Lys Leu Trp
65                  70                  75                  80

Glu Asn Phe Lys Glu Leu Gln Glu Leu Lys Leu Val
                85                  90

( 2 ) INFORMATION FOR SEQ ID NO:69:

( i ) SEQUENCE CHARACTERISTICS:
    ( A ) LENGTH: 94 amino acids
    ( B ) TYPE: amino acid
    ( D ) TOPOLOGY: linear ( i i ) MOLECULE TYPE: peptide ( v ) FRAGMENT TYPE: internal ( x i ) SEQUENCE DESCRIPTION: SEQ ID NO:69:

Glu Phe Pro Ile Leu Gly Gly Ile Thr Glu Val Lys Asp Asn Asp Asn
1               5                   10                  15

Ser Val Asp Phe Asp Glu Leu Ala Lys Phe Ala Ile Thr Glu His Asn
            20                  25                  30

Lys Lys Glu Asn Ala Ala Leu Glu Phe Gly Lys Val Ile Glu Lys Lys
        35                  40                  45

Gln Gln Ala Val Gln Gly Thr Met Tyr Tyr Ile Lys Ala Glu Ala Asn
    50                  55                  60

Asp Gly Gly Glu Lys Lys Thr Tyr Glu Ala Lys Val Trp Val Lys Leu
65                  70                  75                  80

Trp Glu Asn Phe Lys Glu Phe Ala Arg Asn Ser Asn Leu Val
                85                  90

( 2 ) INFORMATION FOR SEQ ID NO:70:

( i ) SEQUENCE CHARACTERISTICS:
    ( A ) LENGTH: 60 amino acids (B) TYPE: amino acid
(D) TOPOLOGY: linear (ii) MOLECULE TYPE: peptide (v) FRAGMENT TYPE: internal (xi) SEQUENCE DESCRIPTION: SEQ ID NO:70:

```
Val Asp Glu His Asn Lys Lys Gln Asn Thr Leu Leu Glu Phe Lys Lys
 1               5                  10                  15

Val Leu Asn Thr Lys Glu Gln Val Val Ala Gly Ile Met Tyr Tyr Ile
            20                  25                  30

Thr Leu Glu Ala Thr Asp Gly Gly Glu Lys Lys Thr Tyr Glu Ala Lys
        35                  40                  45

Val Trp Val Lys Pro Trp Glu Asn Phe Lys Glu Phe
    50                  55                  60
```

(2) INFORMATION FOR SEQ ID NO:71:

(i) SEQUENCE CHARACTERISTICS:
  (A) LENGTH: 1196 base pairs
  (B) TYPE: nucleic acid
  (C) STRANDEDNESS: single
  (D) TOPOLOGY: linear (ii) MOLECULE TYPE: cDNA (ix) FEATURE:
  (A) NAME/KEY: CDS
  (B) LOCATION: 1..1161

(xi) SEQUENCE DESCRIPTION: SEQ ID NO:71:

```
TTG TAT TTT ACC TTA GCC CTT GTC ACT TTG CTG CAA CCT GTT CGT TCT      48
Leu Tyr Phe Thr Leu Ala Leu Val Thr Leu Leu Gln Pro Val Arg Ser
 1               5                  10                  15

GCC GAA GAT CTC CAG GAA ATC TTA CCA GTT AAC GAA ACA AGG AGG CTG      96
Ala Glu Asp Leu Gln Glu Ile Leu Pro Val Asn Glu Thr Arg Arg Leu
            20                  25                  30

ACA ACA AGT GGA GCA TAC AAC ATT ATA GAC GGG TGC TGG AGG GGC AAA     144
Thr Thr Ser Gly Ala Tyr Asn Ile Ile Asp Gly Cys Trp Arg Gly Lys
        35                  40                  45

GCC GAT TGG GCG GAA AAC CGA AAA GCG TTA GCC GAT TGT GCC CAA GGT     192
Ala Asp Trp Ala Glu Asn Arg Lys Ala Leu Ala Asp Cys Ala Gln Gly
    50                  55                  60

TTT GGG AAG GGA ACA GTG GGC GGA AAA GAT GGT GAT ATA TAC ACG GTC     240
Phe Gly Lys Gly Thr Val Gly Gly Lys Asp Gly Asp Ile Tyr Thr Val
65                  70                  75                  80

ACC AGT GAG CTA GAT GAT GAT GTT GCA AAT CCA AAA GAA GGC ACA CTC     288
Thr Ser Glu Leu Asp Asp Asp Val Ala Asn Pro Lys Glu Gly Thr Leu
                85                  90                  95

CGG TTT GGT GCC GCC CAA AAC AGG CCC TTG TGG ATC ATT TTT GAA AGA     336
Arg Phe Gly Ala Ala Gln Asn Arg Pro Leu Trp Ile Ile Phe Glu Arg
            100                 105                 110

GAT ATG GTG ATT CGT TTG GAT AAA GAG ATG GTG GTA AAC AGT GAC AAG     384
Asp Met Val Ile Arg Leu Asp Lys Glu Met Val Val Asn Ser Asp Lys
        115                 120                 125

ACC ATC GAT GGC CGA GGG GCG AAA GTT GAA ATC ATT AAC GCT GGT TTC     432
Thr Ile Asp Gly Arg Gly Ala Lys Val Glu Ile Ile Asn Ala Gly Phe
    130                 135                 140

ACC CTT AAT GGT GTC AAG AAT GTA ATC ATT CAT AAC ATA AAT ATG CAT     480
Thr Leu Asn Gly Val Lys Asn Val Ile Ile His Asn Ile Asn Met His
145                 150                 155                 160

GAT GTT AAA GTG AAT CCA GGA GGC CTG ATT AAG TCC AAC GAT GGT CCA     528
Asp Val Lys Val Asn Pro Gly Gly Leu Ile Lys Ser Asn Asp Gly Pro
```

|     |     |     |     |     |     |     |     |     |     |     |     |     |     |     |     |     |
|-----|-----|-----|-----|-----|-----|-----|-----|-----|-----|-----|-----|-----|-----|-----|-----|-----|
|     |     |     |     | 165 |     |     |     |     | 170 |     |     |     |     | 175 |     |     |
| GCA | GCT | CCA | AGA | GCT | GGT | AGT | GAT | GGT | GAT | GCT | ATA | AGT | ATT | TCT | GGT | 576 |
| Ala | Ala | Pro | Arg | Ala | Gly | Ser | Asp | Gly | Asp | Ala | Ile | Ser | Ile | Ser | Gly |     |
|     |     |     | 180 |     |     |     |     | 185 |     |     |     |     | 190 |     |     |     |
| AGT | TCA | CAA | ATA | TGG | ATC | GAC | CAT | TGT | TCG | CTC | AGT | AAG | TCT | GTT | GAT | 624 |
| Ser | Ser | Gln | Ile | Trp | Ile | Asp | His | Cys | Ser | Leu | Ser | Lys | Ser | Val | Asp |     |
|     |     |     | 195 |     |     |     |     | 200 |     |     |     |     | 205 |     |     |     |
| GGG | CTG | GTA | GAT | GCC | AAG | CTC | GGC | ACC | ACA | CGC | TTA | ACC | GTT | TCC | AAC | 672 |
| Gly | Leu | Val | Asp | Ala | Lys | Leu | Gly | Thr | Thr | Arg | Leu | Thr | Val | Ser | Asn |     |
|     | 210 |     |     |     |     | 215 |     |     |     |     | 220 |     |     |     |     |     |
| AGC | TTA | TTC | ACC | CAA | CAC | CAG | TTT | GTA | CTA | TTA | TTC | GGG | GCT | GGT | GAC | 720 |
| Ser | Leu | Phe | Thr | Gln | His | Gln | Phe | Val | Leu | Leu | Phe | Gly | Ala | Gly | Asp |     |
| 225 |     |     |     |     | 230 |     |     |     |     | 235 |     |     |     |     | 240 |     |
| GAA | AAT | ATT | GAA | GAT | AGA | GGC | ATG | CTA | GCA | ACG | GTC | GCT | TTC | AAC | ACG | 768 |
| Glu | Asn | Ile | Glu | Asp | Arg | Gly | Met | Leu | Ala | Thr | Val | Ala | Phe | Asn | Thr |     |
|     |     |     |     | 245 |     |     |     |     | 250 |     |     |     |     | 255 |     |     |
| TTC | ACT | GAT | AAC | GTT | GAC | CAA | AGA | ATG | CCT | AGA | TGT | CGA | CAT | GGG | TTT | 816 |
| Phe | Thr | Asp | Asn | Val | Asp | Gln | Arg | Met | Pro | Arg | Cys | Arg | His | Gly | Phe |     |
|     |     |     | 260 |     |     |     |     | 265 |     |     |     |     | 270 |     |     |     |
| TTC | CAA | GTC | GTT | AAC | AAC | AAC | TAT | GAT | AAA | TGG | GGA | TCG | TAT | GCC | ATC | 864 |
| Phe | Gln | Val | Val | Asn | Asn | Asn | Tyr | Asp | Lys | Trp | Gly | Ser | Tyr | Ala | Ile |     |
|     |     |     | 275 |     |     |     |     | 280 |     |     |     |     | 285 |     |     |     |
| GGT | GGT | AGC | GCG | TCC | CCA | ACC | ATA | CTC | AGC | CAA | GGG | AAC | AGA | TTC | TGC | 912 |
| Gly | Gly | Ser | Ala | Ser | Pro | Thr | Ile | Leu | Ser | Gln | Gly | Asn | Arg | Phe | Cys |     |
|     | 290 |     |     |     |     | 295 |     |     |     |     | 300 |     |     |     |     |     |
| GCC | CCC | GAT | GAA | CGC | AGC | AAG | AAA | AAT | GTC | CTA | GGA | AGG | CAT | GGT | GAA | 960 |
| Ala | Pro | Asp | Glu | Arg | Ser | Lys | Lys | Asn | Val | Leu | Gly | Arg | His | Gly | Glu |     |
| 305 |     |     |     |     | 310 |     |     |     |     | 315 |     |     |     |     | 320 |     |
| GCC | GCC | GCA | GAG | TCG | ATG | AAG | TGG | AAC | TGG | AGA | ACG | AAT | AAA | GAC | GTG | 1008 |
| Ala | Ala | Ala | Glu | Ser | Met | Lys | Trp | Asn | Trp | Arg | Thr | Asn | Lys | Asp | Val |     |
|     |     |     |     | 325 |     |     |     |     | 330 |     |     |     |     | 335 |     |     |
| CTT | GAA | AAT | GGT | GCT | ATT | TTT | GTT | GCA | TCC | GGG | GTC | GAT | CCA | GTG | CTA | 1056 |
| Leu | Glu | Asn | Gly | Ala | Ile | Phe | Val | Ala | Ser | Gly | Val | Asp | Pro | Val | Leu |     |
|     |     |     | 340 |     |     |     |     | 345 |     |     |     |     | 350 |     |     |     |
| ACC | CCT | GAG | CAA | AGC | GCA | GGG | ATG | ATT | CCA | GCC | GAA | CCA | GGA | GAG | TCC | 1104 |
| Thr | Pro | Glu | Gln | Ser | Ala | Gly | Met | Ile | Pro | Ala | Glu | Pro | Gly | Glu | Ser |     |
|     |     | 355 |     |     |     |     | 360 |     |     |     |     | 365 |     |     |     |     |
| GCT | CTA | AGC | CTC | ACT | AGT | AGT | GCT | GGT | GTA | CTC | TCA | TGC | CAA | CCC | GGA | 1152 |
| Ala | Leu | Ser | Leu | Thr | Ser | Ser | Ala | Gly | Val | Leu | Ser | Cys | Gln | Pro | Gly |     |
|     | 370 |     |     |     |     | 375 |     |     |     |     | 380 |     |     |     |     |     |
| GCA | CCT | TGC | TAA | GCA | CCC | GAC | CAA | TTA | CTA | AGC | ACT | TAT | AAT |     |     | 1194 |
| Ala | Pro | Cys | *   |     |     |     |     |     |     |     |     |     |     |     |     |     |
| 385 |     |     |     |     |     |     |     |     |     |     |     |     |     |     |     |     |
| GA  |     |     |     |     |     |     |     |     |     |     |     |     |     |     |     | 1196 |

( 2 ) INFORMATION FOR SEQ ID NO:72:

( i ) SEQUENCE CHARACTERISTICS:
        ( A ) LENGTH: 387 amino acids
        ( B ) TYPE: amino acid
        ( D ) TOPOLOGY: linear ( i i ) MOLECULE TYPE: protein ( x i ) SEQUENCE DESCRIPTION: SEQ ID NO:72:

| Leu | Tyr | Phe | Thr | Leu | Ala | Leu | Val | Thr | Leu | Leu | Gln | Pro | Val | Arg | Ser |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Ala | Glu | Asp | Leu | Gln | Glu | Ile | Leu | Pro | Val | Asn | Glu | Thr | Arg | Arg | Leu |
|     |     |     | 20  |     |     |     |     | 25  |     |     |     |     | 30  |     |     |
| Thr | Thr | Ser | Gly | Ala | Tyr | Asn | Ile | Ile | Asp | Gly | Cys | Trp | Arg | Gly | Lys |
|     |     | 35  |     |     |     |     | 40  |     |     |     |     | 45  |     |     |     |

| Ala | Asp | Trp | Ala | Glu | Asn | Arg | Lys | Ala | Leu | Ala | Asp | Cys | Ala | Gln | Gly |
|---|---|---|---|---|---|---|---|---|---|---|---|---|---|---|---|
| | 50 | | | | 55 | | | | | 60 | | | | | |
| Phe | Gly | Lys | Gly | Thr | Val | Gly | Lys | Asp | Gly | Asp | Ile | Tyr | Thr | Val |
| 65 | | | | 70 | | | | 75 | | | | | 80 |
| Thr | Ser | Glu | Leu | Asp | Asp | Val | Ala | Asn | Pro | Lys | Glu | Gly | Thr | Leu |
| | | | | 85 | | | | 90 | | | | | 95 |
| Arg | Phe | Gly | Ala | Ala | Gln | Asn | Arg | Pro | Leu | Trp | Ile | Ile | Phe | Glu | Arg |
| | | | 100 | | | | | 105 | | | | | 110 | | |
| Asp | Met | Val | Ile | Arg | Leu | Asp | Lys | Glu | Met | Val | Val | Asn | Ser | Asp | Lys |
| | | 115 | | | | | 120 | | | | | 125 | | | |
| Thr | Ile | Asp | Gly | Arg | Gly | Ala | Lys | Val | Glu | Ile | Ile | Asn | Ala | Gly | Phe |
| | 130 | | | | | 135 | | | | | 140 | | | | |
| Thr | Leu | Asn | Gly | Val | Lys | Asn | Val | Ile | Ile | His | Asn | Ile | Asn | Met | His |
| 145 | | | | | 150 | | | | | 155 | | | | | 160 |
| Asp | Val | Lys | Val | Asn | Pro | Gly | Gly | Leu | Ile | Lys | Ser | Asn | Asp | Gly | Pro |
| | | | | 165 | | | | | 170 | | | | | 175 | |
| Ala | Ala | Pro | Arg | Ala | Gly | Ser | Asp | Gly | Asp | Ala | Ile | Ser | Ile | Ser | Gly |
| | | | 180 | | | | | 185 | | | | | 190 | | |
| Ser | Ser | Gln | Ile | Trp | Ile | Asp | His | Cys | Ser | Leu | Ser | Lys | Ser | Val | Asp |
| | | 195 | | | | | 200 | | | | | 205 | | | |
| Gly | Leu | Val | Asp | Ala | Lys | Leu | Gly | Thr | Thr | Arg | Leu | Thr | Val | Ser | Asn |
| | 210 | | | | | 215 | | | | | 220 | | | | |
| Ser | Leu | Phe | Thr | Gln | His | Gln | Phe | Val | Leu | Leu | Phe | Gly | Ala | Gly | Asp |
| 225 | | | | | 230 | | | | | 235 | | | | | 240 |
| Glu | Asn | Ile | Glu | Asp | Arg | Gly | Met | Leu | Ala | Thr | Val | Ala | Phe | Asn | Thr |
| | | | | 245 | | | | | 250 | | | | | 255 | |
| Phe | Thr | Asp | Asn | Val | Asp | Gln | Arg | Met | Pro | Arg | Cys | Arg | His | Gly | Phe |
| | | | 260 | | | | | 265 | | | | | 270 | | |
| Phe | Gln | Val | Val | Asn | Asn | Asn | Tyr | Asp | Lys | Trp | Gly | Ser | Tyr | Ala | Ile |
| | | 275 | | | | | 280 | | | | | 285 | | | |
| Gly | Gly | Ser | Ala | Ser | Pro | Thr | Ile | Leu | Ser | Gln | Gly | Asn | Arg | Phe | Cys |
| | 290 | | | | | 295 | | | | | 300 | | | | |
| Ala | Pro | Asp | Glu | Arg | Ser | Lys | Lys | Asn | Val | Leu | Gly | Arg | His | Gly | Glu |
| 305 | | | | | 310 | | | | | 315 | | | | | 320 |
| Ala | Ala | Ala | Glu | Ser | Met | Lys | Trp | Asn | Trp | Arg | Thr | Asn | Lys | Asp | Val |
| | | | | 325 | | | | | 330 | | | | | 335 | |
| Leu | Glu | Asn | Gly | Ala | Ile | Phe | Val | Ala | Ser | Gly | Val | Asp | Pro | Val | Leu |
| | | | 340 | | | | | 345 | | | | | 350 | | |
| Thr | Pro | Glu | Gln | Ser | Ala | Gly | Met | Ile | Pro | Ala | Glu | Pro | Gly | Glu | Ser |
| | | 355 | | | | | 360 | | | | | 365 | | | |
| Ala | Leu | Ser | Leu | Thr | Ser | Ser | Ala | Gly | Val | Leu | Ser | Cys | Gln | Pro | Gly |
| | 370 | | | | | 375 | | | | | 380 | | | | |
| Ala | Pro | Cys |
| 385 | | |

( 2 ) INFORMATION FOR SEQ ID NO:73:

( i ) SEQUENCE CHARACTERISTICS:
        ( A ) LENGTH: 1349 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS (B) LOCATION: 1..1323

(xi) SEQUENCE DESCRIPTION: SEQ ID NO:73:

| | | | | | | | | | | | | | | | | |
|---|---|---|---|---|---|---|---|---|---|---|---|---|---|---|---|---|
| ATG | GGG | ATC | AAA | CAC | TGT | TGT | TAC | ATC | TTG | TAT | TTT | ACC | TTA | GCC | CTT | 48 |
| Met 1 | Gly | Ile | Lys | His 5 | Cys | Cys | Tyr | Ile | Leu 10 | Tyr | Phe | Thr | Leu | Ala 15 | Leu | |
| GTC | ACT | TTG | CTG | CAA | CCT | GTT | CGT | TCT | GCA | GAA | GAT | GTT | GAA | GAA | TTC | 96 |
| Val | Thr | Leu | Leu 20 | Gln | Pro | Val | Arg | Ser 25 | Ala | Glu | Asp | Val 30 | Glu | Glu | Phe | |
| TTA | CCT | TCA | GCT | AAC | GAA | ACA | AGG | AGG | AGC | CTG | AAA | GCA | TGT | GAA | GCA | 144 |
| Leu | Pro | Ser 35 | Ala | Asn | Glu | Thr | Arg 40 | Arg | Ser | Leu | Lys | Ala 45 | Cys | Glu | Ala | |
| CAC | AAC | ATT | ATA | GAC | AAG | TGC | TGG | AGG | TGC | AAA | GCC | GAT | TGG | GCG | AAT | 192 |
| His | Asn | Ile 50 | Ile | Asp | Lys | Cys 55 | Trp | Arg | Cys | Lys | Ala 60 | Asp | Trp | Ala | Asn | |
| AAC | CGA | CAA | GCG | TTA | GCC | GAT | TGT | GCC | CAA | GGT | TTT | GCA | AAG | GGA | ACC | 240 |
| Asn 65 | Arg | Gln | Ala | Leu 70 | Ala | Asp | Cys | Ala | Gln 75 | Gly | Phe | Ala | Lys | Gly 80 | Thr | |
| TAC | GGT | GGA | AAA | CAT | GGT | GAT | GTC | TAC | ACG | GTC | ACC | AGT | GAT | AAA | GAT | 288 |
| Tyr | Gly | Gly | Lys | His 85 | Gly | Asp | Val | Tyr | Thr 90 | Val | Thr | Ser | Asp | Lys 95 | Asp | |
| GAT | GAT | GTT | GCA | AAT | CCA | AAA | GAA | GGC | ACA | CTC | CGG | TTT | GCT | GCT | GCC | 336 |
| Asp | Asp | Val | Ala 100 | Asn | Pro | Lys | Glu | Gly 105 | Thr | Leu | Arg | Phe | Ala 110 | Ala | Ala | |
| CAA | AAC | AGG | CCC | TTG | TGG | ATC | ATT | TTT | AAA | AGA | AAT | ATG | GTG | ATT | CAT | 384 |
| Gln | Asn | Arg 115 | Pro | Leu | Trp | Ile | Ile 120 | Phe | Lys | Arg | Asn | Met 125 | Val | Ile | His | |
| TTG | AAT | CAA | GAG | CTT | GTC | GTA | AAC | AGC | GAC | AAG | ACC | ATC | GAT | GGC | CGA | 432 |
| Leu | Asn 130 | Gln | Glu | Leu | Val | Val 135 | Asn | Ser | Asp | Lys | Thr 140 | Ile | Asp | Gly | Arg | |
| GGG | GTG | AAA | GTT | AAC | ATC | GTT | AAC | GCC | GGT | CTC | ACC | CTC | ATG | AAT | GTC | 480 |
| Gly 145 | Val | Lys | Val | Asn | Ile 150 | Val | Asn | Ala | Gly | Leu 155 | Thr | Leu | Met | Asn | Val 160 | |
| AAG | AAT | ATA | ATC | ATT | CAT | AAC | ATA | AAT | ATC | CAT | GAT | ATT | AAA | GTT | TGT | 528 |
| Lys | Asn | Ile | Ile | Ile 165 | His | Asn | Ile | Asn | Ile 170 | His | Asp | Ile | Lys | Val 175 | Cys | |
| CCA | GGA | GGC | ATG | ATT | AAG | TCC | AAC | GAT | GGT | CCA | CCA | ATT | TTA | AGA | CAA | 576 |
| Pro | Gly | Gly | Met 180 | Ile | Lys | Ser | Asn | Asp 185 | Gly | Pro | Pro | Ile | Leu 190 | Arg | Gln | |
| CAA | AGT | GAT | GGT | GAT | GCT | ATA | AAT | GTT | GCT | GGT | AGT | TCA | CAA | ATA | TGG | 624 |
| Gln | Ser | Asp 195 | Gly | Asp | Ala | Ile | Asn 200 | Val | Ala | Gly | Ser | Ser 205 | Gln | Ile | Trp | |
| ATC | GAC | CAT | TGC | TCG | CTC | AGT | AAG | GCT | TCC | GAT | GGG | CTG | CTC | GAT | ATC | 672 |
| Ile | Asp | His 210 | Cys | Ser | Leu | Ser | Lys 215 | Ala | Ser | Asp | Gly | Leu 220 | Leu | Asp | Ile | |
| ACC | CTC | GGC | AGC | TCA | CAC | GTG | ACC | GTT | TCC | AAC | TGC | AAA | TTC | ACC | CAA | 720 |
| Thr 225 | Leu | Gly | Ser | Ser | His 230 | Val | Thr | Val | Ser | Asn 235 | Cys | Lys | Phe | Thr | Gln 240 | |
| CAC | CAA | TTT | GTA | TTA | TTG | CTC | GGG | GCT | GAT | GAC | ACC | CAT | TAT | CAA | GAT | 768 |
| His | Gln | Phe | Val | Leu 245 | Leu | Leu | Gly | Ala | Asp 250 | Asp | Thr | His | Tyr | Gln 255 | Asp | |
| AAA | GGC | ATG | CTA | GCA | ACG | GTA | GCA | TTC | AAC | ATG | TTC | ACC | GAT | CAC | GTT | 816 |
| Lys | Gly | Met | Leu 260 | Ala | Thr | Val | Ala | Phe 265 | Asn | Met | Phe | Thr | Asp 270 | His | Val | |
| GAC | CAA | AGA | ATG | CCT | AGA | TGT | AGA | TTT | GGG | TTT | TTC | CAA | GTC | GTT | AAC | 864 |
| Asp | Gln | Arg | Met 275 | Pro | Arg | Cys | Arg | Phe 280 | Gly | Phe | Phe | Gln | Val 285 | Val | Asn | |
| AAC | AAC | TAC | GAC | AGA | TGG | GGA | ACG | TAC | GCC | ATC | GGT | GGT | AGC | TCG | GCC | 912 |
| Asn | Asn | Tyr | Asp 290 | Arg | Trp | Gly | Thr | Tyr 295 | Ala | Ile | Gly | Gly | Ser 300 | Ser | Ala | |

| | | | | | | | | | | | | | | | | |
|---|---|---|---|---|---|---|---|---|---|---|---|---|---|---|---|---|
| CCA | ACT | ATA | CTC | AGC | CAA | GGG | AAC | AGA | TTC | TTC | GCC | CCC | GAT | GAT | ATC | 960 |
| Pro | Thr | Ile | Leu | Ser | Gln | Gly | Asn | Arg | Phe | Phe | Ala | Pro | Asp | Asp | Ile | |
| 305 | | | | 310 | | | | | 315 | | | | | | 320 | |
| ATC | AAG | AAA | AAT | GTC | TTA | GCG | AGG | ACT | GGT | ACT | GGC | AAC | GCA | GAG | TCG | 1008 |
| Ile | Lys | Lys | Asn | Val | Leu | Ala | Arg | Thr | Gly | Thr | Gly | Asn | Ala | Glu | Ser | |
| | | | | 325 | | | | | 330 | | | | | 335 | | |
| ATG | TCG | TGG | AAC | TGG | AGA | ACA | GAT | AGA | GAC | TTG | CTT | GAA | AAT | GGT | GCT | 1056 |
| Met | Ser | Trp | Asn | Trp | Arg | Thr | Asp | Arg | Asp | Leu | Leu | Glu | Asn | Gly | Ala | |
| | | | 340 | | | | | 345 | | | | | | | 350 | |
| ATT | TTT | CTC | CCA | TCC | GGG | TCT | GAT | CCA | GTG | CTA | ACC | CCT | GAG | CAA | AAA | 1104 |
| Ile | Phe | Leu | Pro | Ser | Gly | Ser | Asp | Pro | Val | Leu | Thr | Pro | Glu | Gln | Lys | |
| | | 355 | | | | | 360 | | | | | 365 | | | | |
| GCA | GGG | ATG | ATT | CCA | GCT | GAA | CCA | GGA | GAA | GCC | GTT | CTA | AGA | CTC | ACT | 1152 |
| Ala | Gly | Met | Ile | Pro | Ala | Glu | Pro | Gly | Glu | Ala | Val | Leu | Arg | Leu | Thr | |
| | | 370 | | | | 375 | | | | | 380 | | | | | |
| AGT | AGT | GCT | GGT | GTA | CTC | TCA | TGC | CAT | CAA | GGA | GCA | CCT | TGC | TAA | GCA | 1200 |
| Ser | Ser | Ala | Gly | Val | Leu | Ser | Cys | His | Gln | Gly | Ala | Pro | Cys | * | Ala | |
| 385 | | | | | 390 | | | | 395 | | | | | | 400 | |
| CCT | GGC | CAA | TTC | CTA | AGC | TTT | TAT | AAT | AAT | CAT | AAA | TAC | TTA | TTT | TAT | 1248 |
| Pro | Gly | Gln | Phe | Leu | Ser | Phe | Tyr | Asn | Asn | His | Lys | Tyr | Leu | Phe | Tyr | |
| | | | | 405 | | | | | 410 | | | | | 415 | | |
| TTT | ATT | TTT | GAT | ATT | TTA | TAT | GAA | CCA | TTA | CGT | TCA | AGT | ACT | CTA | TTA | 1296 |
| Phe | Ile | Phe | Asp | Ile | Leu | Tyr | Glu | Pro | Leu | Arg | Ser | Ser | Thr | Leu | Leu | |
| | | | 420 | | | | | 425 | | | | | 430 | | | |
| ACA | TGT | TTT | AAA | TTC | ATA | AGA | GTT | TAT | TGA | TAA | AAA | AAA | AAA | AAA | CCG | 1344 |
| Thr | Cys | Phe | Lys | Phe | Ile | Arg | Val | Tyr | * | * | | | | | | |
| | | 435 | | | | | 440 | | | | | | | | | |
| AAT | TC | | | | | | | | | | | | | | | 1349 |

( 2 ) INFORMATION FOR SEQ ID NO:74:

( i ) SEQUENCE CHARACTERISTICS:
        ( A ) LENGTH: 398 amino acids
        ( B ) TYPE: amino acid
        ( D ) TOPOLOGY: linear ( i i ) MOLECULE TYPE: protein ( x i ) SEQUENCE DESCRIPTION: SEQ ID NO:74:

| | | | | | | | | | | | | | | |
|---|---|---|---|---|---|---|---|---|---|---|---|---|---|---|
| Met | Gly | Ile | Lys | His | Cys | Cys | Tyr | Ile | Leu | Tyr | Phe | Thr | Leu | Ala | Leu |
| 1 | | | | 5 | | | | | 10 | | | | | 15 | |
| Val | Thr | Leu | Leu | Gln | Pro | Val | Arg | Ser | Ala | Glu | Asp | Val | Glu | Glu | Phe |
| | | | 20 | | | | | 25 | | | | | 30 | | |
| Leu | Pro | Ser | Ala | Asn | Glu | Thr | Arg | Arg | Ser | Leu | Lys | Ala | Cys | Glu | Ala |
| | | | 35 | | | | | 40 | | | | | 45 | | |
| His | Asn | Ile | Ile | Asp | Lys | Cys | Trp | Arg | Cys | Lys | Ala | Asp | Trp | Ala | Asn |
| | 50 | | | | | 55 | | | | | 60 | | | | |
| Asn | Arg | Gln | Ala | Leu | Ala | Asp | Cys | Ala | Gln | Gly | Phe | Ala | Lys | Gly | Thr |
| 65 | | | | | 70 | | | | | 75 | | | | | 80 |
| Tyr | Gly | Gly | Lys | His | Gly | Asp | Val | Tyr | Thr | Val | Thr | Ser | Asp | Lys | Asp |
| | | | | 85 | | | | | 90 | | | | | 95 | |
| Asp | Asp | Val | Ala | Asn | Pro | Lys | Glu | Gly | Thr | Leu | Arg | Phe | Ala | Ala | Ala |
| | | | 100 | | | | | 105 | | | | | 110 | | |
| Gln | Asn | Arg | Pro | Leu | Trp | Ile | Ile | Phe | Lys | Arg | Asn | Met | Val | Ile | His |
| | | 115 | | | | | 120 | | | | | 125 | | | |
| Leu | Asn | Gln | Glu | Leu | Val | Val | Asn | Ser | Asp | Lys | Thr | Ile | Asp | Gly | Arg |
| | 130 | | | | | 135 | | | | | 140 | | | | |
| Gly | Val | Lys | Val | Asn | Ile | Val | Asn | Ala | Gly | Leu | Thr | Leu | Met | Asn | Val |
| 145 | | | | | 150 | | | | | 155 | | | | | 160 |

| | | | | | | | | | | | | | | |
|---|---|---|---|---|---|---|---|---|---|---|---|---|---|---|
|Lys|Asn|Ile|Ile|Ile 165|His|Asn|Ile|Asn 170|Ile|His|Asp|Ile|Lys 175|Val|Cys|
|Pro|Gly|Gly|Met 180|Ile|Lys|Ser|Asn|Asp 185|Gly|Pro|Pro|Ile|Leu 190|Arg|Gln|
|Gln|Ser|Asp 195|Gly|Asp|Ala|Ile|Asn 200|Val|Ala|Gly|Ser|Ser 205|Gln|Ile|Trp|
|Ile|Asp 210|His|Cys|Ser|Leu|Ser 215|Lys|Ala|Ser|Asp|Gly 220|Leu|Leu|Asp|Ile|
|Thr 225|Leu|Gly|Ser|Ser|His 230|Val|Thr|Val|Ser|Asn 235|Cys|Lys|Phe|Thr|Gln 240|
|His|Gln|Phe|Val|Leu 245|Leu|Leu|Gly|Ala|Asp 250|Asp|Thr|His|Tyr|Gln 255|Asp|
|Lys|Gly|Met|Leu 260|Ala|Thr|Val|Ala|Phe 265|Asn|Met|Phe|Thr|Asp 270|His|Val|
|Asp|Gln|Arg 275|Met|Pro|Arg|Cys|Arg 280|Phe|Gly|Phe|Phe|Gln 285|Val|Val|Asn|
|Asn|Asn 290|Tyr|Asp|Arg|Trp|Gly 295|Thr|Tyr|Ala|Ile|Gly 300|Gly|Ser|Ser|Ala|
|Pro 305|Thr|Ile|Leu|Ser|Gln 310|Gly|Asn|Arg|Phe|Phe 315|Ala|Pro|Asp|Asp|Ile 320|
|Ile|Lys|Lys|Asn|Val 325|Leu|Ala|Arg|Thr|Gly 330|Thr|Gly|Asn|Ala|Glu 335|Ser|
|Met|Ser|Trp|Asn 340|Trp|Arg|Thr|Asp|Arg 345|Asp|Leu|Leu|Glu|Asn 350|Gly|Ala|
|Ile|Phe|Leu 355|Pro|Ser|Gly|Ser|Asp 360|Pro|Val|Leu|Thr|Pro 365|Glu|Gln|Lys|
|Ala|Gly 370|Met|Ile|Pro|Ala|Glu 375|Pro|Gly|Glu|Ala|Val 380|Leu|Arg|Leu|Thr|
|Ser 385|Ser|Ala|Gly|Val|Leu 390|Ser|Cys|His|Gln|Gly 395|Ala|Pro|Cys| | |

(2) INFORMATION FOR SEQ ID NO:75:

(i) SEQUENCE CHARACTERISTICS:
        (A) LENGTH: 1320 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1302

(xi) SEQUENCE DESCRIPTION: SEQ ID NO:75:

| | | | | | | | | | | | | | | | | |
|---|---|---|---|---|---|---|---|---|---|---|---|---|---|---|---|---|
|ATG|GGG|ATC|AAA|CAA|TGT|TGT|TAC|ATC|TTG|TAT|TTT|ACC|TTA|GCA|CTT|48|
|Met 1|Gly|Ile|Lys|Gln 5|Cys|Cys|Tyr|Ile|Leu 10|Tyr|Phe|Thr|Leu|Ala 15|Leu| |
|GTC|GCT|TTG|CTG|CAA|CCT|GTT|CGT|TCT|GCC|GAA|GGT|GTC|GGG|GAA|ATC|96|
|Val|Ala|Leu|Leu 20|Gln|Pro|Val|Arg|Ser 25|Ala|Glu|Gly|Val|Gly 30|Glu|Ile| |
|TTA|CCT|TCA|GTT|AAC|GAA|ACG|AGG|AGC|CTG|CAA|GCA|TGT|GAA|GCA|CTC|144|
|Leu|Pro|Ser 35|Val|Asn|Glu|Thr|Arg 40|Ser|Leu|Gln|Ala|Cys 45|Glu|Ala|Leu| |
|AAC|ATT|ATA|GAC|AAG|TGC|TGG|AGG|GGC|AAA|GCC|GAT|TGG|GAG|AAC|AAC|192|
|Asn|Ile|Ile 50|Asp|Lys|Cys|Trp|Arg 55|Gly|Lys|Ala|Asp|Trp 60|Glu|Asn|Asn| |
|CGA|CAA|GCG|TTA|GCC|GAC|TGT|GCC|CAA|GGT|TTT|GCA|AAG|GGA|ACC|TAC|240|
|Arg|Gln|Ala|Leu|Ala|Asp|Cys|Ala|Gln|Gly|Phe|Ala|Lys|Gly|Thr|Tyr| |

|  |  |  |  |  |  |  |  |  |  |  |  |  |  |  |  |  |
|---|---|---|---|---|---|---|---|---|---|---|---|---|---|---|---|---|
| 65 | | | | | 70 | | | | | 75 | | | | | 80 | |

```
GGC GGA AAA TGG GGT GAT GTC TAC ACG GTC ACC AGC AAT CTA GAT GAT      288
Gly Gly Lys Trp Gly Asp Val Tyr Thr Val Thr Ser Asn Leu Asp Asp
              85                      90                      95

GAT GTT GCA AAT CCA AAA GAA GGC ACA CTC CGG TTT GCT GCC GCC CAA      336
Asp Val Ala Asn Pro Lys Glu Gly Thr Leu Arg Phe Ala Ala Ala Gln
                100                     105                     110

AAC AGG CCC TTG TGG ATC ATT TTT AAA AAT GAT ATG GTG ATT AAT TTG      384
Asn Arg Pro Leu Trp Ile Ile Phe Lys Asn Asp Met Val Ile Asn Leu
        115                     120                     125

AAT CAA GAG CTT GTC GTA AAC AGC GAC AAG ACC ATC GAT GGC CGA GGG      432
Asn Gln Glu Leu Val Val Asn Ser Asp Lys Thr Ile Asp Gly Arg Gly
    130                     135                     140

GTG AAA GTT GAA ATC ATT AAC GGA GGT CTC ACC CTC ATG AAT GTC AAG      480
Val Lys Val Glu Ile Ile Asn Gly Gly Leu Thr Leu Met Asn Val Lys
145                     150                     155                 160

AAT ATA ATC ATT CAT AAC ATA AAT ATC CAT GAT GTT AAA GTG CTT CCA      528
Asn Ile Ile Ile His Asn Ile Asn Ile His Asp Val Lys Val Leu Pro
        165                     170                     175

GGA GGC ATG ATT AAG TCC AAC GAT GGT CCA CCA ATT TTA AGA CAA GCA      576
Gly Gly Met Ile Lys Ser Asn Asp Gly Pro Pro Ile Leu Arg Gln Ala
            180                     185                     190

AGT GAT GGG GAT ACT ATA AAT GTT GCT GGT AGT TCC CAA ATA TGG ATA      624
Ser Asp Gly Asp Thr Ile Asn Val Ala Gly Ser Ser Gln Ile Trp Ile
        195                     200                     205

GAC CAT TGC TCA CTC AGC AAG TCT TTC GAT GGG CTG GTC GAT GTC ACC      672
Asp His Cys Ser Leu Ser Lys Ser Phe Asp Gly Leu Val Asp Val Thr
    210                     215                     220

CTC GGT AGC ACA CAC GTG ACC ATT TCC AAC TGC AAA TTC ACC CAA CAG      720
Leu Gly Ser Thr His Val Thr Ile Ser Asn Cys Lys Phe Thr Gln Gln
225                     230                     235                 240

TCA AAA GCA ATA TTG TTG GGA GCA GAT GAC ACC CAT GTT CAA GAT AAA      768
Ser Lys Ala Ile Leu Leu Gly Ala Asp Asp Thr His Val Gln Asp Lys
        245                     250                     255

GGA ATG CTA GCA ACG GTC GCT TTC AAC ATG TTC ACC GAT AAC GTT GAC      816
Gly Met Leu Ala Thr Val Ala Phe Asn Met Phe Thr Asp Asn Val Asp
            260                     265                     270

CAA AGA ATG CCT AGA TGT CGA TTT GGG TTT TTC CAA GTT GTT AAC AAC      864
Gln Arg Met Pro Arg Cys Arg Phe Gly Phe Phe Gln Val Val Asn Asn
        275                     280                     285

AAC TAC GAC AGA TGG GGA ACG TAC GCC ATA GGT GGT AGC TCG GCC CCA      912
Asn Tyr Asp Arg Trp Gly Thr Tyr Ala Ile Gly Gly Ser Ser Ala Pro
    290                     295                     300

ACT ATA CTC TGC CAA GGG AAC AGA TTC TTG GCC CCT GAT GAT CAG ATC      960
Thr Ile Leu Cys Gln Gly Asn Arg Phe Leu Ala Pro Asp Asp Gln Ile
305                     310                     315                 320

AAG AAA AAT GTC CTA GCG AGG ACT GGT ACA GGC GCT GCT GAG TCG ATG     1008
Lys Lys Asn Val Leu Ala Arg Thr Gly Thr Gly Ala Ala Glu Ser Met
        325                     330                     335

GCG TGG AAC TGG AGA TCT GAT AAA GAC TTG CTT GAA AAT GGT GCT ATT     1056
Ala Trp Asn Trp Arg Ser Asp Lys Asp Leu Leu Glu Asn Gly Ala Ile
            340                     345                     350

TTT GTT ACA TCT GGG TCT GAT CCA GTG CTA ACC CCT GTT CAA AGC GCA     1104
Phe Val Thr Ser Gly Ser Asp Pro Val Leu Thr Pro Val Gln Ser Ala
        355                     360                     365

GGG ATG ATT CCA GCT GAA CCA GGA GAA GCC GCT ATA AAA CTC ACT AGT     1152
Gly Met Ile Pro Ala Glu Pro Gly Glu Ala Ala Ile Lys Leu Thr Ser
370                     375                     380

AGT GCT GGT GTA TTC TCA TGC CGT CCT GGA GCA CCT TGC TAA GCA CCC     1200
Ser Ala Gly Val Phe Ser Cys Arg Pro Gly Ala Pro Cys  *  Ala Pro
```

```
385                    390                         395                         400
TGC CAA TTC TCC TAA GCT TTT GCA ATG ATC AAA AAT ACT TTT TTA TTT          1248
Cys Gln Phe Ser  *  Ala Phe Ala Met Ile Lys Asn Thr Phe Leu Phe
                405                     410                 415

TAT TTT TAA TAT TTT ATA TGT ACT GGA AAT GAA CCA TTA CCT TCT AGT          1296
Tyr Phe  *  Tyr Phe Ile Cys Thr Gly Asn Glu Pro Leu Pro Ser Ser
            420                     425                 430

ACT CTA TAA CAT GTT TTG CAT TTA                                          1320
Thr Leu  *
         435
```

( 2 ) INFORMATION FOR SEQ ID NO:76:

( i ) SEQUENCE CHARACTERISTICS:
        ( A ) LENGTH: 397 amino acids
        ( B ) TYPE: amino acid
        ( D ) TOPOLOGY: linear ( i i ) MOLECULE TYPE: protein ( x i ) SEQUENCE DESCRIPTION: SEQ ID NO:76:

```
Met Gly Ile Lys Gln Cys Cys Tyr Ile Leu Tyr Phe Thr Leu Ala Leu
 1               5                  10                  15

Val Ala Leu Leu Gln Pro Val Arg Ser Ala Glu Gly Val Gly Glu Ile
                20                  25                  30

Leu Pro Ser Val Asn Glu Thr Arg Ser Leu Gln Ala Cys Glu Ala Leu
            35                  40                  45

Asn Ile Ile Asp Lys Cys Trp Arg Gly Lys Ala Asp Trp Glu Asn Asn
        50                  55                  60

Arg Gln Ala Leu Ala Asp Cys Ala Gln Gly Phe Ala Lys Gly Thr Tyr
 65                 70                  75                  80

Gly Gly Lys Trp Gly Asp Val Tyr Thr Val Thr Ser Asn Leu Asp Asp
                85                  90                  95

Asp Val Ala Asn Pro Lys Glu Gly Thr Leu Arg Phe Ala Ala Ala Gln
            100                 105                 110

Asn Arg Pro Leu Trp Ile Ile Phe Lys Asn Asp Met Val Ile Asn Leu
        115                 120                 125

Asn Gln Glu Leu Val Val Asn Ser Asp Lys Thr Ile Asp Gly Arg Gly
    130                 135                 140

Val Lys Val Glu Ile Ile Asn Gly Gly Leu Thr Leu Met Asn Val Lys
145                 150                 155                 160

Asn Ile Ile Ile His Asn Ile Asn Ile His Asp Val Lys Val Leu Pro
                165                 170                 175

Gly Gly Met Ile Lys Ser Asn Asp Gly Pro Pro Ile Leu Arg Gln Ala
            180                 185                 190

Ser Asp Gly Asp Thr Ile Asn Val Ala Gly Ser Ser Gln Ile Trp Ile
        195                 200                 205

Asp His Cys Ser Leu Ser Lys Ser Phe Asp Gly Leu Val Asp Val Thr
    210                 215                 220

Leu Gly Ser Thr His Val Thr Ile Ser Asn Cys Lys Phe Thr Gln Gln
225                 230                 235                 240

Ser Lys Ala Ile Leu Leu Gly Ala Asp Asp Thr His Val Gln Asp Lys
                245                 250                 255

Gly Met Leu Ala Thr Val Ala Phe Asn Met Phe Thr Asp Asn Val Asp
            260                 265                 270

Gln Arg Met Pro Arg Cys Arg Phe Gly Phe Phe Gln Val Val Asn Asn
        275                 280                 285
```

```
Asn  Tyr  Asp  Arg  Trp  Gly  Thr  Tyr  Ala  Ile  Gly  Gly  Ser  Ser  Ala  Pro
     290                      295                 300

Thr  Ile  Leu  Cys  Gln  Gly  Asn  Arg  Phe  Leu  Ala  Pro  Asp  Asp  Gln  Ile
305                           310                 315                      320

Lys  Lys  Asn  Val  Leu  Ala  Arg  Thr  Gly  Thr  Gly  Ala  Ala  Glu  Ser  Met
                    325                      330                     335

Ala  Trp  Asn  Trp  Arg  Ser  Asp  Lys  Asp  Leu  Leu  Glu  Asn  Gly  Ala  Ile
                    340                 345                                350

Phe  Val  Thr  Ser  Gly  Ser  Asp  Pro  Val  Leu  Thr  Pro  Val  Gln  Ser  Ala
               355                 360                 365

Gly  Met  Ile  Pro  Ala  Glu  Pro  Gly  Glu  Ala  Ala  Ile  Lys  Leu  Thr  Ser
     370                      375                 380

Ser  Ala  Gly  Val  Phe  Ser  Cys  Arg  Pro  Gly  Ala  Pro  Cys
385                      390                 395
```

( 2 ) INFORMATION FOR SEQ ID NO:77:

( i ) SEQUENCE CHARACTERISTICS:
        ( A ) LENGTH: 1160 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..1148

( x i ) SEQUENCE DESCRIPTION: SEQ ID NO:77:

```
TTG  TAT  TTT  ACC  TTA  GCC  CTT  GTC  ACT  TTG  CTG  CAA  CCT  GTT  CGT  TCT       48
Leu  Tyr  Phe  Thr  Leu  Ala  Leu  Val  Thr  Leu  Leu  Gln  Pro  Val  Arg  Ser
  1                 5                      10                      15

GCC  GAA  GAT  CTC  CAG  GAA  ATC  TTA  CCT  TCA  GCT  AAC  GAA  ACA  AGG  AGC       96
Ala  Glu  Asp  Leu  Gln  Glu  Ile  Leu  Pro  Ser  Ala  Asn  Glu  Thr  Arg  Ser
                20                      25                      30

CTG  ACA  ACA  TGT  GGA  ACA  TAC  AAC  ATT  ATA  GAC  GGG  TGC  TGG  AGG  GGC      144
Leu  Thr  Thr  Cys  Gly  Thr  Tyr  Asn  Ile  Ile  Asp  Gly  Cys  Trp  Arg  Gly
          35                      40                      45

AAA  GCC  GAT  TGG  GCG  GAA  AAC  CGA  AAA  GCG  TTA  GCC  GAT  TGT  GCC  CAA      192
Lys  Ala  Asp  Trp  Ala  Glu  Asn  Arg  Lys  Ala  Leu  Ala  Asp  Cys  Ala  Gln
     50                      55                      60

GGT  TTT  GCA  AAG  GGA  ACA  ATC  GGC  GGA  AAA  GAT  GGT  GAT  ATA  TAC  ACG      240
Gly  Phe  Ala  Lys  Gly  Thr  Ile  Gly  Gly  Lys  Asp  Gly  Asp  Ile  Tyr  Thr
 65                      70                      75                       80

GTC  ACC  AGT  GAG  CTA  GAT  GAT  GAT  GTT  GCA  AAT  CCA  AAA  GAA  GGC  ACA      288
Val  Thr  Ser  Glu  Leu  Asp  Asp  Asp  Val  Ala  Asn  Pro  Lys  Glu  Gly  Thr
                    85                      90                      95

CTC  CGG  TTT  GGT  GCC  GCC  CAA  AAC  AGG  CCC  TTG  TGG  ATT  ATT  TTT  GAA      336
Leu  Arg  Phe  Gly  Ala  Ala  Gln  Asn  Arg  Pro  Leu  Trp  Ile  Ile  Phe  Glu
               100                     105                     110

AGA  GAT  ATG  GTG  ATT  CGT  TTG  GAT  AGA  GAG  TTG  GCT  ATA  AAC  AAC  GAC      384
Arg  Asp  Met  Val  Ile  Arg  Leu  Asp  Arg  Glu  Leu  Ala  Ile  Asn  Asn  Asp
          115                     120                     125

AAG  ACC  ATC  GAT  GGC  CGA  GGG  GCG  AAA  GTT  GAA  ATC  ATT  AAC  GCT  GGT      432
Lys  Thr  Ile  Asp  Gly  Arg  Gly  Ala  Lys  Val  Glu  Ile  Ile  Asn  Ala  Gly
     130                     135                     140

TTC  GCC  ATC  TAT  AAT  GTC  AAG  AAT  ATA  ATC  ATT  CAT  AAC  ATA  ATT  ATG      480
Phe  Ala  Ile  Tyr  Asn  Val  Lys  Asn  Ile  Ile  Ile  His  Asn  Ile  Ile  Met
145                     150                     155                      160

CAT  GAT  ATT  GTA  GTG  AAT  CCA  GGA  GGC  CTG  ATT  AAG  TCC  CAC  GAT  GGT      528
His  Asp  Ile  Val  Val  Asn  Pro  Gly  Gly  Leu  Ile  Lys  Ser  His  Asp  Gly
```

|     |     |     | 165 |     |     |     |     | 170 |     |     |     |     | 175 |     |      |
| --- | --- | --- | --- | --- | --- | --- | --- | --- | --- | --- | --- | --- | --- | --- | ---- |
| CCA | CCA | GTT | CCA | AGA | AAG | GGT | AGT | GAT | GGT | GAT | GCT | ATA | GGT | ATT | TCT  | 576
| Pro | Pro | Val | Pro | Arg | Lys | Gly | Ser | Asp | Gly | Asp | Ala | Ile | Gly | Ile | Ser  |
|     |     |     | 180 |     |     |     |     | 185 |     |     |     |     | 190 |     |      |

| GGT | GGT | TCA | CAA | ATA | TGG | ATC | GAC | CAT | TGC | TCC | CTC | AGT | AAG | GCT | GTT | 624
| Gly | Gly | Ser | Gln | Ile | Trp | Ile | Asp | His | Cys | Ser | Leu | Ser | Lys | Ala | Val |
|     |     | 195 |     |     |     |     | 200 |     |     |     |     | 205 |     |     |     |

| GAT | GGG | CTA | ATC | GAT | GCT | AAA | CAC | GGC | AGC | ACA | CAC | TTC | ACC | GTT | TCT | 672
| Asp | Gly | Leu | Ile | Asp | Ala | Lys | His | Gly | Ser | Thr | His | Phe | Thr | Val | Ser |
|     | 210 |     |     |     |     | 215 |     |     |     |     | 220 |     |     |     |     |

| AAC | TGC | TTA | TTC | ACC | CAA | CAC | CAA | TAT | TTA | TTA | TTG | TTC | TGG | GAT | TTT | 720
| Asn | Cys | Leu | Phe | Thr | Gln | His | Gln | Tyr | Leu | Leu | Leu | Phe | Trp | Asp | Phe |
| 225 |     |     |     |     | 230 |     |     |     |     | 235 |     |     |     |     | 240 |

| GAC | GAG | CGA | GGC | ATG | CTA | TGT | ACG | GTC | GCA | TTC | AAC | AAG | TTC | ACT | GAT | 768
| Asp | Glu | Arg | Gly | Met | Leu | Cys | Thr | Val | Ala | Phe | Asn | Lys | Phe | Thr | Asp |
|     |     |     |     | 245 |     |     |     |     | 250 |     |     |     |     | 255 |     |

| AAC | GTT | GAC | CAA | AGA | ATG | CCT | AAC | TTA | CGA | CAT | GGG | TTT | GTC | CAA | GTC | 816
| Asn | Val | Asp | Gln | Arg | Met | Pro | Asn | Leu | Arg | His | Gly | Phe | Val | Gln | Val |
|     |     |     | 260 |     |     |     |     | 265 |     |     |     |     | 270 |     |     |

| GTT | AAC | AAC | AAC | TAC | GAA | AGA | TGG | GGA | TCG | TAC | GCC | CTC | GGT | GGT | AGC | 864
| Val | Asn | Asn | Asn | Tyr | Glu | Arg | Trp | Gly | Ser | Tyr | Ala | Leu | Gly | Gly | Ser |
|     |     | 275 |     |     |     |     | 280 |     |     |     |     | 285 |     |     |     |

| GCA | GGC | CCA | ACC | ATA | CTT | AGC | CAA | GGG | AAC | AGA | TTC | TTA | GCC | TCC | GAT | 912
| Ala | Gly | Pro | Thr | Ile | Leu | Ser | Gln | Gly | Asn | Arg | Phe | Leu | Ala | Ser | Asp |
| 290 |     |     |     |     |     | 295 |     |     |     |     | 300 |     |     |     |     |

| ATC | AAG | AAA | GAG | GTC | GTA | GGG | AGG | TAT | GGT | GAA | TCC | GCC | ATG | TCA | GAG | 960
| Ile | Lys | Lys | Glu | Val | Val | Gly | Arg | Tyr | Gly | Glu | Ser | Ala | Met | Ser | Glu |
| 305 |     |     |     |     | 310 |     |     |     |     | 315 |     |     |     |     | 320 |

| TCG | ATT | AAT | TGG | AAC | TGG | AGA | TCG | TAT | ATG | GAC | GTA | TTT | GAA | AAT | GGT | 1008
| Ser | Ile | Asn | Trp | Asn | Trp | Arg | Ser | Tyr | Met | Asp | Val | Phe | Glu | Asn | Gly |
|     |     |     |     | 325 |     |     |     |     | 330 |     |     |     |     | 335 |     |

| GCT | ATT | TTT | GTT | CCA | TCC | GGG | GTT | GAT | CCA | GTG | CTA | ACC | CCT | GAG | CAA | 1056
| Ala | Ile | Phe | Val | Pro | Ser | Gly | Val | Asp | Pro | Val | Leu | Thr | Pro | Glu | Gln |
|     |     |     | 340 |     |     |     |     | 345 |     |     |     |     | 350 |     |     |

| AAC | GCA | GGG | ATG | ATT | CCA | GCC | GAA | CCA | GGA | GAA | GCC | GTT | CTA | AGA | CTC | 1104
| Asn | Ala | Gly | Met | Ile | Pro | Ala | Glu | Pro | Gly | Glu | Ala | Val | Leu | Arg | Leu |
|     |     | 355 |     |     |     |     | 360 |     |     |     |     | 365 |     |     |     |

| ACT | AGT | AGT | GCT | GGT | GTC | CTC | TCA | TGC | CAA | CCT | GGA | GCA | CCT | TGC | TAA | 1152
| Thr | Ser | Ser | Ala | Gly | Val | Leu | Ser | Cys | Gln | Pro | Gly | Ala | Pro | Cys | *   |
|     | 370 |     |     |     |     | 375 |     |     |     |     | 380 |     |     |     |     |

| GCA | CTG | CA  |     |     |     |     |     |     |     |     |     |     |     |     |     | 1160

( 2 ) INFORMATION FOR SEQ ID NO:78:

( i ) SEQUENCE CHARACTERISTICS:
        ( A ) LENGTH: 383 amino acids
        ( B ) TYPE: amino acid
        ( D ) TOPOLOGY: linear ( i i ) MOLECULE TYPE: protein ( x i ) SEQUENCE DESCRIPTION: SEQ ID NO:78:

| Leu | Tyr | Phe | Thr | Leu | Ala | Leu | Val | Thr | Leu | Leu | Gln | Pro | Val | Arg | Ser |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |

| Ala | Glu | Asp | Leu | Gln | Glu | Ile | Leu | Pro | Ser | Ala | Asn | Glu | Thr | Arg | Ser |
|     |     |     | 20  |     |     |     |     | 25  |     |     |     |     | 30  |     |     |

| Leu | Thr | Thr | Cys | Gly | Thr | Tyr | Asn | Ile | Ile | Asp | Gly | Cys | Trp | Arg | Gly |
|     |     | 35  |     |     |     |     | 40  |     |     |     |     | 45  |     |     |     |

| Lys | Ala | Asp | Trp | Ala | Glu | Asn | Arg | Lys | Ala | Leu | Ala | Asp | Cys | Ala | Gln |
| 50  |     |     |     |     | 55  |     |     |     |     | 60  |     |     |     |     |     |

| | | | | | | | | | | | | | | | |
|---|---|---|---|---|---|---|---|---|---|---|---|---|---|---|---|
| Gly | Phe | Ala | Lys | Gly | Thr | Ile | Gly | Gly | Lys | Asp | Gly | Asp | Ile | Tyr | Thr |
| 65 | | | | 70 | | | | | 75 | | | | | | 80 |
| Val | Thr | Ser | Glu | Leu | Asp | Asp | Val | Ala | Asn | Pro | Lys | Glu | Gly | Thr | |
| | | | | 85 | | | | 90 | | | | | | 95 | |
| Leu | Arg | Phe | Gly | Ala | Ala | Gln | Asn | Arg | Pro | Leu | Trp | Ile | Ile | Phe | Glu |
| | | | 100 | | | | | 105 | | | | | 110 | | |
| Arg | Asp | Met | Val | Ile | Arg | Leu | Asp | Arg | Glu | Leu | Ala | Ile | Asn | Asn | Asp |
| | | 115 | | | | 120 | | | | | | 125 | | | |
| Lys | Thr | Ile | Asp | Gly | Arg | Gly | Ala | Lys | Val | Glu | Ile | Ile | Asn | Ala | Gly |
| | 130 | | | | | 135 | | | | | 140 | | | | |
| Phe | Ala | Ile | Tyr | Asn | Val | Lys | Asn | Ile | Ile | Ile | His | Asn | Ile | Ile | Met |
| 145 | | | | | 150 | | | | | 155 | | | | | 160 |
| His | Asp | Ile | Val | Val | Asn | Pro | Gly | Gly | Leu | Ile | Lys | Ser | His | Asp | Gly |
| | | | | 165 | | | | | 170 | | | | | 175 | |
| Pro | Pro | Val | Pro | Arg | Lys | Gly | Ser | Asp | Gly | Asp | Ala | Ile | Gly | Ile | Ser |
| | | | 180 | | | | | 185 | | | | | 190 | | |
| Gly | Gly | Ser | Gln | Ile | Trp | Ile | Asp | His | Cys | Ser | Leu | Ser | Lys | Ala | Val |
| | | 195 | | | | | 200 | | | | | 205 | | | |
| Asp | Gly | Leu | Ile | Asp | Ala | Lys | His | Gly | Ser | Thr | His | Phe | Thr | Val | Ser |
| | 210 | | | | | 215 | | | | | 220 | | | | |
| Asn | Cys | Leu | Phe | Thr | Gln | His | Gln | Tyr | Leu | Leu | Leu | Phe | Trp | Asp | Phe |
| 225 | | | | | 230 | | | | | 235 | | | | | 240 |
| Asp | Glu | Arg | Gly | Met | Leu | Cys | Thr | Val | Ala | Phe | Asn | Lys | Phe | Thr | Asp |
| | | | | 245 | | | | | 250 | | | | | 255 | |
| Asn | Val | Asp | Gln | Arg | Met | Pro | Asn | Leu | Arg | His | Gly | Phe | Val | Gln | Val |
| | | | 260 | | | | | 265 | | | | | 270 | | |
| Val | Asn | Asn | Asn | Tyr | Glu | Arg | Trp | Gly | Ser | Tyr | Ala | Leu | Gly | Gly | Ser |
| | | 275 | | | | | 280 | | | | | 285 | | | |
| Ala | Gly | Pro | Thr | Ile | Leu | Ser | Gln | Gly | Asn | Arg | Phe | Leu | Ala | Ser | Asp |
| | 290 | | | | | 295 | | | | | 300 | | | | |
| Ile | Lys | Lys | Glu | Val | Val | Gly | Arg | Tyr | Gly | Glu | Ser | Ala | Met | Ser | Glu |
| 305 | | | | | 310 | | | | | 315 | | | | | 320 |
| Ser | Ile | Asn | Trp | Asn | Trp | Arg | Ser | Tyr | Met | Asp | Val | Phe | Glu | Asn | Gly |
| | | | | 325 | | | | | 330 | | | | | 335 | |
| Ala | Ile | Phe | Val | Pro | Ser | Gly | Val | Asp | Pro | Val | Leu | Thr | Pro | Glu | Gln |
| | | | 340 | | | | | 345 | | | | | 350 | | |
| Asn | Ala | Gly | Met | Ile | Pro | Ala | Glu | Pro | Gly | Glu | Ala | Val | Leu | Arg | Leu |
| | | 355 | | | | | 360 | | | | | 365 | | | |
| Thr | Ser | Ser | Ala | Gly | Val | Leu | Ser | Cys | Gln | Pro | Gly | Ala | Pro | Cys | |
| | 370 | | | | | 375 | | | | | 380 | | | | |

( 2 ) INFORMATION FOR SEQ ID NO:79:

( i ) SEQUENCE CHARACTERISTICS:
        ( A ) LENGTH: 1368 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..1366

( x i ) SEQUENCE DESCRIPTION: SEQ ID NO:79:

| | | | | | | | | | | | | | | | | |
|---|---|---|---|---|---|---|---|---|---|---|---|---|---|---|---|---|
| TTG | TAT | TTT | ACC | TTA | GCA | CTT | GTC | ACT | TTG | GTG | CAA | GCT | GGA | CGT | CTT | 48 |
| Leu | Tyr | Phe | Thr | Leu | Ala | Leu | Val | Thr | Leu | Val | Gln | Ala | Gly | Arg | Leu | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| GGC | GAA | GAG | GTC | GAC | ATC | TTA | CCT | TCA | CCT | AAC | GAT | ACA | AGG | AGG | AGC | 96 |
| Gly | Glu | Glu | Val 20 | Asp | Ile | Leu | Pro 25 | Ser | Pro | Asn | Asp | Thr | Arg 30 | Arg | Ser | |
| CTG | CAA | GGA | TGT | GAA | GCA | CAC | AAC | ATT | ATA | GAC | AAG | TGT | TGG | AGG | TGC | 144 |
| Leu | Gln | Gly 35 | Cys | Glu | Ala | His | Asn 40 | Ile | Ile | Asp | Lys | Cys 45 | Trp | Arg | Cys | |
| AAA | CCC | GAT | TGG | GCG | GAG | AAC | CGA | CAA | GCG | TTA | GGC | GAT | TGT | GCG | CAA | 192 |
| Lys | Pro 50 | Asp | Trp | Ala | Glu | Asn 55 | Arg | Gln | Ala | Leu | Gly 60 | Asp | Cys | Ala | Gln | |
| GGT | TTT | GGA | AAG | GCA | ACT | CAC | GGC | GGA | AAA | TGG | GGT | GAT | ATC | TAC | ATG | 240 |
| Gly 65 | Phe | Gly | Lys | Ala | Thr 70 | His | Gly | Gly | Lys | Trp 75 | Gly | Asp | Ile | Tyr | Met 80 | |
| GTC | ACA | AGT | GAT | CAG | GAT | GAT | GAT | GTT | GTA | AAT | CCA | AAA | GAA | GGC | ACA | 288 |
| Val | Thr | Ser | Asp | Gln 85 | Asp | Asp | Asp | Val | Val 90 | Asn | Pro | Lys | Glu | Gly 95 | Thr | |
| CTC | CGG | TTC | GGT | GCT | ACC | CAG | GAC | AGG | CCC | TTG | TGG | ATC | ATT | TTT | CAA | 336 |
| Leu | Arg | Phe 100 | Gly | Ala | Thr | Gln | Asp | Arg 105 | Pro | Leu | Trp | Ile | Ile 110 | Phe | Gln | |
| AGA | GAT | ATG | ATT | ATT | TAT | TTG | CAA | CAA | GAG | ATG | GTC | GTA | ACC | AGC | GAC | 384 |
| Arg | Asp | Met 115 | Ile | Ile | Tyr | Leu | Gln 120 | Gln | Glu | Met | Val | Val 125 | Thr | Ser | Asp | |
| ACG | ACC | ATT | GAT | GGT | CGA | GGG | GCG | AAA | GTT | GAG | CTC | GTT | TAT | GGA | GGT | 432 |
| Thr | Thr | Ile 130 | Asp | Gly | Arg | Gly | Ala 135 | Lys | Val | Glu | Leu | Val 140 | Tyr | Gly | Gly | |
| ATC | ACC | CTC | ATG | AAT | GTC | AAG | AAT | GTA | ATC | ATT | CAC | AAC | ATA | GAT | ATC | 480 |
| Ile | Thr | Leu | Met | Asn 150 | Val | Lys | Asn | Val | Ile 155 | Ile | His | Asn | Ile | Asp 160 | Ile | |
| 145 | | | | | | | | | | | | | | | | |
| CAT | GAT | GTT | AGA | GTG | CTT | CCA | GGA | GGT | AGG | ATT | AAG | TCC | AAT | GGT | GGT | 528 |
| His | Asp | Val | Arg | Val 165 | Leu | Pro | Gly | Gly | Arg 170 | Ile | Lys | Ser | Asn | Gly 175 | Gly | |
| CCA | GCC | ATA | CCA | AGA | CAT | CAG | AGT | GAT | GGT | GAT | GCT | ATC | CAT | GTT | ACG | 576 |
| Pro | Ala | Ile | Pro 180 | Arg | His | Gln | Ser | Asp 185 | Gly | Asp | Ala | Ile | His 190 | Val | Thr | |
| GGT | AGT | TCA | GAC | ATA | TGG | ATC | GAC | CAT | TGC | ACG | CTC | AGT | AAG | TCA | TTT | 624 |
| Gly | Ser | Ser 195 | Asp | Ile | Trp | Ile | Asp 200 | His | Cys | Thr | Leu | Ser 205 | Lys | Ser | Phe | |
| GAT | GGG | CTC | GTC | GAT | GTC | AAC | TGG | GGC | AGC | ACA | GGA | GTA | ACC | ATT | TCC | 672 |
| Asp | Gly 210 | Leu | Val | Asp | Val | Asn 215 | Trp | Gly | Ser | Thr | Gly 220 | Val | Thr | Ile | Ser | |
| AAC | TGC | AAA | TTC | ACC | CAC | CAC | GAA | AAA | GCT | GTT | TTG | CTC | GGG | GCT | AGT | 720 |
| Asn | Cys | Lys | Phe | Thr 230 | His | His | Glu | Lys | Ala 235 | Val | Leu | Leu | Gly | Ala 240 | Ser | |
| 225 | | | | | | | | | | | | | | | | |
| GAC | ACG | CAT | TTT | CAA | GAT | CTG | AAA | ATG | CAT | GTA | ACG | CTT | GCA | TAC | AAC | 768 |
| Asp | Thr | His | Phe | Gln 245 | Asp | Leu | Lys | Met | His 250 | Val | Thr | Leu | Ala | Tyr 255 | Asn | |
| ATC | TTC | ACC | AAT | ACC | GTT | CAC | GAA | AGA | ATG | CCC | AGA | TGC | CGA | TTT | GGG | 816 |
| Ile | Phe | Thr | Asn 260 | Thr | Val | His | Glu | Arg 265 | Met | Pro | Arg | Cys | Arg 270 | Phe | Gly | |
| TTT | TTC | CAA | ATC | GTT | AAC | AAC | TTC | TAC | GAC | AGA | TGG | GAT | AAG | TAC | GCC | 864 |
| Phe | Phe | Gln 275 | Ile | Val | Asn | Asn | Phe 280 | Tyr | Asp | Arg | Trp | Asp 285 | Lys | Tyr | Ala | |
| ATC | GGT | GGT | AGC | TCG | AAC | CCT | ACT | ATT | CTC | AGC | CAA | GGG | AAC | AAA | TTC | 912 |
| Ile | Gly | Gly 290 | Ser | Ser | Asn | Pro 295 | Thr | Ile | Leu | Ser | Gln 300 | Gly | Asn | Lys | Phe | |
| GTG | GCC | CCC | GAT | TTC | ATT | TAC | AAG | AAA | AAC | GTC | TGT | CTA | AGG | ACT | GGT | 960 |
| Val | Ala | Pro | Asp | Phe 310 | Ile | Tyr | Lys | Lys | Asn 315 | Val | Cys | Leu | Arg | Thr 320 | Gly | |
| 305 | | | | | | | | | | | | | | | | |
| GCA | CAG | GAG | CCA | GAA | TGG | ATG | ACT | TGG | AAC | TGG | AGA | ACA | CAA | AAC | GAC | 1008 |
| Ala | Gln | Glu | Pro | Glu 325 | Trp | Met | Thr | Trp | Asn 330 | Trp | Arg | Thr | Gln | Asn 335 | Asp | |

```
GTG CTT GAA AAT GGT GCT ATC TTT GTG GCA TCT GGG TCT GAT CCA GTG    1056
Val Leu Glu Asn Gly Ala Ile Phe Val Ala Ser Gly Ser Asp Pro Val
            340                 345                 350

CTA ACC GCT GAA CAA AAT GCA GGC ATG ATG CAA GCT GAA CCG GGA GAT    1104
Leu Thr Ala Glu Gln Asn Ala Gly Met Met Gln Ala Glu Pro Gly Asp
            355                 360                 365

ATG GTT CCA CAA CTC ACC ATG AAT GCA GGT GTA CTC ACA TGC TCG CCT    1152
Met Val Pro Gln Leu Thr Met Asn Ala Gly Val Leu Thr Cys Ser Pro
            370                 375                 380

GGA GCA CCT TGC TAA GCA CCT GGC CAA TTC CTA TGC AAC GAT CAT AAA    1200
Gly Ala Pro Cys  *  Ala Pro Gly Gln Phe Leu Cys Asn Asp His Lys
385                 390                 395                 400

TAC TTG CTC ACC ATA AGT GTT CAT TTG ATT AGA TTT GGA CAC GAA TGA    1248
Tyr Leu Leu Thr Ile Ser Val His Leu Ile Arg Phe Gly His Glu  *
            405                 410                 415

TGT AAC CGA TTC GTC TGA ATT ATG ATT TGT TTT GAT TCT CAG TTT CAT    1296
Cys Asn Arg Phe Val  *  Ile Met Ile Cys Phe Asp Ser Gln Phe His
            420                 425                 430

AAT ATG GCT TCT TGA GAG CAA AAT TAG AGA AGA GTG TCT TTG ATC AAC    1344
Asn Met Ala Ser  *  Glu Gln Asn  *  Arg Arg Val Ser Leu Ile Asn
            435                 440                 445

TAC ATT TTA TGG TTT TTA TAT T AA                                   1368
Tyr Ile Leu Trp Phe Leu Tyr
450                 455
```

(2) INFORMATION FOR SEQ ID NO:80:

(i) SEQUENCE CHARACTERISTICS:
      (A) LENGTH: 388 amino acids
      (B) TYPE: amino acid
      (D) TOPOLOGY: linear (ii) MOLECULE TYPE: protein (xi) SEQUENCE DESCRIPTION: SEQ ID NO:80:

```
Leu Tyr Phe Thr Leu Ala Leu Val Thr Leu Val Gln Ala Gly Arg Leu
 1               5                  10                  15

Gly Glu Glu Val Asp Ile Leu Pro Ser Pro Asn Asp Thr Arg Arg Ser
            20                  25                  30

Leu Gln Gly Cys Glu Ala His Asn Ile Ile Asp Lys Cys Trp Arg Cys
        35                  40                  45

Lys Pro Asp Trp Ala Glu Asn Arg Gln Ala Leu Gly Asp Cys Ala Gln
    50                  55                  60

Gly Phe Gly Lys Ala Thr His Gly Gly Lys Trp Gly Asp Ile Tyr Met
65                  70                  75                  80

Val Thr Ser Asp Gln Asp Asp Val Val Asn Pro Lys Glu Gly Thr
                85                  90                  95

Leu Arg Phe Gly Ala Thr Gln Asp Arg Pro Leu Trp Ile Ile Phe Gln
                100                 105                 110

Arg Asp Met Ile Ile Tyr Leu Gln Gln Glu Met Val Val Thr Ser Asp
            115                 120                 125

Thr Thr Ile Asp Gly Arg Gly Ala Lys Val Glu Leu Val Tyr Gly Gly
    130                 135                 140

Ile Thr Leu Met Asn Val Lys Asn Val Ile Ile His Asn Ile Asp Ile
145                 150                 155                 160

His Asp Val Arg Val Leu Pro Gly Gly Arg Ile Lys Ser Asn Gly Gly
                165                 170                 175

Pro Ala Ile Pro Arg His Gln Ser Asp Gly Asp Ala Ile His Val Thr
            180                 185                 190
```

```
Gly  Ser  Ser  Asp  Ile  Trp  Ile  Asp  His  Cys  Thr  Leu  Ser  Lys  Ser  Phe
          195                 200                      205

Asp  Gly  Leu  Val  Asp  Val  Asn  Trp  Gly  Ser  Thr  Gly  Val  Thr  Ile  Ser
     210                 215                      220

Asn  Cys  Lys  Phe  Thr  His  His  Glu  Lys  Ala  Val  Leu  Leu  Gly  Ala  Ser
225                      230                      235                           240

Asp  Thr  His  Phe  Gln  Asp  Leu  Lys  Met  His  Val  Thr  Leu  Ala  Tyr  Asn
               245                      250                           255

Ile  Phe  Thr  Asn  Thr  Val  His  Glu  Arg  Met  Pro  Arg  Cys  Arg  Phe  Gly
               260                 265                      270

Phe  Phe  Gln  Ile  Val  Asn  Asn  Phe  Tyr  Asp  Arg  Trp  Asp  Lys  Tyr  Ala
          275                 280                      285

Ile  Gly  Gly  Ser  Ser  Asn  Pro  Thr  Ile  Leu  Ser  Gln  Gly  Asn  Lys  Phe
     290                      295                      300

Val  Ala  Pro  Asp  Phe  Ile  Tyr  Lys  Lys  Asn  Val  Cys  Leu  Arg  Thr  Gly
305                      310                      315                           320

Ala  Gln  Glu  Pro  Glu  Trp  Met  Thr  Trp  Asn  Trp  Arg  Thr  Gln  Asn  Asp
               325                      330                           335

Val  Leu  Glu  Asn  Gly  Ala  Ile  Phe  Val  Ala  Ser  Gly  Ser  Asp  Pro  Val
               340                      345                           350

Leu  Thr  Ala  Glu  Gln  Asn  Ala  Gly  Met  Met  Gln  Ala  Glu  Pro  Gly  Asp
               355                      360                      365

Met  Val  Pro  Gln  Leu  Thr  Met  Asn  Ala  Gly  Val  Leu  Thr  Cys  Ser  Pro
     370                      375                      380

Gly  Ala  Pro  Cys
385
```

( 2 ) INFORMATION FOR SEQ ID NO:81:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: protein ( x i ) SEQUENCE DESCRIPTION: SEQ ID NO:81:

```
Ala  Pro  Asp  Gln  Leu  Leu  Ser  Thr  Tyr  Asn  Asp  His
1                   5                        10
```

( 2 ) INFORMATION FOR SEQ ID NO:82:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: protein ( x i ) SEQUENCE DESCRIPTION: SEQ ID NO:82:

```
Tyr  Phe  Phe  Leu  Phe  Tyr  Phe
1                   5
```

( 2 ) INFORMATION FOR SEQ ID NO:83:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: protein ( x i ) SEQUENCE DESCRIPTION: SEQ ID NO:83:

Tyr Phe Ile Cys Thr Lys Val Met Glu Met Asn Leu Tyr
1               5                   10

Leu Leu Val Leu
    15

( 2 ) INFORMATION FOR SEQ ID NO:84:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: protein ( x i ) SEQUENCE DESCRIPTION: SEQ ID NO:84:

Lys Lys Lys Lys Pro Asn
1               5

( 2 ) INFORMATION FOR SEQ ID NO:85:

( i ) SEQUENCE CHARACTERISTICS:
        ( A ) LENGTH: 42 amino acids
        ( B ) TYPE: amino acid
        ( D ) TOPOLOGY: linear ( i i ) MOLECULE TYPE: protein ( x i ) SEQUENCE DESCRIPTION: SEQ ID NO:85:

Ala Pro Gly Gln Phe Leu Ser Phe Tyr Asn Asn His Lys Tyr Leu Phe Tyr
1               5                   10                  15

Phe Ile Phe Asp Ile Leu Tyr Glu Pro Leu Arg Ser Ser Thr Leu Leu
                20                  25                  30

Thr Cys Phe Lys Phe Ile Arg Val Tyr
            35                  40

( 2 ) INFORMATION FOR SEQ ID NO:86:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: protein ( x i ) SEQUENCE DESCRIPTION: SEQ ID NO:86:

Tyr Phe Ile Cys Thr Lys Val Met Glu Met Asn Leu Tyr
1               5                   10

Leu Leu Ser Thr
    15

( 2 ) INFORMATION FOR SEQ ID NO:87:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: protein ( x i ) SEQUENCE DESCRIPTION: SEQ ID NO:87:

Ala Pro Cys Gln Phe Ser
1               5

( 2 ) INFORMATION FOR SEQ ID NO:88:

( i ) SEQUENCE CHARACTERISTICS:
  ( A ) LENGTH: 13 amino acids
  ( B ) TYPE: amino acid
  ( D ) TOPOLOGY: linear ( i i ) MOLECULE TYPE: protein ( x i ) SEQUENCE DESCRIPTION: SEQ ID NO:88:

Ala Phe Ala Met Ile Lys Asn Thr Phe Leu Phe Tyr Phe
1               5                   10

( 2 ) INFORMATION FOR SEQ ID NO:89:

( i ) SEQUENCE CHARACTERISTICS:
  ( A ) LENGTH: 15 amino acids
  ( B ) TYPE: amino acid
  ( D ) TOPOLOGY: linear ( i i ) MOLECULE TYPE: protein ( x i ) SEQUENCE DESCRIPTION: SEQ ID NO:89:

Tyr Phe Ile Cys Thr Gly Asn Glu Pro Leu Pro Ser Ser
1               5                   10

Thr Leu
    15

( 2 ) INFORMATION FOR SEQ ID NO:90:

( i ) SEQUENCE CHARACTERISTICS:
  ( A ) LENGTH: 26 amino acids
  ( B ) TYPE: amino acid
  ( D ) TOPOLOGY: linear ( i i ) MOLECULE TYPE: protein ( x i ) SEQUENCE DESCRIPTION: SEQ ID NO:90:

Ala Pro Gly Gln Phe Leu Cys Asn Asp His Lys Tyr Leu Leu Thr Ile Ser Val
1               5                   10                  15

Leu Ile Arg Phe Gly His Glu
        20              25

( 2 ) INFORMATION FOR SEQ ID NO:91:

( i ) SEQUENCE CHARACTERISTICS:
  ( A ) LENGTH: 5 amino acids
  ( B ) TYPE: amino acid
  ( D ) TOPOLOGY: linear ( i i ) MOLECULE TYPE: protein ( x i ) SEQUENCE DESCRIPTION: SEQ ID NO:91:

Cys Asn Arg Phe Val
1               5

( 2 ) INFORMATION FOR SEQ ID NO:92:

( i ) SEQUENCE CHARACTERISTICS:
  ( A ) LENGTH: 14 amino acids
  ( B ) TYPE: amino acid
  ( D ) TOPOLOGY: linear ( i i ) MOLECULE TYPE: protein ( x i ) SEQUENCE DESCRIPTION: SEQ ID NO:92:

Ile Met Ile Cys Phe Asp Ser Gln Phe His Asn Met Ala Ser
1               5                   10

( 2 ) INFORMATION FOR SEQ ID NO:93:

( i ) SEQUENCE CHARACTERISTICS:
  ( A ) LENGTH: 14 amino acids
  ( B ) TYPE: amino acid
  ( D ) TOPOLOGY: linear ( i i ) MOLECULE TYPE: protein ( x i ) SEQUENCE DESCRIPTION: SEQ ID NO:93:

Arg Arg Val Ser Leu Ile Asn Tyr Ile Leu Trp Phe Leu Tyr
 1           5                  10

We claim:

1. An isolated nucleic acid comprising a nucleotide sequence which encodes a protein comprising an amino acid sequence selected from the group consisting of: the amino acid sequence of Amb a IA, as represented by amino acid residues 1–387 in SEQ ID NO: 72, or a polymorphic variant thereof; the amino acid sequence of Amb a IB, as represented by amino acid residues 1–441 in SEQ ID NO: 74, or a polymorphic variant thereof; the amino acid sequence of Amb a IC, as represented by amino acid residues 1–434 in SEQ ID NO: 76, or a polymorphic variant thereof; and the amino acid sequence of Amb a ID, as represented by amino acid residues 1–383 in SEQ ID NO: 78, or a polymorphic variant thereof.

2. A host cell transformed with the nucleic acid of claim 1.

3. An isolated nucleic acid comprising a nucleotide sequence selected from the group consisting of: the nucleotide sequence of Amb a IA, as represented by nucleotides 1–1164 in SEQ ID NO: 71 or a polymorphic variant thereof; the nucleotide sequence of Amb a IB, as represented by nucleotides 1–1326 in SEQ ID NO: 73 or a polymorphic variant thereof; the nucleotide sequence of Amb a IC, as represented by nucleotides 1–1305 in SEQ ID NO: 75 or a polymorphic variant thereof; and the nucleotide sequence of Amb a ID, as represented by nucleotides 1–1152 in SEQ ID NO: 77 or a polymorphic variant thereof.

4. An expression vector comprising the nucleic acid of claim 3.

5. An isolated nucleic acid comprising a nucleotide sequence encoding a ragweed pollen allergen which hybridizes under high stringency conditions to a nucleotide sequence selected from the group consisting of: the nucleotide sequence of Amb a IA as represented by nucleotides 1–1164 in SEQ ID NO: 71; the nucleotide sequence of Amb a IB as represented by nucleotides 1–1326 in SEQ ID NO: 73; the nucleotide sequence of Amb a IC as represented by nucleotides 1–1305 in SEQ ID NO: 75 and the nucleotide sequence of Amb a ID as represented by nucleotides 1–1152 in SEQ ID NO: 77.

6. An isolated nucleic acid comprising a nucleotide sequence which encodes a protein comprising the amino acid sequence of Amb a II, as represented in SEQ ID NO: 80 or a polymorphic variant thereof.

7. A host cell transformed with the nucleic acid of claim 1.

8. An isolated nucleic acid comprising the nucleotide sequence of Amb a II, as represented in SEQ ID NO: 79 or a polymorphic variant thereof.

9. An expression vector comprising the nucleic acid of claim 8.

10. An isolated nucleic acid comprising a nucleotide sequence encoding a ragweed pollen allergen which hybridizes under high stringency conditions to the nucleotide sequence of Amb a II as shown in SEQ ID NO: 79.

11. An isolated nucleic acid comprising a nucleotide sequence which encodes an Amb a IA peptide comprising at least a portion of the amino acid sequence shown in SEQ ID NO: 72, an Amb a IB peptide comprising at least a portion of the amino acid sequence shown in SEQ ID NO: 74, an Amb a IC peptide comprising at least a portion of the amino acid sequence shown in SEQ ID NO: 76, or an Amb a ID peptide comprising at least a portion of the amino acid sequence shown in SEQ ID NO: 78, said peptide comprising at least one T cell epitope.

12. The isolated nucleic acid of claim 11 wherein the Amb a IA, Amb a IB, Amb a IC, or Amb a ID peptide comprises an amino acid sequence selected from the group consisting of:

a) YTVTSDKDDDVANC (SEQ ID NO: 52);
b) GKADWAENRC (SEQ ID NO: 53);
c) LENGAIFVASGVDPVLTPEQ (SEQ ID NO: 54); and
d) GFFQVVNNNYDRWGTYA (SEQ ID NO: 55).

13. The isolated nucleic acid of claim 11 comprising a nucleotide sequence which encodes a peptide comprising at least eight amino acid residues of the amino acid sequence selected from the group consisting of: a portion of the amino acid sequence of Amb a IA, as represented by amino acid residues 1–387 in SEQ ID NO: 72; a portion of the amino acid sequence of Amb a IB, as represented by amino acid residues 1–441 in SEQ ID NO: 74; a portion of the amino acid sequence of Amb a IC, as represented by amino acid residues 1–434 in SEQ ID NO: 76; and a portion of the amino acid sequence of Amb a ID, as represented by amino acid residues 1–383 in SEQ ID NO: 78.

14. The isolated nucleic acid of claim 11, wherein the peptide comprises at least one T cell epitope which is recognized by a human T cell receptor specific for an Amb a I protein.

15. An isolated nucleic acid comprising a nucleotide sequence which encodes an Amb a IA peptide comprising at least a portion of the amino acid sequence shown in SEQ ID NO: 72, an Amb a IB peptide comprising at least a portion of the amino acid sequence shown in SEQ ID NO: 74, an Amb a IC peptide comprising at least a portion of the amino acid sequence shown in SEQ ID NO: 76, or an Amb a ID peptide comprising at least a portion of the amino acid sequence shown in SEQ ID NO: 78, said peptide comprising at least one B cell epitope.

16. An isolated nucleic acid comprising a nucleotide sequence encoding an Amb a I peptide which comprises the following amino acid sequence: W E N F K (SEQ ID NO: 1), wherein W represents the amino acid tryptophan; E represents the amino acid glutamic acid; N represents the amino acid asparagine; F represents the amino acid phenylalanine; and K represents the amino acid lysine.

17. An isolated nucleic acid comprising a nucleotide sequence which encodes an Amb a II peptide, said peptide comprising at least one T cell epitope and at least a portion of the amino acid sequence shown in SEQ ID NO: 80.

18. The isolated nucleic acid of claim 17 comprising a nucleotide sequence which encodes a peptide comprising at least eight amino acid residues of the amino acid sequence of Amb a II, as represented in SEQ ID NO: 80.

19. The isolated nucleic acid of claim 17, wherein the peptide comprises at least one T cell epitope which is recognized by a human T cell receptor specific for an Amb a II protein.

20. An isolated nucleic acid comprising a nucleotide sequence which encodes an Amb a II peptide, said peptide comprising at least one B cell epitope and at least a portion of the amino acid sequence shown in SEQ ID NO: 80.

* * * * *

UNITED STATES PATENT AND TRADEMARK OFFICE
CERTIFICATE OF CORRECTION

PATENT NO. : 5,776,761
DATED : July 7, 1998
INVENTOR(S) : Bruce Rogers et al.

It is certified that error appears in the above-identified patent and that said Letters Patent is hereby corrected as shown below:

On the title page, column two at "Attorney, Agent, or Firm", delete "LL" and insert therefor --LLP--.

Signed and Sealed this

Sixteenth Day of March, 1999

Attest:

Q. TODD DICKINSON

Attesting Officer

Acting Commissioner of Patents and Trademarks